United States Patent [19]

Fischer, deceased

[11] 4,030,909

[45] June 21, 1977

[54] HERBICIDAL COMPOSITIONS

[75] Inventor: Adolf Fischer, deceased, late of Mutterstadt, Germany, by Caecilia Emma Fischer, heiress-at-law

[73] Assignee: BASF Aktiengesellschaft, Ludwigshafen (Rhine), Germany

[22] Filed: Oct. 22, 1975

[21] Appl. No.: 624,941

[30] Foreign Application Priority Data

Nov. 14, 1974 Germany .......................... 2453908

[52] U.S. Cl. ...................................... 71/91; 71/66; 71/86; 71/88; 71/92; 71/94; 71/95; 71/106; 71/107; 71/111; 71/113; 71/114; 71/115; 71/118; 71/122; 71/124; 260/239 A; 260/239 B; 260/239 BA; 260/456 NS

[51] Int. Cl.² .......................................... A01N 9/12

[58] Field of Search ........................ 71/91, 88, 103

[56] References Cited

UNITED STATES PATENTS

| | | | |
|---|---|---|---|
| 3,708,277 | 1/1973 | Zeidler et al. | 71/91 |
| 3,826,642 | 7/1974 | Fischer | 71/91 |
| 3,846,113 | 11/1974 | Fischer | 71/91 |
| 3,865,860 | 2/1975 | Rohr et al. | 71/103 |
| 3,868,245 | 2/1975 | Fischer | 71/91 |
| 3,870,740 | 3/1975 | Fischer et al. | 71/103 |
| 3,883,509 | 5/1975 | Fischer et al. | 71/91 |

*Primary Examiner*—Glennon H. Hollrah
*Attorney, Agent, or Firm*—Keil, Thompson & Shurtleff

[57] ABSTRACT

New and valuable herbicides containing compositions of benzothiadiazinone dioxides with other active ingredients.

9 Claims, No Drawings

HERBICIDAL COMPOSITIONS

The present invention relates to herbicides containing compositions with benzothiadiazinone dioxides.

It is known that sulfonylglycolic acid amides (German Laid-Open Applications DOS 2,201,432; DOS 2,334,715; and DOS 2,219,932), azetidine carbothiolates (German Laid-Open Application DOS 2,312,045), hexahydroazepine carbothiolates (German Laid-Open Application DOS 1,300,947), benzofuranyl sulfonates (German Laid-Open Application DOS 1,926,139), butynyl carbamates (German Laid-Open Application DOS 2,364,876), carboxylic acid derivatives (German 959,066), phosphonomethyl glycines (German Laid-Open Application DOS 2,152,826), phthalamides (British 671,153), anilides (British 903,766), pyrazolium compounds (German Laid-Open Application DOS 2,260,485) and nitrophenol derivatives (British 425,295) have a herbicidal action. However, the action of these compounds when used individually is not always satisfactory.

I have now found that compositions consisting of one or more of these active ingredients and benzothiadiazinone derivatives, which are known to be effective herbicidal active ingredients (German Laid-Open Application DOS 1,542,836), have, surprisingly, a herbicial action superior to that of their individual components.

The compositions consist of
a. a benzothiadiazinone dioxide of the formula

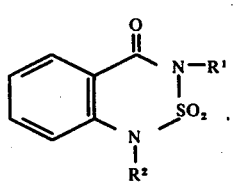

where $R^1$ denotes lower alkyl and $R^2$ denotes alkoxyalkyl, hydrogen or a cation, and b. a glycolic acid amide of the formula $$X-\overset{\underset{\|}{O}}{C}-CH_2-Y,$$

wherein X denotes

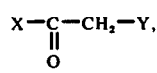

$R^1$ denoting alkyl, alkenyl, alkynyl, haloalkyl, haloalkenyl or haloalkynyl of a maximum of 6 carbon atoms, alkoxyalkyl, alkenoxyalkyl, alkynoxyalkyl or cycloalkyl and $R^2$ denoting phenyl which may be substituted by one or several identical or different groups, the number of substituents - which may be halogen, lower alkyl of a maximum of 4 carbon atoms, haloalkyl, alkoxy, alkylsulfonyl, alkylaminosulfonyl, cyano, hydroxy, nitro and amino - being from 1 to 3, and the carboxamide nitrogen is a ring member of an unsubstituted, halogen-substituted or lower alkyl-substituted, optionally bicyclic cycloalkylimine which may contain further hetero atoms in the ring and which has a maximum of 9 carbon atoms in the ring, and Y denotes

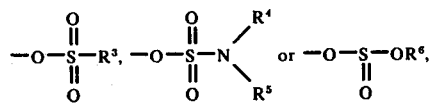

where $R^3$, $R^4$, $R^5$ and $R^6$ denote alkyl, alkenyl, alkynyl, haloalkyl, haloalkenyl or haloalkynyl having a maximum of 8 carbon atoms, or optionally substituted phenyl or cycloalkyl having a maximum of 8 carbon atoms, and $R^4$ and $R^5$ additionally denote hydrogen, or c. an azetidine carbothiolate of the formula

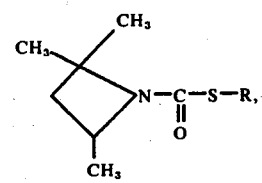

where R denotes unsubstituted or halogen-substituted alkyl, alkenyl, alkynyl, phenyl or benzyl, or d. a hexahydroazepine carbothiolate of the formula

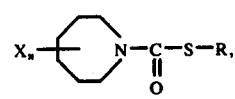

where X denotes methyl, n denotes one of the integers 2 and 3, and R denotes unsubstituted or halogen-substituted alkyl or benzyl, or e. a benzofuranyl sulfonate of the formula

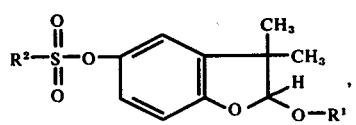

where $R^1$ denotes unsubstituted, halogen-substituted or alkoxy-substituted alkyl, alkenyl or alkynyl, the group

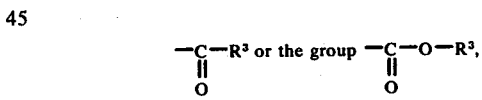

$R^3$ denoting hydrogen or unsubstituted or halogen-substituted lower alkyl, and $R^2$ denotes lower alkyl or the group

$R^4$ and $R^5$ denoting hydrogen, a cation, unsubstituted or halogen-substituted lower alkyl, alkenyl, alkynyl or acetyl, or the group

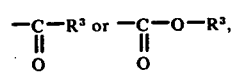

$R^3$ having the above meanings, or
  f. a butynyl carbamate of the formula

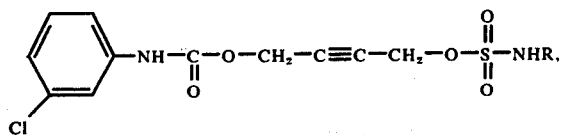

where R denotes hydrogen or unsubstituted or halogen-substituted alkyl, or g. a carboxylic acid derivative of the formula

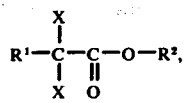

where $R^1$ denotes halogen, alkyl, haloalkyl, benzyl, phenylchloromethyl or benzamidooxy, X denotes hydrogen or halogen and $R^2$ denotes unsubstituted or halogen-substituted alkyl or benzyl, hydrogen or cations, or an ester or amido group, or h. the phosphonomethyl glycine of the formula

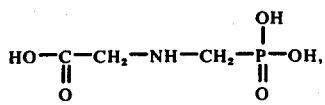

or a salt thereof, or i. the phthalamide of the formula

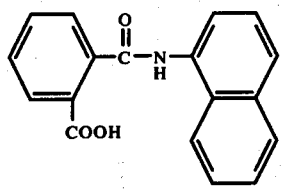

or j. an anilide of the formula

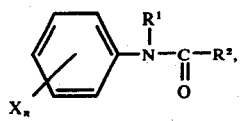

where X denotes halogen or lower alkyl, or alkoxy or a maximum of 4 carbon atoms, $n$ denotes one of the integers from 0 to 3, $R^1$ denotes hydrogen, alkyl or alkynyl and $R^2$ denotes unsubstituted or halogen-substituted alkyl, alkenyl or cycloalkyl, or k. a pyrazolium compound of the formula

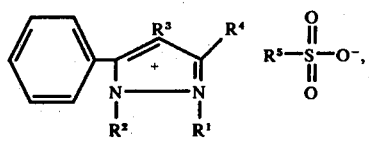

where $R^1$ denotes lower alkyl, $R^2$ denotes lower alkyl or alkoxy, $R^3$ denotes halogen, lower alkyl, lower alkoxy or phenyl, $R^4$ denotes phenyl or hydrogen, and $R^5$ denotes unsubstituted or halogen-substituted lower alkyl, or l. a nitrophenol derivative of the formula

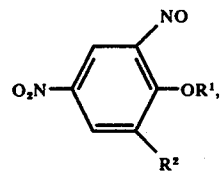

where $R^1$ denotes hydrogen, a cation or acetyl and $R^2$ denotes lower alkyl of a maximum of 5 carbon atoms.

The compositions may contain compounds of the formula a and one or more compounds of the formulae b to l.

The active ingredients listed in the following tables are examples of components:

| $R^1$ | $R^2$ |
|---|---|
| H | $CH_3$ |
| Na | $CH_3$ |
| $(CH_3CH_2)_3NH$ | $CH_3$ |
| $ClCH_2CH_2N(CH_3)CH_3$ | $CH_3$ |
| $ClCH_2CH_2N(CH_3)NH_2 \cdot CH_3$ | $CH_3$ |
| $(CH_3)_2NH_2$ | $CH_3$ |
| $(HOCH_2CH_2)_2NH_2$ | $CH_3$ |
| $HOCH_2CH_2NH_3$ | $CH_3$ |
| $n\text{-}C_4H_9NH_3$ | $CH_3$ |
| H | $C_2H_5$ |
| Na | $C_2H_5$ |
| $(CH_3)_3NH$ | $C_2H_5$ |

-continued

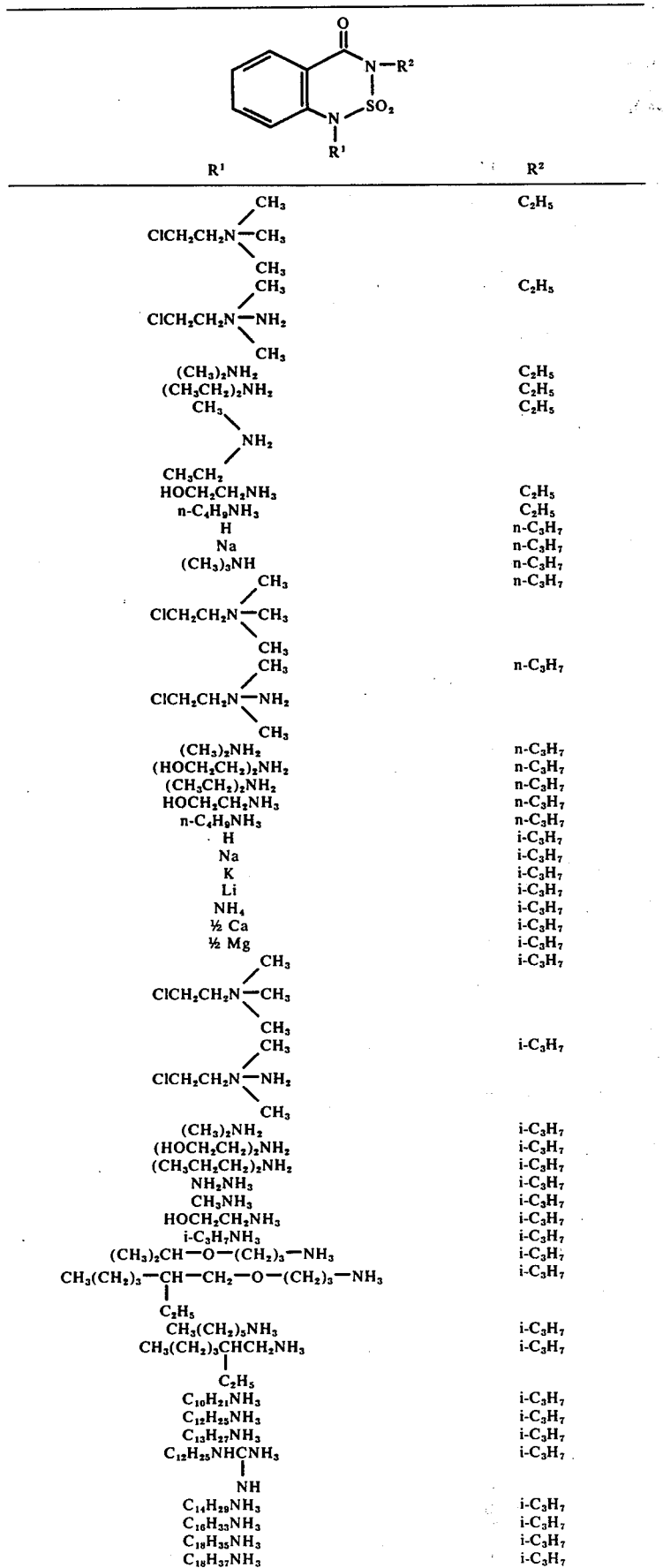

| R¹ | R² |
|---|---|
| CH₃—N(CH₃)— | C₂H₅ |
| ClCH₂CH₂N(CH₃)(CH₃) | |
| ClCH₂CH₂N(CH₃)(NH₂) | C₂H₅ |
| (CH₃)₂NH₂ | C₂H₅ |
| (CH₃CH₂)₂NH₂ | C₂H₅ |
| CH₃–CH(NH₂)–CH₂CH₃ | C₂H₅ |
| HOCH₂CH₂NH₃ | C₂H₅ |
| n-C₄H₉NH₃ | C₂H₅ |
| H | n-C₃H₇ |
| Na | n-C₃H₇ |
| (CH₃)₃NH | n-C₃H₇ |
| ClCH₂CH₂N(CH₃)(CH₃)(CH₃) | n-C₃H₇ |
| ClCH₂CH₂N(CH₃)(NH₂)(CH₃) | n-C₃H₇ |
| (CH₃)₂NH₂ | n-C₃H₇ |
| (HOCH₂CH₂)₂NH₂ | n-C₃H₇ |
| (CH₃CH₂)₂NH₂ | n-C₃H₇ |
| HOCH₂CH₂NH₃ | n-C₃H₇ |
| n-C₄H₉NH₃ | n-C₃H₇ |
| H | i-C₃H₇ |
| Na | i-C₃H₇ |
| K | i-C₃H₇ |
| Li | i-C₃H₇ |
| NH₄ | i-C₃H₇ |
| ½ Ca | i-C₃H₇ |
| ½ Mg | i-C₃H₇ |
| ClCH₂CH₂N(CH₃)(CH₃)(CH₃) | i-C₃H₇ |
| ClCH₂CH₂N(CH₃)(NH₂)(CH₃) | i-C₃H₇ |
| (CH₃)₂NH₂ | i-C₃H₇ |
| (HOCH₂CH₂)₂NH₂ | i-C₃H₇ |
| (CH₃CH₂CH₂)₂NH₂ | i-C₃H₇ |
| NH₂NH₃ | i-C₃H₇ |
| CH₃NH₃ | i-C₃H₇ |
| HOCH₂CH₂NH₃ | i-C₃H₇ |
| i-C₃H₇NH₃ | i-C₃H₇ |
| (CH₃)₂CH—O—(CH₂)₃—NH₃ | i-C₃H₇ |
| CH₃(CH₂)₃—CH(C₂H₅)—CH₂—O—(CH₂)₃—NH₃ | i-C₃H₇ |
| CH₃(CH₂)₅NH₃ | i-C₃H₇ |
| CH₃(CH₂)₃CH(C₂H₅)CH₂NH₃ | i-C₃H₇ |
| C₁₀H₂₁NH₃ | i-C₃H₇ |
| C₁₂H₂₅NH₃ | i-C₃H₇ |
| C₁₃H₂₇NH₃ | i-C₃H₇ |
| C₁₂H₂₅NHC(NH)NH | i-C₃H₇ |
| C₁₄H₂₉NH₃ | i-C₃H₇ |
| C₁₆H₃₃NH₃ | i-C₃H₇ |
| C₁₈H₃₅NH₃ | i-C₃H₇ |
| C₁₈H₃₇NH₃ | i-C₃H₇ |

-continued
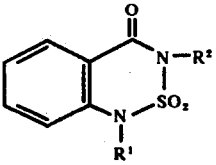
| R¹ | R² |
|---|---|
| | i-C₃H₇ |
|  | " |
| 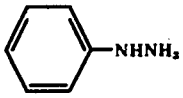 | " |
| 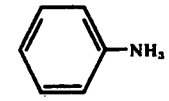 | " |
|  | " |
|  | " |
| 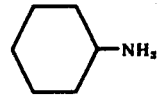 | " |
| 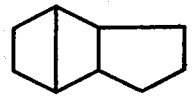 | " |
| 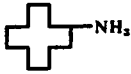 | " |
| 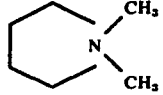 | " |
| 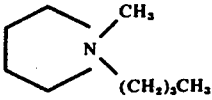 | " |
| 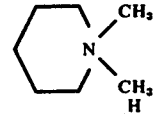 | " |
| 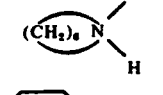 | " |
| 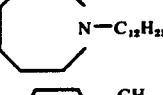 | " |
| 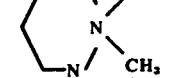 | " |
| C₆H₁₅NH₃ | " |
| H | n-C₄H₉ |
| Na | " |
| (CH₃)₂NH₂ | " |
| (HOCH₂CH₂)₂NH₂ | " |

-continued

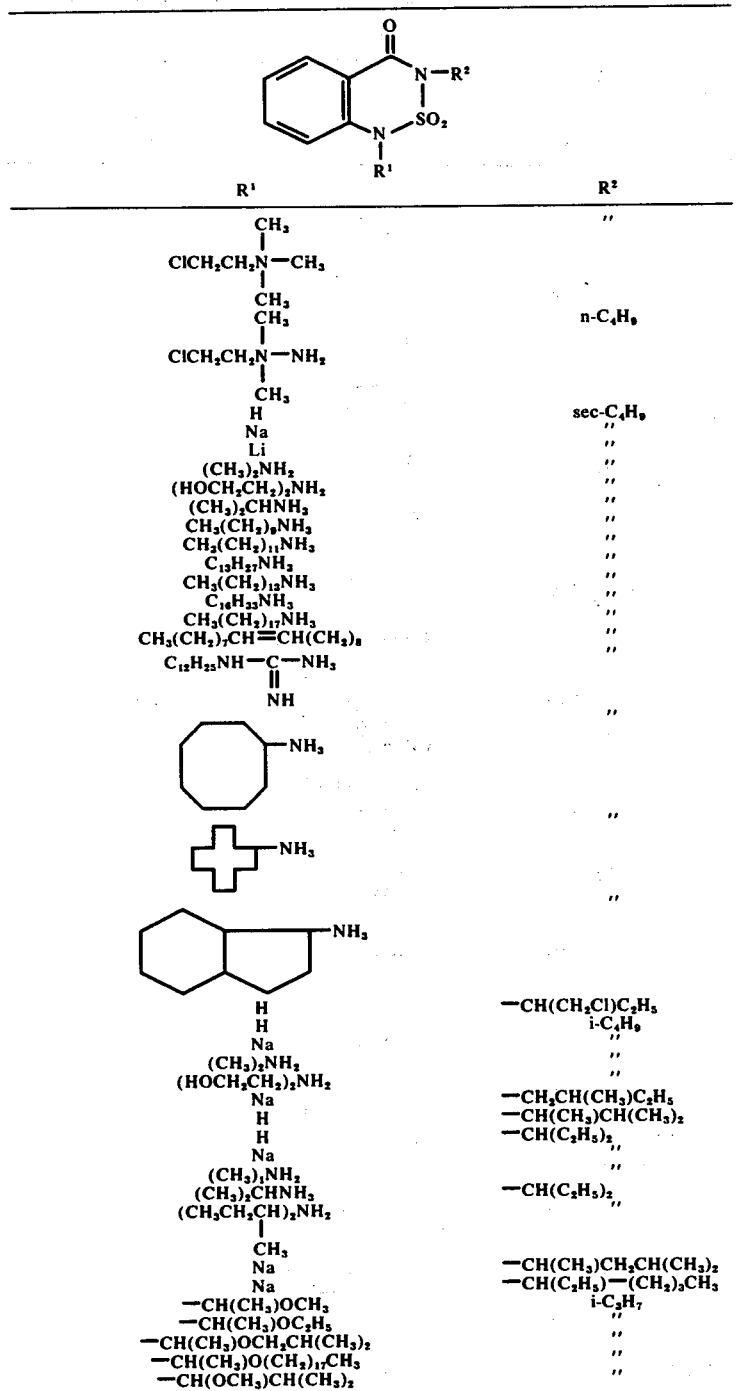

| R¹ | R² |
|---|---|
| CH₃<br>ClCH₂CH₂N—CH₃<br>CH₃ | " |
| CH₃<br>ClCH₂CH₂N—NH₂<br>CH₃ | n-C₄H₉ |
| H | sec-C₄H₉ |
| Na | " |
| Li | " |
| (CH₃)₂NH₂ | " |
| (HOCH₂CH₂)₃NH₂ | " |
| (CH₃)₂CHNH₃ | " |
| CH₃(CH₂)₆NH₃ | " |
| CH₃(CH₂)₁₁NH₃ | " |
| C₁₂H₂₇NH₃ | " |
| CH₃(CH₂)₁₂NH₃ | " |
| C₁₆H₃₃NH₃ | " |
| CH₃(CH₂)₁₇NH₃ | " |
| CH₃(CH₂)₇CH=CH(CH₂)₈ | " |
| C₁₂H₂₅NH—C—NH₃<br>‖<br>NH | " |
| cyclooctyl-NH₃ | " |
| adamantyl-NH₃ | " |
| decahydronaphthyl-NH₃ | " |
| H | —CH(CH₂Cl)C₂H₅ |
| Na | i-C₄H₉ |
| (CH₃)₂NH₂ | " |
| (HOCH₂CH₂)₃NH₂ | " |
| Na | —CH₂CH(CH₃)C₂H₅ |
| H | —CH(CH₃)CH(CH₃)₂ |
| H | —CH(C₂H₅)₂ |
| Na | " |
| (CH₃)₂NH₂ | —CH(C₂H₅)₂ |
| (CH₃)₂CHNH₃ | " |
| (CH₃CH₂CH)₂NH₂<br>│<br>CH₃ | —CH(CH₃)CH₂CH(CH₃)₂ |
| Na | —CH(C₂H₅)—(CH₂)₃CH₃ |
| Na | i-C₃H₇ |
| —CH(CH₃)OCH₃ | " |
| —CH(CH₃)OC₂H₅ | " |
| —CH(CH₃)OCH₂CH(CH₃)₂ | " |
| —CH(CH₃)O(CH₂)₁₇CH₃ | " |
| —CH(OCH₃)CH(CH₃)₂ | " |

-continued

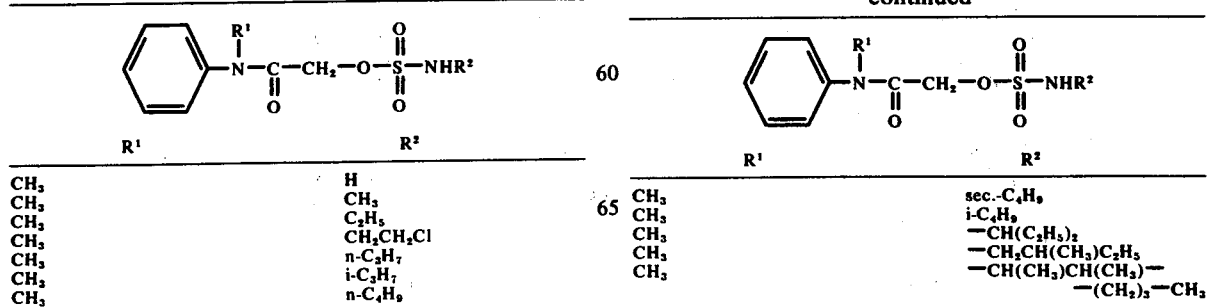

| R¹ | R² |
|---|---|
| CH₃ | H |
| CH₃ | CH₃ |
| CH₃ | C₂H₅ |
| CH₃ | CH₂CH₂Cl |
| CH₃ | n-C₃H₇ |
| CH₃ | i-C₃H₇ |
| CH₃ | n-C₄H₉ |
| CH₃ | sec.-C₄H₉ |
| CH₃ | i-C₄H₉ |
| CH₃ | —CH(C₂H₅)₂ |
| CH₃ | —CH₂CH(CH₃)C₂H₅ |
| CH₃ | —CH(CH₃)CH(CH₃)— |
| | —(CH₂)₃—CH₃ |

-continued

Structure: Phenyl-N(R¹)-C(=O)-CH₂-O-S(=O)₂-NHR²

| R¹ | R² |
|---|---|
| C₂H₅ | CH₃ |
| C₂H₅ | C₂H₅ |
| C₂H₅ | CH₂CH₂Cl |
| C₂H₅ | n-C₃H₇ |
| C₂H₅ | i-C₃H₇ |
| n-C₃H₇ | CH₃ |
| n-C₃H₇ | i-C₃H₇ |
| C₂H₅ | H |
| i-C₃H₇ | H |
| i-C₃H₇ | CH₃ |
| i-C₃H₇ | C₂H₅ |
| i-C₃H₇ | CH₂CH₂Cl |
| i-C₃H₇ | n-C₃H₇ |
| i-C₃H₇ | i-C₃H₇ |
| i-C₃H₇ | n-C₄H₉ |
| i-C₃H₇ | sec-C₄H₉ |
| i-C₃H₇ | cyclohexyl |
| CH₂—CH=CH₂ | CH₃ |
| CH₂—C≡CH | CH₃ |
| CH₂—C≡CH | i-C₃H₇ |
| n-C₄H₉ | CH₃ |
| n-C₄H₉ | C₂H₅ |
| n-C₄H₉ | n-C₄H₉ |
| n-C₄H₉ | i-C₃H₇ |
| sec-C₄H₉ | H |
| sec-C₄H₉ | CH₃ |
| sec-C₄H₉ | C₂H₅ |
| sec-C₄H₉ | CH₂CH₂Cl |
| sec-C₄H₉ | n-C₃H₉ |
| sec-C₄H₉ | i-C₃H₇ |
| i-C₄H₉ | i-C₃H₇ |
| tert-C₄H₉ | CH₃ |
| tert-C₄H₉ | CH₂CH₃ |
| tert-C₄H₉ | —CH₂CH₂Cl |
| tert-C₄H₉ | i-C₃H₇ |
| —CH(CH₃)—C≡CH | H |
| " | CH₃ |
| " | C₂H₅ |
| " | CH₂CH₂Cl |
| " | n-C₃H₇ |
| " | i-C₃H₇ |
| " | n-C₄H₉ |
| —CH(CH₃)CH=CH₂ | i-C₃H₇ |

Structure: R²-N(R¹)-C(=O)-CH₂-O-S(=O)₂-NHR³

| R¹ | R² | R³ |
|---|---|---|
| CH₃ | 3-chlorophenyl | CH₃ |
| CH₃ | 2-methoxyphenyl | CH₃ |
| CH₃ | 4-methoxyphenyl | CH₃ |
| CH₃ | 4-methylphenyl | CH₃ |
| CH₃ | 3-chlorophenyl | C₂H₅ |
| CH₃ | 2-methylphenyl | C₂H₅ |
| CH₃ | 4-methoxyphenyl | C₂H₅ |
| CH₃ | 4-methylphenyl | C₂H₅ |
| CH₃ | 3-chlorophenyl | i-C₃H₇ |
| CH₃ | 2-methylphenyl | i-C₃H₇ |
| CH₃ | 4-methylphenyl | i-C₃H₇ |
| CH₃ | 4-methoxyphenyl | i-C₃H₇ |
| CH₃ | 2,4-dimethylphenyl | i-C₃H₇ |
| C₂H₅ | 3,5-dimethylphenyl | CH₃ |
| C₂H₅ | 3-methylphenyl | C₂H₅ |

-continued

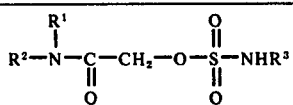

| R¹ | R² | R³ |
|---|---|---|
| $C_2H_5$ | 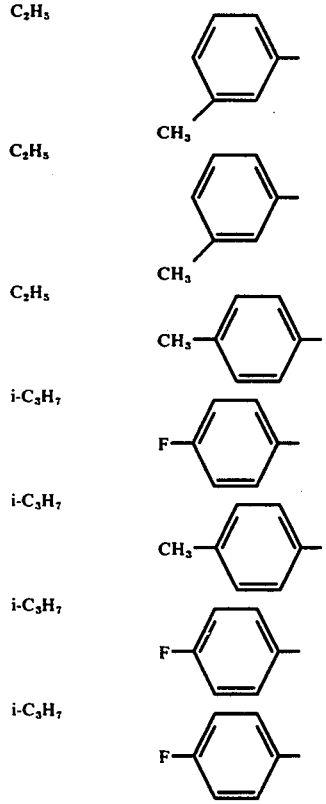 3-methylphenyl | n-$C_3H_7$ |
| $C_2H_5$ | 3-methylphenyl | i-$C_3H_7$ |
| $C_2H_5$ | 4-methylphenyl | i-$C_3H_7$ |
| i-$C_3H_7$ | 4-fluorophenyl | $CH_3$ |
| i-$C_3H_7$ | 4-methylphenyl | $CH_3$ |
| i-$C_3H_7$ | 4-fluorophenyl | $C_2H_5$ |
| i-$C_3H_7$ | 4-fluorophenyl | n-$C_3H_7$ |

-continued

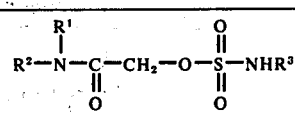

| R¹ | R² | R³ |
|---|---|---|
| i-$C_3H_7$ | 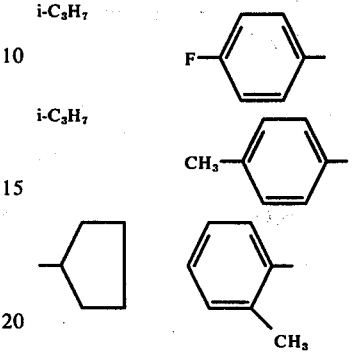 4-fluorophenyl | i-$C_3H_7$ |
| i-$C_3H_7$ | 4-methylphenyl | i-$C_3H_7$ |
| | cyclopentyl, 2-methylphenyl | i-$C_3H_7$ |

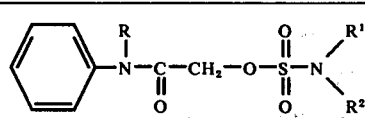

| R | R¹ | R² |
|---|---|---|
| $CH_3$ | $CH_3$ | $CH_3$ |
| $C_2H_5$ | $CH_3$ | $CH_3$ |
| i-$C_3H_7$ | $CH_3$ | $CH_3$ |
| i-$C_3H_7$ | $C_2H_5$ | $C_2H_5$ |
| i-$C_3H_7$ | $CH_3$ | $CH_2CH_2Cl$ |
| sec-$C_4H_9$ | $CH_3$ | $CH_3$ |

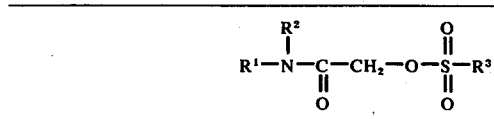

| R¹ | R² | R³ |
|---|---|---|
| 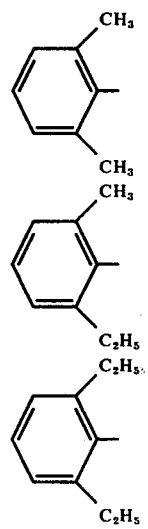 2,6-dimethylphenyl | $-CH_2OCH_3$ | $CH_3$ |
| 2-methyl-6-ethylphenyl | $-CH_2OCH_3$ | $CH_3$ |
| 2,6-diethylphenyl | $CH_2OCH_3$ | $CH_3$ |

-continued $$R^1-N(R^2)-C(=O)-CH_2-O-S(=O)_2-R^3$$

| R¹ | R² | R³ |
|---|---|---|
| 2,6-di(C₂H₅)-phenyl | CH₂OCH₃ | CH₂Cl |
| 2,6-di(C₂H₅)-phenyl | CH₂OCH₃ | C₂H₅ |
| 2,6-di(C₂H₅)-phenyl | CH₂OCH₃ | i-C₃H₇ |
| 2,6-di(CH(CH₃)₂)-phenyl | CH₂OCH₃ | CH₃ |
| 2,6-di(CH(CH₃)₂)-phenyl | CH₂OCH₃ | C₂H₅ |
| 2,6-di(CH₃)-phenyl | CH₂OC₂H₅ | CH₃ |
| 2-CH₃-6-C₂H₅-phenyl | CH₂OC₂H₅ | CH₃ |
| 2-CH₃-6-C₂H₅-phenyl | CH₂OC₂H₅ | C₂H₅ |
| 2,6-di(C₂H₅)-phenyl | CH₂OC₂H₅ | CH₃ |

-continued $$R^1-N(R^2)-C(=O)-CH_2-O-S(=O)_2-R^3$$

| R¹ | R² | R³ |
|---|---|---|
| 2,3-dimethylphenyl | CH₂OC₃H₇ | CH₃ |
| 2,3-dimethylphenyl | CH₂OC₃H₇ | C₂H₅ |
| 2,3-dimethylphenyl | CH₂OCH(CH₃)₂ | C₂H₅ |
| 2,3-dimethylphenyl | —CH₂OCH₂CH=CH₂ | CH₃ |
| 2-methyl-3-ethylphenyl | —CH₂OC₂H₅ | C₃H₇i |
| 2-methyl-3-ethylphenyl | —CH₂OC₂H₅ | —CH₂—CH(CH₃)₂ |
| 2,3-dimethylphenyl | —CH₂—O—CH₂—C≡CH | CH₃ |
| 2,3-dimethylphenyl | —CH₂O—CH(CH₃)—C₂H₅ | CH₃ |
| 2,3-dimethylphenyl | —CH₂O—CH(CH₃)—C₂H₅ | C₂H₅ |

-continued $$R^1-N(R^2)-\underset{O}{\underset{\|}{C}}-CH_2-O-\underset{O}{\overset{O}{\underset{\|}{\overset{\|}{S}}}}-R^3$$

| R¹ | R² | R³ |
|---|---|---|
| 2,6-(CH₃)₂-C₆H₃ | CHOCH(CH₃)₂ | CH₃ |
| 2,6-(CH₃)₂-C₆H₃ | CH₂OC₃H₇ | CH₃ |
| 2-CH₃-6-C₂H₅-C₆H₃ | CHOCH(CH₃)₂ | CH₃ |
| 2-CH₃-6-C₂H₅-C₆H₃ | CH₂OC₃H₇ | CH₃ |
| 2,6-(C₂H₅)₂-C₆H₃ | CH₂OCH(CH₃)₂ | CH₃ |
| 2,6-(C₂H₅)₂-C₆H₃ | CH₂OCH₂CH(CH₃)₂ | CH₃ |
| 2,6-(C₂H₅)₂-C₆H₃ | CH₂OCH₂CH=CH₂ | CH₃ |

(R¹ shown as 2,6-dialkyl-substituted phenyl rings in original)

$$(CH_2)_n\text{N}-\underset{O}{\underset{\|}{C}}-CH_2-O-\underset{O}{\overset{O}{\underset{\|}{\overset{\|}{S}}}}-NH-R$$

| R | n |
|---|---|
| CH₃ | 4 |
| C₂H₅ | 4 |
| CH₂CH₂Cl | 4 |
| i-C₃H₇ | 4 |
| n-C₃H₇ | 4 |
| n-C₄H₉ | 4 |
| sec.-C₄H₉ | 4 |
| i-C₄H₉ | 4 |
| CH₃ | 5 |
| C₂H₅ | 5 |
| n-C₃H₇ | 5 |
| i-C₃H₇ | 5 |
| n-C₄H₉ | 5 |

-continued $$(CH_2)_n\text{N}-\underset{O}{\underset{\|}{C}}-CH_2-O-\underset{O}{\overset{O}{\underset{\|}{\overset{\|}{S}}}}-NH-R$$

| R | n |
|---|---|
| CH₃ | 6 |
| C₂H₅ | 6 |
| CH₂CH₂Cl | 6 |
| n-C₃H₇ | 6 |
| i-C₃H₇ | 6 |
| n-C₄H₉ | 6 |
| sec.-C₄H₉ | 6 |
| —CH(C₂H₅)₂ | 6 |
| CH₂CH(CH₃)C₂H₅ | 6 |
| CH₃ | 7 |
| —C₂H₅ | 7 |

-continued

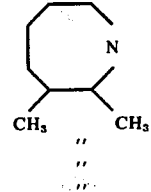

| R | n | |
|---|---|---|
| —CH₂—CH₂Cl | 7 | |
| n-C₃H₇ | 7 | |
| i-C₃H₇ | 7 | |
| H | 8 | (bicyclo) |
| CH₃ | 8 | " |
| C₂H₅ | 8 | " |
| i-C₃H₇ | 8 | " |
| n-C₃H₇ | 8 | " |
| n-C₄H₉ | 8 | " |
| sec.-C₄H₉ | 8 | " |
| i-C₄H₉ | 8 | " |

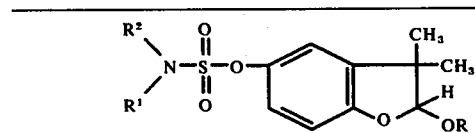

| R | R¹ | R² |
|---|---|---|
| H | H | i-C₃H₇ |
| CH₃ | CH₃ | H |
| CH₃ | i-C₃H₇ | H |
| CH₃ | n-C₃H₇ | H |
| C₂H₅ | CH₃ | H |
| C₂H₅ | C₂H₅ | H |
| C₂H₅ | i-C₃H₇ | H |
| CH₂CH₂Cl | CH₃ | H |
| n-C₃H₇ | CH₃ | H |
| n-C₃H₇ | C₂H₅ | H |
| n-C₃H₇ | n-C₃H₇ | H |
| i-C₃H₇ | CH₃ | H |
| i-C₃H₇ | C₂H₅ | H |
| i-C₃H₇ | n-C₃H₇ | H |
| CH₂CH=CH₂ | CH₃ | H |
| CH₂C≡CH | CH₃ | H |
| H | C₂H₅ | C₂H₅ |
| CH₃ | CH₃ | CH₃ |
| CH₃ | CH₃ | C₂H₅ |
| CH₃ | C₂H₅ | C₂H₅ |
| C₂H₅ | CH₃ | CH₃ |
| CH₂CH₂Cl | CH₂ | CH₃ |
| CH₂CH₂OCH₃ | CH₃ | CH₃ |
| C₂H₅ | CH₃ | CH₂CH=CH₂ |
| C₂H₅ | C₂H₅ | C₂H₅ |
| n-C₃H₇ | CH₃ | CH₃ |
| i-C₃H₇ | CH₃ | CH₃ |
| CH₂CH=CH₂ | CH₃ | CH₃ |
| CH₂CH=CH₂ | C₂H₅ | C₂H₅ |
| CH₃ | H | H |
| C₂H₅ | H | H |
| —CO—CH₃ | CH₃ | CH₃ |
| —CO—CH₂Cl | CH₃ | CH₃ |
| —CO—CH₂Cl | C₂H₅ | C₂H₅ |
| C₂H₅ | CH₃ | CH₂—C≡CH |
| C₂H₅ | CH₃ | Na |
| —CO—CH₃ | CH₃ | —CO—CH₃ |
| —CO—C₂H₅ | CH₃ | CH₃ |
| —CO—OCH₃ | CH₃ | CH₃ |
| —CO—OC₂H₅ | CH₃ | CH₃ |
| CH₃ | CH₃ | —CO—CH₃ |
| CH₃ | CH₃ | —CO—CH₂Cl |
| C₂H₅ | CH₃ | —CO—CH₃ |
| C₂H₅ | CH₃ | —CO—CH₂Cl |
| C₂H₅ | C₂H₅ | —O—CO—CH₃ |
| C₂H₅ | CH₃ | —CO—CHCl₂ |
| C₂H₅ | CH₃ | —CO—OCH₃ |
| C₂H₅ | CH₃ | —CO—OC₂H₅ |
| C₂H₅ | CH₃ | —CO—O—CH(CH₃)₂ |
| —CO—OCH₃ | C₂H₅ | C₂H₅ |

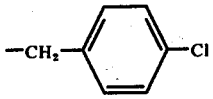

| R¹ | R² |
|---|---|
| 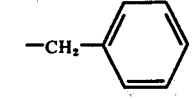 | CH₃ |
| " | C₂H₅ |
| " | n-C₃H₇ |
| " | —CH₂—C₆H₄—Cl |
| " | —CH₂—C₆H₅ |

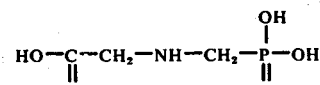

| R¹ | R² | X | Y |
|---|---|---|---|
| Cl | Na | Cl | Cl |
| CH₃ | Na | Cl | Cl |
| CH₂Cl | Na | Cl | Cl |
| CH₃ | CH₂—C₆H₅ | Cl | Cl |
| C₂H₅ | Na | Cl | Cl |
| CHF₂ | Na | F | F |
| CH₃ | CH₂CH₂Cl | Cl | Cl |
| CH₃ | 4-Cl-C₆H₄-CH₂ | H | Cl |
| C₆H₅—CO—NHO | H (salts, esters) | H | H |
| C₆H₅CHCl | NH₄ | H | Cl |

$$HO-\underset{\underset{O}{\|}}{C}-CH_2-NH-CH_2-\underset{\underset{O}{\|}}{P}(OH)_2$$

and salts of the compound

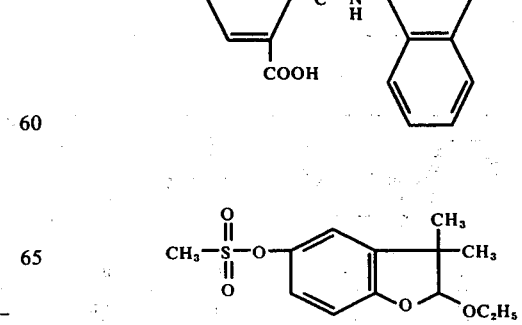

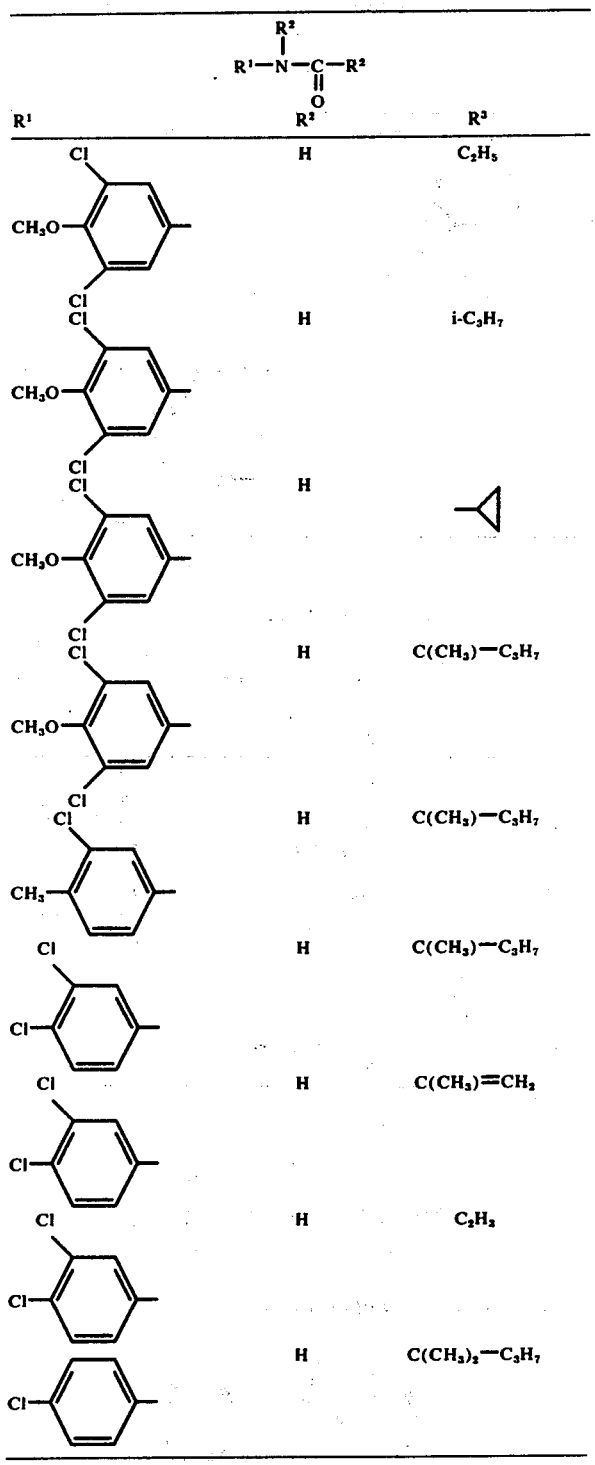

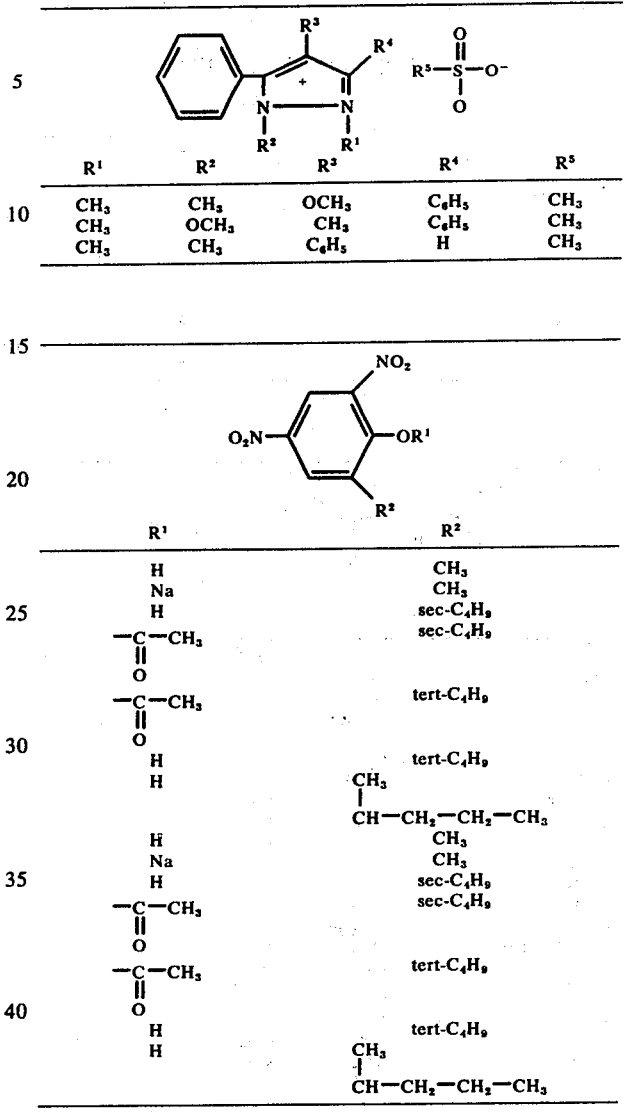

In addition to the foregoing active ingredients there may also be used sulfurous esters of glycolic amides, azetidine carbothiolates and butynyl carbamates as components of the compositions.

The sulfurous esters of glycolic amides (b) may be obtained be reacting a glycolic amide with an alkyl chlorosulfinate in an inert solvent, in the presence of an agent which binds hydrogen chloride and at from 10° to 15° C.

For instance, O-ethyl-O-(1-carbonylmethyl)-azacycloheptane sulfite may be prepared by dripping a solution of 12.9 parts by weight of ethyl chlorosulfinate in 50 parts by weight of benzene at 10° to 15° C into 15.7 parts by weight of glycolic acid hexamethylene amide dissolved together with 8 parts by weight of pyridine in 50 parts by weight of dry benzene. After 30 minutes the pyridinium hydrochloride which has precipitated out is removed by suction filtration and the organic phase washed with water. After drying has been carried out, the benzene is distilled off. There is obtained 20.4 parts by weight of the desired product having the following structure:

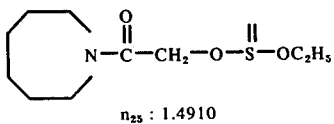

$n_{25} : 1.4910$

The following compounds are further examples:
N-methylacetanilido-(α-ethylsulfite)
N-methylacetanilido-(α-isopropylsulfite)
N-(butyn-1-yl-3)-acetanilido-(α-ethylsulfite)
N-(butyn-1-yl-3)-acetanilido-(α-isopropylsulfite)
N-(butyn-1-yl-3)-acetanilido-(α-methylsulfite) m.p.: 69° to 70° C
N-isopropylacetanilido-(α-methylsulfite) m.p.: 60° to 61° C
N-isopropylacetanilido-(α-isopropylsulfite) m.p.: 52° to 53° C
N-ethylacetanilido-(α-propylsulfite) $n_{25}^D$: 1.5295
N-ethylacetanilido-(α-isopropylsulfite) $n_{25}^D$: 1.5164
N-ethylacetanilido-(α-methylsulfite) $n_{25}^D$: 1.5118
N-ethylacetanilido-(α-ethylsulfite) $n_{25}^D$: 1.5010
N-methyl-(4-methoxyacetanilido)-(α-isopropylsulfite)
N-(butyn-1-yl-3)-(4-methoxyacetanilido)-(α-isopropylsulfite)
N-methyl-(p-methylacetanilido)-(α-isopropylsulfite)
N-butyn-1-yl-3)-(p-methylacetanilido)-(α-isopropylsulfite)
N-(2-methylbenzyl)-acetanilido-(α-methylsulfite)
N-(2-methylbenzyl)-acetanilido-(α-ethylsulfite)
N-(2-methylbenzyl)-acetanilido-(α-propylsulfite)
N-(2-methylbenzyl)-acetanilido-(α-isopropylsulfite)
N-tert-butylacetanilido-(α-isopropylsulfite) m.p.: 78° C
N-tert-butylacetanilido-(α-methylsulfite) m.p.: 57° C
N-(butyn-1-yl-3)-acetanilido-(α-isobutylsulfite) $n_{25}$: 1.5098
N-(butyn-1-yl-3)-acetanilido-(α-sec-butylsulfite) $n_{25}$: 1.5132
N-(butyn-1-yl-3)-acetanilido-(α-n-butylsulfite) $n_{25}$: 1.5172
N-isobutylacetanilido-(α-methylsulfite) $n_{25}$: 1.5229
N-isobutylacetanilido-(α-ethylsulfite) $n_{25}$: 1.5100
N-methylacetanilido-(α-n-butylsulfite) $n_{25}$: 1.5144
N-isobutylacetanilido-(α-propylsulfite) $n_{25}$: 1.5059
N-isobutylacetanilido-(α-isopropylsulfite) $n_{25}$: 1.5028
N-methylacetanilido-(α-methylsulfite)
N-methylacetanilido-(α-isobutylsulfite)
N-(butyn-1-yl-3)-acetanilido-(α-methylsulfite)
N-methyl-(2-methylacetanilido)-(α-methylsulfite)
N-methyl-(4-methylacetanilido)-(α-methylsulfite)
N-methyl-(4-methoxyacetanilido)-(α-methylsulfite)
N-methyl-(3-chloroacetanilido)-(α-methylsulfite)
N-methyl-(2-methylacetanilido)-(α-ethylsulfite)
N-methyl-(4-methylacetanilido)-(α-ethylsulfite)
N-methyl-acetanilido-[α-(1-methyl-2-methoxy)-ethylsulfite]
N-methyl-(4-methoxyacetanilido)-(α-ethylsulfite)
N-methyl-(3-chloroacetanilido)-(α-ethylsulfite)
N-methyl-(2-methylacetanilido)-(α-isopropylsulfite)
N-methyl-(3-chloroacetanilido)-(α-isopropylsulfite)
N-methyl-(4-methylacetanilido)-(α-n-butylsulfite)
O-methyl-O-(1-carbonylmethylazacycloheptane)-sulfite; $n_{25}$: 1.4955
O-isopropyl-O-(1-carbonylmethylazacycloheptane)-sulfite; $n_{25}$: 1.4695
O-butyl-O-(1-carbonylmethylazacycloheptane)-sulfite; $n_{25}$: 1.4875
O-propyl-O-(1-carbonylmethylazacyclopentane)-sulfite; $n_{25}$: 1.4828
O-isopropyl-O-(1-carbonylmethylazacyclopentane)-sulfite; m.p.: 58°–59° C
O-ethyl-O-(1-carbonylmethyl-2-methylazacycloheptane)-sulfite; $n_{25}$: 1.4882
O-isopropyl-O-(1-carbonylmethyl-2-methylazacycloheptane)-sulfite; $n_{25}$: 1,4740
O-methyl-O-(1-carbonylmethyl-2,3-dimethylazacycloheptane)-sulfite; $n_{25}$: 1.4952
O-ethyl-O-(1-carbonylmethyl-2,3-dimethylazacycloheptane)-sulfite; $n_{25}$: 1.4860
O-propyl-O-(1-carbonylmethyl-2,3-dimethylazacycloheptane)-sulfite; $n_{25}$: 1.4849
O-isopropyl-O-(1carbonylmethyl-2,3-dimethylazacycloheptane)-sulfite; $n_{25}$: 1.4749
O-ethyl-O-(1-carbonylmethyl-3,5,5-trimethyl-(3,3,5-trimethyl)-azacycloheptane)-sulfite; $n_{25}$: 1.4850
(1:1 isomer mixture of the 3,3,5- and 3,3,5-trimethyl derivative)
O-isopropyl-O-(1-carbonylmethyl-3-methyl-(2-methyl)-azacycloheptane)-sulfite; $n_{25}$: 1.4735
(isomer mixture consisting of 55% of the 3-methyl- and 45% of the 2-methyl derivative)
O-ethyl-O-(1-carbonylmethylazacycloheptane)-sulfite
O-n-propyl-O-(1-carbonylmethylazacycloheptane)-sulfite
O-methyl-O-(1-carbonylmethyl-3-methylazacycloheptane)-sulfite
O-ethyl-O-(1-carbonylmethyl-3-methylazacycloheptane)-sulfite
O-isopropyl-O-(1-carbonylmethyl-3-methylazacycloheptane)-sulfite
O-ethyl-O-(1-carbonylmethyl-4-methylazacycloheptane)-sulfite
O-isopropyl-O-(1-carbonylmethyl-4-methylazacycloheptane)-sulfite
O-methyl-(1-carbonylmethyl-3-azabicyclo-[3,2,0]-heptane)-sulfite
O-ethyl-(1-carbonylmethyl-3-azabicyclo-[3,2,0]-heptane)-sulfite
O-n-propyl-(1-carbonylmethyl-3-azabicyclo-[3,2,0]-heptane)-sulfite
O-isopropyl-(1-carbonylmethyl-3-azabicyclo-[3,2,0]-heptane)-sulfite
O-isopropyl-O-(1-carbonylmethyl-2-methyl-(3-methyl)-azacyclo-heptane)-sulfite; $n_{25}$: 1.4698
(isomer mixture consisting of 75% of the 2-methyl- and 25% of the 3-methyl derivative)
O-allyl-O-(1-carbonylmethyl-2,3-dimethylazacycloheptane)-sulfite $n_{25}$: 1.4970
O-allyl-O-(1-carbonylmethylazacycloheptane)-sulfite; $n_{25}$: 1.5026
O-butyn-1-yl-3)-O-(1-carbonylmethyl-2,3-dimethylazacycloheptane)-sulfite; $n_{25}$: 1.4929
O-butyn-1-yl-3)-O-(1-carbonylmethyl-3-methylazacycloheptane)-sulfite; $n_{25}$: 1.4965
O-ethyl-O-(1-carbonylmethylazacyclohexane)-sulfite
O-isopropyl-O-(1-carbonylmethylazacyclohexane)-sulfite
O-methyl-O-(1-carbonylmethyl-2-methylazacyclohexane)-sulfite O-allyl-O-(1-carbonylmethyl-2-methylazacyclohexane)-sulfite
O-isopropyl-O-(1-carbonylmethyl-2-methylazacyclohexane)-sulfite
O-isopropyl-O-(1-carbonylmethyl-3-methylazacyclohexane)-sulfite
O-(β-chloroethyl)-O-(1-carbonylmethyl-3-methylazacyclohexane)-sulfite
O-ethyl-O-(1-carbonylmethyl-4-methylazacyclohexane)-sulfite
O-allyl-O-(1-carbonylmethyl-4-methylazacyclohexane)-sulfite
O-(β-chloroethyl)-O-(1-carbonylmethyl-4-methylazacyclohexane)-sulfite
O-methyl-O-(1-carbonylmethyl-3,3-dimethylazacyclohexane)-sulfite
O-isopropyl-O-(1-carbonylmethyl-3,3-dimethylazacyclohexane)-sulfite
O-(β-chloroethyl)-O-(1-carbonylmethyl-3,5,5-trimethyl)-(3,3,5-trimethylazacycloheptane)-sulfite
(1:1 isomer mixture of the 3,5,5- and 3,3,5-trimethyl derivative)

Hexahydroazetidine carbothiolates may be prepared by reacting a thiol chloroformate with an optionally substituted azetidine. They may also be prepared by reacting azetidines in the form of their N-acyl chlorides with mercaptans. For instance, S-ethyl-(2,2,4-trimethylazetidine)-1-carbothiolate is obtained by dripping, at 30° to 40° C, 6.23 parts by weight of thioethyl chloroformate into a mixture of 4.95 parts by weight of 2,2,4-trimethylazetidine and 6 parts by weight of triethylamine in 50 parts by weight of benzene. After one hour the triethylamine hydrochloride is filtered off and the filtrate washed with water. After drying, concentration is carried out in vacuo and the residue distilled off. There is obtained 6.7 parts by weight of the desired compound having the following formula:

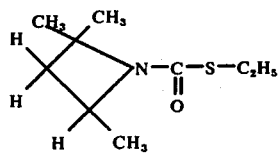

b.p. (0.01 mm): 59° C.

Suitable azetidine carbothiolates are listed below:
S-methyl-(2,2,4-trimethylazetidine)-1-carbothiolate, b.p. (0.05 mm): 70° C
S-propyl-(2,2,4-trimethylazetidine)-1-carbothiolate, b.p. (0.05 mm): 81° C
S-isopropyl-(2,2,4-trimethylazetidine)-1-carbothiolate, b.p. (0.01 mm): 67° to 71° C
S-sec-butyl-(2,2,4-trimethylazetidine)-1-carbothiolate, b.p. (0.01 mm): 75° to 80° C
S-trichloroallyl-(2,2,4-trimethylazetidine)-1-carbothiolate, b.p. (0.01 mm): 130° C
S-benzyl-(2,2,4-trimethylazetidine)-1-carbothiolate, b.p. (0.01 mm): 135° C
S-(p-chlorobenzyl)-2,2,4-trimethylazetidine)-1-carbothiolate, b.p. (0.05 mm): 154° C
S-benzyl-(3,3-dimethylazetidine)-1-carbothiolate, b.p. (0.01 mm): 128° C
S-(β-phenylethyl)-(2,2,4-trimethylazetidine)-1-carbothiolate, b.p. (0.01 mm): 120° to 125° C, $n_{20}$: 1.5398
S-(β-phenylethyl)-(3,3-dimethylazetidine)-1-carbothiolate, b.p. (0.01 mm): 140° to 145° C, $n_{20}$: 1.5996
S-benzyl-(2,2,4-trimethylazetidine)-1-thiocarbothiolate, b.p. (0.01 mm); 160° C, $n_{25}$: 1.6026
S-propyl-(2,2,4-trimethylazetidine)-1-thiocarbothiolate, b.p. (0.01 mm): 100° C, $n_{25}$: 1.5540
S-benzylazetidine-1-carbothiolate
S-ethylazetidine-1-carbothiolate
S-ethyl-(2,2,4-trimethylazetidine)-1-carbothiolate
S-2,3-dichloroallyl-(2,2,4-trimethylazetidine)-1-carbothiolate
S-4-methoxybenzyl-(2,2,4-trimethylazetidine)-1-carbothiolate
S-propylazetidine-1-carbothiolate
S-isopropylazetidine-1-carbothiolate
S-benzyl-(2-methylazetidine)-1-carbothiolate
S-butyl-(2,2,4-trimethylazetidine)-1-carbothiolate, b.p. (0.01 mm): 90° to 95° C, $n_{20}$: 1.4835
S-propyl-(2,2,4-trimethylazetidine)-1-thiocarbothiolate.

The substituted butynyl carbamates may be prepared by reaction of a 4-hydroxybutyn-2-yl carbamate with an aminosulfonyl halide. For instance, 4-methylaminosulfonyloxybutyn-1-yl-N-(3-chlorophenyl)-carbamate is obtained by adding, at 0° to +5° C and while stirring, 20.8 parts by weight of methylaminosulfonyl chloride (about 90%) simultaneously with 16.6 parts by weight of triethylamine to a solution of 23.95 parts by weight of 4-hydroxybutyn-2-yl-N-(3-chlorophenyl)-carbamate in 650 parts by weight of methylene chloride. 30 minutes after completion of the reaction the mixture is successively treated with ice water, dilute aqueous hydrochloric acid, water, sodium bicarbonate solution and again with water. The methylene chloride solution is dried with magnesium sulfate and concentrated; there is obtained 33 parts of crude product melting at from 99° to 102° C.

After recrystallization from a mixture of 1,2-dichloroethane and benzene the compound melts at from 103° to 105° C.

The compound has the following formula:

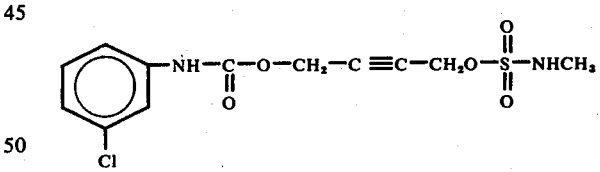

Examples of compounds from this class are as follows:
4-aminosulfonyloxybutyn-2-yl-N-(3-chlorophenyl)-carbamate
4-methylaminosulfonyloxybutyn-2-yl-N-(3-chlorophenyl)-carbamate
4-ethylaminosulfonyloxybutyn-2-yl-N-(3-chlorophenyl)-carbamate
4-propylaminosulfonyloxybutyn-2-yl-N-(3-chlorophenyl)-carbamate
4-isopropylaminosulfonyloxybutyn-2-yl-N-(3-chlorophenyl)-carbamate
4-(2-chloroethylaminosulfonyloxy)-butyn-2-yl-N-(3-chlorophenyl)-carbamate
4-aminosulfonyloxybutyn-2-yl-N-(3-trifluoromethylphenyl)-carbamate 4-methylaminosulfonyloxybutyn-2-yl-N-(3-tri-fluoromethylphenyl)-carbamate
4-ethylaminosulfonyloxybutyn-2-yl-N-(3-tri-fluoromethylphenyl)-carbamate
4-propylaminosulfonyloxybutyn-2-yl-N-(3-tri-fluoromethylphenyl)-carbamate
4-isopropylaminosulfonyloxybutyn-2-yl-N-(3-tri-fluoromethylphenyl)-carbamate
4-(2-chloroethylaminosulfonyloxy)-butyn-2-yl-N-(3-trifluoromethylphenyl)-carbamate
4-methylaminosulfonyloxybutyn-2-yl-N-phenyl carbamate
4-methylaminosulfonyloxybutyn-2-yl-N-(3-bromophenyl)-carbamate
4-methylaminosulfonyloxybutyn-2-yl-N-(3,4-dichlorophenyl)-carbamate
4-methylaminosulfonyloxybutyn-2-yl-N-(3-methylphenyl)-carbamate
4-methylaminosulfonyloxybutyn-2-yl-N-(3-methoxyphenyl)-carbamate.

The amount of any one component in the active ingredient compositions as such may vary from 5 to 95 wt%, preferably from 20 to 80 wt%, based on the composition.

The amount used of the agents according to the invention may vary and depends in essence on the type of effect to be achieved; it is generally from 0.1 to 15 (and more), preferably from 0.2 to 6, kg per hectare of active ingredient. The agents according to the invention may be used once or several times before or after planting, before sowing, and before, during or after emergence of the crop plants and unwanted plants.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepared emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutyl-naphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphtalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methylcellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 1 to 99, and preferably 1 to 90% by weight of active ingredient composition.

There may be added to the compositions or individual active ingredients (if desired, immediately before use (tankmix)) oils of various types, herbicides, fungicides, nematocides, insecticides, bactericides, trace elements, fertilizers, antifoams (e.g., silicones), growth regulators, antidotes and other herbicidally effective compounds such as
substituted anilines
substituted aryloxycarboxylic acids and salts, esters and amides thereof,
substituted ethers
substituted arsonic acids and their salts, ester and amides
substituted benzimidazoles
substituted benzisothiazoles
substituted benzothiadiazinone dioxides
substituted benzoxazines
substituted benzoxazinones
substituted benzothiadiazoles
substituted biurets
substituted quinolines
substituted carbamates
substituted aliphatic carboxylic acids and their salts, esters and amides
substituted aromatic carboxylic acids and their salts, esters and amides
substituted carbamoylalkylthiol- or -dithiophosphates
substituted quinazolines
substituted cycloalkylamidocarbothiolic acids and their salts, esters and amides
substituted cycloalkylcarbonamidothiazoles
substituted dicarboxylic acids and their salts, esters and amides substituted dihyrobenzofuranyl sulfonates
substituted disulfides
substituted dipyridylium salts
substituted dithiocarbamates
substituted dithiophosphoric acids and their salts, ester and amides
substituted ureas
substituted hexahydro-1H-carbothioates
substituted hydantoins
substituted hydrazides
substituted hydrazonium salts
substituted isoxazole pyrimidones
substituted imidazoles
substituted isothiazole pyrimidones
substituted ketones
substituted naphthoquinones
substituted aliphatic nitriles
substituted aromatic nitriles
substituted oxadiazoles
substituted oxadiazinones
substituted oxadiazolidine diones
substituted oxadiazine diones
substituted phenols and their salts and esters
substituted phosphonic acids and their salts, esters and amides
substituted phosphonium chlorides
substituted phosphonalkyl glycines
substituted phosphites
substituted phosphoric acid and their salts, esters and amides
substituted piperidines
substituted pyrazoles
substituted pyrazole alkylcarboxylic acids and their salts, esters and amides
substituted pyrazolium salts
substituted pyrazolium alkyl sulfates
substituted pyridazines
substituted pyridazones
substituted pyridine carboxylic acids and their salts, esters and amides
substituted pyridines
substituted pyridine carboxylates
substituted pyridinones
substituted pyrimidines
substituted pyrmindones
substituted pyrrolidine carboxylic acid and its salts, esters and amides
substituted pyrrolidines
substituted pyrrolidones
substituted arylsulfonic acids and their salts, esters and amides
substituted styrenes
substituted tetrahydrooxadiazine diones
substituted tetrahydroxadiazole diones
substituted tetrahydromethanoindenes
substituted tetrahydroxadiazole thiones
substituted tetrahydrothiadiazine thiones
substituted tetrahydrothiadiazole diones
substituted aromatic thiocarbonylamides
substituted thiocarboxylic acids and their salts, esters and amides
substituted thiol carbamates
substituted thioureas
substituted thiophosphoric acids and their salts, esters and amides
substituted triazines
substituted triazoles
substituted uracils, and
substituted uretidine diones.

The last-mentioned herbicidal compounds may also be applied before or after the individual active ingredients or compositions thereof according to the invention.

These agents may be added to the herbicides according to the invention in a ratio by weight of from 1:10 to 10:1. The same applies to oils, fungicides, nematocides, insecticides, bactericides, antidotes and growth regulators.

The new compositions have strong herbicidal action and may therefore be used as weedkillers or for controlling the growth of unwanted plants. Whether the new active ingredients are used as total or selective agents depends in essence on the amount of ingredient used per unit area.

By weeds and unwanted plant growth are meant all monocotyledonous and dicotyledonous plants which grow in loci where they are not desired.

The agents according to the invention may be used for controlling for instance

Gramineae, such as

Cynodon spp. Digitaria spp. Echinochloa spp. Setaria spp. Panicum spp. Alopecurus spp. Lolium spp. Dactylis spp. Avena spp. Bromus spp. Uniola spp. Poa spp. Leptochloa spp. Brachiaria spp.

Sorghum spp. Agropyron spp. Phalaris spp. Apera spp. Eleusine spp. Cenchrus spp. Eragrostis spp. *Phragmites communis* etc;

Cyperaceae, such as

Carex spp. Cyperus spp. Eleocharis spp. Scirpus spp. etc.;

dicotyledonous weeds, such as
Malvaceae, e.g.,

Abutilon theoprasti Sida spp. Hibiscus spp. Malva spp. etc.;

Compositae, such as

Ambrosia spp. Lactuca spp. Senecio spp. Sonchus spp. Xanthium spp. Iva spp. Galinsoga spp. Taraxacum spp. Chrysanthemum spp. Cirsium spp. Centaurea spp. Tussilago spp. *Lapsana communis* Tagetes spp. Erigeron spp. Anthemis spp. Matricaria spp. Artemisia spp. Bidens spp. etc.;

Convolvulaceae, such as
Convolvulus spp. Ipomoea spp. Cuscuta spp. *Jaquemontia tamnifolia* etc.;

Cruciferae, such as
Barbarea vulgaris Brassica spp. Capsella spp. Arabidopsis thaliana Descurainia spp. Draba spp.
Sisymbrium spp. Thlaspi spp. *Sinapis arvensis* *Coronopus didymus* Lepidium spp. Raphanus spp. etc.;

Geraniaceae, such as
Erodium spp. Geranium spp. etc.;

Portulacaceae, such as
Portulaca spp. etc.;

Primulaceae, such as

*Anagallis arvensis*
Lysimachia spp. etc.;

Rubiaceae, such as
Richardia spp. Galium spp. Diodia spp. etc.;

Scrophulariaceae, such as
Linaria spp. Veronica spp. Digitalis spp. etc.;

Solanaceae, such as
Physalis spp. Solanum spp. Nicandra spp. Datura spp. etc.;

Urticaceae, such as
Urtica spp.

Violaceae, such as
Viola spp. etc.;

Zygophyllaceae, such as
*Tribulus terrestris* etc.;

Euphorbiaceae, such as
Mercurialis annua Euphorbia spp.

Umbelliferae, such as
Daucus carota Aethusa cynapium Ammi majus etc.;

Commelinaceae, such as
Commelina spp. etc.;

Labiatae, such as
Lamium spp. Galeopsis spp. etc.;

Leguminosae, such as
Medicago spp. Trifolium spp. Vicia spp. Sesbania exaltata Cassia spp. Lathyrus spp. etc.;

Plantaginaceae, such as
Plantago spp. etc. ;

Polygonaceae, such as
Polygonum spp. Rumex spp. Fagopyrum spp. etc.;

Aizoaceae, such as
*Mollugo verticillate* etc.;

Amaranthaceae, such as
Amaranthus spp. etc.;

Boraginaceae, such as
Amsinckia spp. Myostis spp. Anchusa spp. Lithospermum spp. etc.;

Caryophyllaceae, such as
Stellaria spp. Spergula spp. Saponaria spp. *Scleranthus annuus* Silene spp. Cerastium spp. *Agrostemma githago* etc.;

Chenopodiaceae, such as
Chenopodium spp. Kochia spp. Salsola Kali Atriplex spp. *Monolepsis nuttalliana* etc.;

Lythraceae, such as
Cuphea spp. etc.;

Oxalidaceae, such as
Oxalis spp.

Ranunculaceae, such as
Ranunculus spp. Delphinium spp. Adonis spp. etc,;

Papaveraceae, such as
Papaver spp. *Fumaria offinicalis* etc.;

Onagraceae, such as
Jussiaea spp. etc.;

Rosaceae, such as
Alchemillia spp. Potentilla spp. etc.;

Potamogetonaceae, such as
Potamogeton spp. etc.;

Najadaceae, such as
Najas spp. etc.;

Equisetaceae
Equisetum spp. etc.;

Marsileaceae, such as
*Marsilea quadrifolia* etc;

Polypodiaceae,
*Pteridium quilinum*

Alismataceae, such as
Alisma spp. *Sagittaria sagittifolia* etc.

The herbicides according to the invention may be employed in cereal crops such as
Avena spp. Triticum spp. Hordeum spp. Secale spp. *Saccharum offinicarum* Sorghum Zea mays *Panicum miliaceum Oryza spp.* and in dicotyledon crops such as

Cruciferae, e.g.
Brassica spp. Sinapis spp. Raphanus spp. Lepidium spp.

Compositae, e.g.
Lactuca spp. Helianthus spp. Carthamus spp. Scorzonera spp.

Malvaceae, e.g.
Gossypium hirsutum

Leguminosae, e.g.
Medicago spp. Trifolium spp. Pisum spp. Phaseolus spp. Arachis spp. Glycine max.

Chenopodiaceae, e.g.
*Beta vulgaris Spinacia spp.*

Solanaceae, e.g.
Solanum spp. Nicotiania spp. *Capsicum annuum*

Linaceae, e.g. Linum spp.

Umbelliferae, e.g. Petroselinum spp. *Apium graveolens Apium Daucus carota*

Rosaceae, e.g.
Fragaria

Cucurbitaceae e.g.

Cucumis spp. Cucurbita spp.

Liliaceae, e.g.
Allium spp.

Vitaceae, e.g.
Vitis vinifera

Bromeliaceae, e.g.

Ananas sativus.

The compositions may also be used as total herbicides on ditches, aquatic areas, railway track, barren and waste land, etc.

The compositions were examined in the greenhouse and in the open on the above plants. Their action corresponds to that of the compositions in Examples 1 to 13.

EXAMPLE 1

In the greenhouse, pots were filled with loamy sandy soil; various seeds were then sown and bulbs planted therein. The soil prepared in this manner was then treated with the following amounts of the following individual active ingredients and compositions thereof as aqueous solutions, emulsions, dispersions or high-percentage suspensions:

I 3-isopropyl-2,1,3-benzothiadiazinone-(4)-2,2-dioxide

II 3-isopropyl-2,1,3-benzothiadiazinone-(4)-2,2-dioxide, sodium salt

III 3-isopropyl-2,1,3-benzothiadiazinone-(4)-2,2-dioxide, dimethylammonium salt

IV 3-isopropyl-2,1,3-benzothiadiazinone-(4)-2,2-dioxide, diethanolammonium salt

V O-(methylaminosulfonyl)-glycolic acid hexamethylene amide

XIV 3-(ethylaminosulfonyloxyacetyl)-3-azabicyclo-[3,2,2]-nonane

XXX O-(dimethylaminosulfonyl)-glycolic acid-N-ethyl anilide, each of the above compounds at rates of 0.5, 0.75, 1, 1.5, 2, 3 and 4 kg/ha;

I+V, II+V, III+V, IV+V, I+XIV, II+XIV, III+XIV, IV+XIV, I+XXX, II+XXX, III+XXX and IV+XXX, each of these compositions at rates of 0.75+0.75, 1+1, 1.50+0.5, 0.5+1.5, 2+1, 1+2 and 2+2 kg/ha; I+V, I+XIV, I+XXX, II+V, II+XIV and II+XXX each of these compositions at rates of 3+1 and 1.5+1.5 kg/ha.

The soil was then flooded to a depth of 10 cm.

after 4 to 5 weeks it was ascertained that at the lower rates the compositions had a better herbicidal action than the individual active ingredients, combined with the same compatibility with the crop plant, *Oryza sativa*. The compatibility with rice is still good at the higher application rates too.

The results are given below:

| Active ingredient | I | | | | | | | II | | | | | | |
|---|---|---|---|---|---|---|---|---|---|---|---|---|---|---|
| kg/ha | 0.5 | 0.75 | 1 | 1.5 | 2 | 3 | 4 | 0.5 | 0.75 | 1 | 1.5 | 2 | 3 | 4 |
| Crop plant: | | | | | | | | | | | | | | |
| Orysa sativa | 0 | 0 | 0 | 0 | 0 | 0 | 0 | 0 | 0 | 0 | 0 | 0 | 0 | 0 |
| Unwanted plants: | | | | | | | | | | | | | | |
| Cyperus esculentus | 0 | 0 | 5 | 10 | 20 | 30 | 40 | 0 | 0 | 5 | 7 | 20 | 25 | 35 |
| Echinochloa crus-galli | 0 | 3 | 5 | 12 | 15 | 20 | 25 | 0 | 0 | 5 | 7 | 15 | 20 | 30 |
| Alisma plantago aquatica | 0 | 7 | 10 | 20 | 25 | 30 | 40 | 0 | 5 | 15 | 20 | 25 | 35 | 40 |

| | III | | | | | | | IV | | | | | | |
|---|---|---|---|---|---|---|---|---|---|---|---|---|---|---|
| Oryza sativa | 0 | 0 | 0 | 0 | 0 | 0 | 0 | 0 | 0 | 0 | 0 | 0 | 0 | 0 |
| Cyperus esculentus | 0 | 0 | 7 | 10 | 15 | 25 | 35 | 0 | 0 | 10 | 20 | 25 | 35 | 45 |
| Echinochloa crus-galli | 0 | 3 | 5 | 10 | 15 | 20 | 30 | 0 | 5 | 10 | 20 | 30 | 37 | 45 |
| Alisma plantago aquatica | 0 | 10 | 20 | 25 | 30 | 35 | 45 | 0 | 8 | 10 | 15 | 20 | 35 | 40 |

| | V | | | | | | | XIV | | | | | | |
|---|---|---|---|---|---|---|---|---|---|---|---|---|---|---|
| Oryza sativa | 0 | 0 | 0 | 0 | 0 | 0 | 10 | 0 | 0 | 0 | 0 | 0 | 0 | 10 |
| Cyperus esculentus | 50 | 70 | 90 | 100 | 100 | 100 | 100 | 35 | 50 | 60 | 70 | 85 | 100 | 100 |
| Echinochloa crus-galli | 40 | 70 | 85 | 98 | 100 | 100 | 100 | 30 | 60 | 80 | 95 | 100 | 100 | 100 |
| Alisma plantago aquatica | 15 | 18 | 25 | 35 | 40 | 50 | 65 | 10 | 15 | 20 | 25 | 30 | 40 | 60 |

| | XXX | | | | | | | I + V | | | | | |
|---|---|---|---|---|---|---|---|---|---|---|---|---|---|
| kg/ha | | | | | | | | 0.75 | 1 | 1.5 | 0.5 | 2 | 1 | 2 |
| | 0.5 | 0.75 | 1 | 1.5 | 2 | 3 | 4 | 0.75 | 1 | 0.5 | 1.5 | 1 | 2 | 2 |
| Crop plant: | | | | | | | | | | | | | | |
| Oryza sativa | 0 | 0 | 0 | 0 | 0 | 0 | 10 | 0 | 0 | 0 | 0 | 0 | 0 | 0 |
| Unwanted plants: | | | | | | | | | | | | | | |
| Cyperus esculentus | 30 | 40 | 60 | 70 | 90 | 100 | 100 | 100 | 100 | 100 | 100 | 100 | 100 | 100 |
| Echinochloa crus-galli | 45 | 65 | 70 | 85 | 100 | 100 | 100 | 100 | 100 | 100 | 100 | 100 | 100 | 100 |
| Alisma plantago aquatica | 12 | 15 | 20 | 25 | 35 | 50 | 60 | 65 | 75 | 77 | 75 | 90 | 93 | 100 |

| | II + V | | | | | | III + V | | | | | |
|---|---|---|---|---|---|---|---|---|---|---|---|---|
| kg/ha | 0.75 | 1 | 1.5 | 0.5 | 2 | 1 | 2 | 0.75 | 1 | 1.5 | 0.5 | 2 | 1 | 2 |
| | 0.75 | 1 | 0.5 | 1.5 | 1 | 2 | 2 | 0.75 | 1 | 0.5 | 1.5 | 1 | 2 | 2 |
| Oryza sativa | 0 | 0 | 0 | 0 | 0 | 0 | 0 | 0 | 0 | 0 | 0 | 0 | 0 | 0 |
| Cyperus esculentus | 100 | 100 | 100 | 100 | 100 | 100 | 100 | 100 | 100 | 100 | 100 | 100 | 100 | 100 |
| Echinochloa crus-galli | 100 | 100 | 95 | 100 | 100 | 100 | 100 | 100 | 100 | 100 | 100 | 100 | 100 | 100 |
| Alisma plantago aquatica | 63 | 80 | 75 | 75 | 90 | 85 | 95 | 69 | 85 | 80 | 75 | 95 | 100 | 100 |

| | IV + V | | | | | | | I + XIV | | | | | |
|---|---|---|---|---|---|---|---|---|---|---|---|---|---|
| Oryza sativa | 0 | 0 | 0 | 0 | 0 | 0 | 0 | 0 | 0 | 0 | 0 | 0 | 0 | 0 |
| Cyperus esculentus | 100 | 100 | 100 | 100 | 100 | 100 | 100 | 90 | 100 | 90 | 100 | 100 | 100 | 100 |
| Echinochloa crus-galli | 100 | 100 | 100 | 100 | 100 | 100 | 100 | 100 | 100 | 90 | 100 | 100 | 100 | 100 |
| Alisma plantago aquatica | 66 | 75 | 70 | 75 | 85 | 90 | 100 | 62 | 70 | 70 | 65 | 85 | 80 | 95 |

| | II + XIV | | | III + XIV | |

-continued

| Crop plant: | | | | | | | | | | | | | | |
|---|---|---|---|---|---|---|---|---|---|---|---|---|---|---|
| Oryza sativa | 0 | 0 | 0 | 0 | 0 | 0 | 0 | 0 | 0 | 0 | 0 | 0 | 0 | 0 |
| Unwanted plants: | | | | | | | | | | | | | | |
| Cyperus esculentus | 90 | 100 | 100 | 100 | 100 | 100 | 100 | 90 | 100 | 100 | 100 | 100 | 100 | 100 |
| Echinochloa crus-galli | 98 | 100 | 90 | 100 | 100 | 100 | 100 | 100 | 100 | 100 | 100 | 100 | 100 | 100 |
| Alisma plantago aquatica | 60 | 75 | 70 | 65 | 85 | 100 | 100 | 65 | 80 | 75 | 70 | 90 | 92 | 100 |

| | IV + XIV | | | | | | | | I + XXX | | | | | |
|---|---|---|---|---|---|---|---|---|---|---|---|---|---|---|
| Oryza sativa | 0 | 0 | 0 | 0 | 0 | 0 | 0 | 0 | 0 | 0 | 0 | 0 | 0 | 0 |
| Cyperus esculentus | 93 | 100 | 100 | 100 | 100 | 100 | 100 | 80 | 100 | 100 | 100 | 100 | 100 | 100 |
| Echinochloa crus-galli | 100 | 100 | 100 | 100 | 100 | 100 | 100 | 100 | 100 | 100 | 100 | 100 | 100 | 100 |
| Alisma plantago aquatica | 63 | 70 | 65 | 65 | 80 | 80 | 90 | 62 | 70 | 72 | 65 | 85 | 85 | 100 |

| | II + XXX | | | | | | | | III + XXX | | | | | |
|---|---|---|---|---|---|---|---|---|---|---|---|---|---|---|
| Oryza sativa | 0 | 0 | 0 | 0 | 0 | 0 | 0 | 0 | 0 | 0 | 0 | 0 | 0 | 0 |
| Cyperus esculentus | 83 | 100 | 90 | 100 | 100 | 100 | 100 | 81 | 100 | 95 | 100 | 100 | 100 | 100 |
| Echinochloa crus-galli | 100 | 100 | 100 | 100 | 100 | 100 | 100 | 100 | 100 | 100 | 100 | 100 | 100 | 100 |
| Alisma plantago aquatica | 60 | 75 | 72 | 65 | 85 | 90 | 100 | 65 | 80 | 73 | 70 | 90 | 95 | 100 |

| | IV + XXX | | | I+ V | | I+ XIV | | I+ XXX | | II+ V | | | |
|---|---|---|---|---|---|---|---|---|---|---|---|---|---|
| kg/ha | 0.75 | 1 | 1.5 | 0.5 | 2 | 1 | 2 | 3 | 1.5 | 3 | 1.5 | 3 | 1.5 | 3 | 1.5 |
| | 0.75 | 1 | 0.5 | 1.5 | 1 | 2 | 2 | 1 | 1.5 | 1 | 1.5 | 1 | 1.5 | 1 | 1.5 |

| Crop plant: | | | | | | | | | | | | | | |
|---|---|---|---|---|---|---|---|---|---|---|---|---|---|---|
| Oryza sativa | 0 | 0 | 0 | 0 | 0 | 0 | 0 | 0 | 0 | 0 | 0 | 0 | 0 | 0 | 0 |
| Unwanted plants: | | | | | | | | | | | | | | |
| Cyperus esculentus | 80 | 100 | 95 | 100 | 100 | 100 | 100 | 100 | 100 | 100 | 100 | 100 | 100 | 100 | 100 |
| Echinochloa crus-galli | 100 | 100 | 100 | 100 | 100 | 100 | 100 | 100 | 100 | 100 | 100 | 100 | 100 | 100 | 100 |
| Matricaria chamomilla | 64 | 70 | 67 | 65 | 80 | 85 | 100 | 97 | 95 | 90 | 87 | 92 | 83 | 100 | 97 |

| | II+ XIV | | II+ XXX | | | | | | | | | | | |
|---|---|---|---|---|---|---|---|---|---|---|---|---|---|---|
| kg/ha | 3 | 1.5 | 3 | 1.5 | | | | | | | | | | |
| | 1 | 1.5 | 1 | 1.5 | | | | | | | | | | |

| Oryza sativa | 0 | 0 | 0 | 0 |
|---|---|---|---|---|
| Cyperus esculentus | 100 | 100 | 100 | 100 |
| Echinochloa crus-galli | 100 | 100 | 100 | 100 |
| Matricaria chamomilla | 95 | 80 | 93 | 85 |

0 = no damage
100 = complete destruction

EXAMPLE 2

In the open, various plants were treated at a growth height of from 2 to 17 cm with the following amounts of the following individual active ingredients and compositions thereof as emulsions, dispersions, suspensions or aqueus solutions:

I 3-isopropyl-2,1,3-benzothiadiazinone-(4)-2,2-dioxide

II 3-isopropyl-2,1,3-benzothiadiazinone-(4)-2,2-dioxide, sodium salt

III 3-isopropyl-2,1,3-benzothiadiazinone-(4)-2,2-dioxide, dimethylammonium salt

IV 3-isopropyl-2,1,3-benzothiadiazonone-(4)-2,2-dioxide, diethanolammonium salt

V O-(methylaminosulfonyl)-glycolic acid hexamethylene amide,

VI O-(ethylaminosulfonyl)-glycolic acid hexamethylene amide,

VII 3-(methylaminosulfonyloxyacetyl)-3-azabicyclo-[3,2,2]-nonane,

VIII O-(methylaminosulfonyl)-glycolic acid heptamethylene amide

IX 3-(isopropylaminosulfonyloxyacetyl)-3-azabicyclo-[3,2,2]-nonane,

X O-(n-propylaminosulfonyl)-glycolic acid hexamethylene amide,

XI O-(isopropylaminosulfonyl)-glycolic acid hexamethylene amide,

XII O-(isopropylaminosulfonyl)-glycolic acid-N-butyn-1-yl-3-anilide,

XIII O-(methylaminosulfonyl)-glycolic acid-N-isopropylanilide,

XIV 3-(ethylaminosulfonyloxyacetyl)-3-azabicyclo-[3,2,2]-nonane,

XV O-(methylsulfonyl)-glycolic acid-N-ethoxymethyl-2,6-dimethylanilide,

XVI O-(methylsulfonyl)-gylcolic acid-N-ethoxymethyl-2-methyl-6-ethylanilide,

XVII O-(ethylaminosulfonyl)-glycolic acid-N-butyn-1-yl-3-anilide,

XVIII O-(methylaminosulfonyl)-glycolic acid-N-butyn-1-yl-3-anilide, each of these compounds at rates of
0.25, 0.5, 0.75, 1, 1.5, 2, 2.5, 2.75, 3 and 4 kg/ha;
I+V, I+VI, I+VII, I+VIII, I+IX, I+X, I+XI, I+XII, I+XIII, I+XIV, I+XV, I+XVI, I+XVII, I+XVIII, II+V, II+VI, II+VII, II+VIII, II+IX, II+X, II+XI, II+XII, II+XIII, II+XIV, II+XV, II+XVI, II+XVII, II+XVIII, III+V, III+VI, III+VII, III+VIII, III+IX, III+X, III+XI, III+XII, III+XIII, III+XIV, III+XV, III+XVI, III+XVII, III+XVIII, IV+V, IV+VI, IV+VII, IV+VIII, IV+IX, IV+X, IV+XI, IV+XII, IV+XIII, IX+XIV, IV+XV, IV+XVI, IV+XVIII and IV+XVIII each of these compositions at rates of
0.25+0.25, 0,5+0.5, 0.75+0.25, 0.27+0.75, 1+0.5, 0.5+1, 0.75+0.75, 1+1, 0.5+1.5, 1.5+0.5, 2+0.5, 0.5+2, 2.5+0.25, 0.25+2.5, 0.t+2.5, 2,5+0.5, 1.5+1.5, 1+3, 3+1 and 2+2 kg/ha.

I+V, I+IX, I+XIII, I+XV, II+V, II+IX, II+XIII, II+XV, III+V, III+IX, III+XIII, II+XV, IV+V, IX+IX, IV+VIII, IV+XV each of these compositions at rates of 2+1 and 1+2 kg/ha.

After 3 to 4 weeks it was ascertained that at the lower application rates the compositions had a better herbicidal action than their components, combined with the same crop plant compatibility. At the higher application rates the compatibility of the compositions with the crop plant, Glycine max., was still good.

The results are given below:

| Active ingredient kg/ha | 0.25 | 0.5 | 0.75 | 1 | I 1.5 | 2 | 2.5 | 2.75 | 3 | 4 |
|---|---|---|---|---|---|---|---|---|---|---|
| Crop plant: | | | | | | | | | | |
| Glycine max | 0 | 0 | 0 | 0 | 0 | 0 | 5 | 7 | 10 | 20 |
| Unwanted plants: | | | | | | | | | | |
| Setaria faberii | 0 | 5 | 7 | 10 | 10 | 15 | 20 | 23 | 25 | 30 |
| Lamium amplexicaule | 5 | 10 | 20 | 30 | 40 | 60 | 65 | 68 | 70 | 95 |
| Amaranthus retroflexus | 20 | 30 | 35 | 40 | 60 | 70 | 95 | 98 | 100 | 100 |
| II | | | | | | | | | | |
| Glycine max | 0 | 0 | 0 | 0 | 0 | 0 | 5 | 10 | 15 | 25 |
| Setaria faberii | 0 | 6 | 10 | 15 | 20 | 25 | 28 | 32 | 35 | 40 |
| Lamium amplexicaule | 5 | 10 | 15 | 25 | 40 | 54 | 60 | 65 | 75 | 90 |
| Amaranthus retroflexus | 15 | 25 | 35 | 40 | 55 | 70 | 90 | 95 | 98 | 100 |
| III | | | | | | | | | | |
| Glycine max | 0 | 0 | 0 | 0 | 0 | 0 | 7 | 10 | 12 | 20 |
| Setaria faberii | 0 | 4 | 7 | 10 | 15 | 20 | 25 | 27 | 30 | 35 |
| Lamium amplexicaule | 5 | 10 | 20 | 30 | 45 | 50 | 55 | 58 | 60 | 80 |
| Amaranthus retroflexus | 15 | 25 | 30 | 40 | 60 | 65 | 80 | 90 | 95 | 100 |
| IV | | | | | | | | | | |
| Glycine max | 0 | 0 | 0 | 0 | 0 | 0 | 5 | 8 | 10 | 20 |
| Setaria faberii | 0 | 5 | 10 | 15 | 20 | 23 | 25 | 28 | 30 | 35 |
| Lamium amplexicaule | 6 | 10 | 25 | 35 | 48 | 60 | 65 | 70 | 75 | 87 |
| Amaranthus retroflexus | 20 | 30 | 35 | 40 | 60 | 68 | 90 | 94 | 98 | 100 |
| V | | | | | | | | | | |
| Crop plant: | | | | | | | | | | |
| Glycine max | 0 | 0 | 0 | 0 | 0 | 0 | 0 | 5 | 7 | 10 |
| Unwanted plants: | | | | | | | | | | |
| Setaria faberii | 20 | 30 | 45 | 60 | 80 | 90 | 98 | 100 | 100 | 100 |
| Lamium amplexicaule | 0 | 5 | 15 | 20 | 35 | 45 | 47 | 53 | 55 | 60 |
| Amaranthus retroflexus | 10 | 15 | 25 | 30 | 50 | 60 | 65 | 68 | 70 | 80 |
| VI | | | | | | | | | | |
| Glycine max | 0 | 0 | 0 | 0 | 0 | 0 | 3 | 7 | 10 | 15 |
| Setaria faberii | 25 | 35 | 50 | 65 | 85 | 95 | 100 | 100 | 100 | 100 |
| Lamium amplexicaule | 0 | 6 | 15 | 20 | 38 | 50 | 55 | 58 | 60 | 75 |
| Amaranthus retroflexus | 10 | 18 | 27 | 35 | 55 | 65 | 70 | 73 | 80 | 90 |
| VII | | | | | | | | | | |
| Glycine max | 0 | 0 | 0 | 0 | 0 | 0 | 0 | 3 | 5 | 10 |
| Setaria faberii | 15 | 20 | 30 | 40 | 60 | 75 | 85 | 90 | 95 | 100 |
| Lamium amplexicaule | 0 | 0 | 10 | 15 | 20 | 25 | 28 | 30 | 35 | 45 |
| Amaranthus retroflexus | 0 | 0 | 3 | 8 | 15 | 25 | 30 | 35 | 40 | 50 |
| VIII | | | | | | | | | | |
| Glycine max | 0 | 0 | 0 | 0 | 0 | 0 | 0 | 0 | 4 | 10 |
| Setaria faberii | 12 | 20 | 30 | 40 | 60 | 70 | 80 | 85 | 95 | 100 |
| Lamium amplexicaule | 0 | 0 | 5 | 10 | 15 | 18 | 25 | 30 | 35 | 45 |
| Amaranthus retroflexus | 0 | 3 | 6 | 10 | 17 | 25 | 30 | 35 | 45 | 55 |
| IX | | | | | | | | | | |
| Crop plant: | | | | | | | | | | |
| Glycine max | 0 | 0 | 0 | 0 | 0 | 0 | 0 | 0 | 6 | 10 |
| Unwanted plants: | | | | | | | | | | |
| Setaria faberii | 13 | 20 | 30 | 38 | 60 | 75 | 86 | 90 | 95 | 100 |
| Lamium amplexicaule | 0 | 0 | 3 | 5 | 10 | 20 | 25 | 30 | 34 | 40 |
| Amaranthus retroflexus | 0 | 0 | 5 | 10 | 20 | 30 | 35 | 40 | 48 | 55 |
| X | | | | | | | | | | |
| Glycine max | 0 | 0 | 0 | 0 | 0 | 0 | 5 | 8 | 10 | 15 |
| Setaria faberii | 25 | 35 | 48 | 70 | 80 | 90 | 95 | 98 | 100 | 100 |
| Lamium amplexicaule | 5 | 10 | 20 | 25 | 40 | 50 | 55 | 60 | 62 | 70 |
| Amaranthus retroflexus | 15 | 20 | 30 | 40 | 53 | 60 | 65 | 70 | 75 | 85 |
| XI | | | | | | | | | | |
| Glycine max | 0 | 0 | 0 | 0 | 0 | 0 | 0 | 2 | 6 | 10 |
| Setaria faberii | 15 | 25 | 40 | 50 | 60 | 70 | 80 | 85 | 90 | 100 |
| Lamium amplexicaule | 0 | 4 | 10 | 15 | 20 | 25 | 30 | 35 | 40 | 50 |
| Amaranthus retroflexus | 5 | 13 | 20 | 26 | 50 | 57 | 61 | 65 | 70 | 80 |
| XII | | | | | | | | | | |
| Glycine max | 0 | 0 | 0 | 0 | 0 | 0 | 0 | 0 | 5 | 10 |
| Setaria faberii | 35 | 45 | 60 | 75 | 85 | 95 | 100 | 100 | 100 | 100 |
| Lamium amplexicaule | 0 | 7 | 15 | 20 | 30 | 40 | 45 | 50 | 52 | 60 |
| Amaranthus retroflexus | 5 | 10 | 20 | 25 | 40 | 70 | 80 | 85 | 90 | 98 |

-continued

XIII

| | | | | | | | | | | |
|---|---|---|---|---|---|---|---|---|---|---|
| Crop plant: | | | | | | | | | | |
| *Glycine max* | 0 | 0 | 0 | 0 | 0 | 0 | 0 | 0 | 4 | 8 |
| Unwanted plants: | | | | | | | | | | |
| *Setaria faberii* | 20 | 30 | 45 | 60 | 70 | 80 | 95 | 100 | 100 | 100 |
| *Lamium amplexicaule* | 0 | 0 | 10 | 15 | 20 | 25 | 27 | 30 | 35 | 40 |
| *Amaranthus retroflexus* | 0 | 5 | 10 | 20 | 30 | 34 | 38 | 45 | 55 | 65 |

XIV

| | | | | | | | | | | |
|---|---|---|---|---|---|---|---|---|---|---|
| *Glycine max* | 0 | 0 | 0 | 0 | 0 | 0 | 3 | 7 | 10 | 20 |
| *Setaria faberii* | 20 | 30 | 40 | 50 | 65 | 80 | 85 | 95 | 100 | 100 |
| *Lamium amplexicaule* | 0 | 0 | 4 | 10 | 15 | 20 | 30 | 35 | 39 | 45 |
| *Amaranthus retroflexus* | 7 | 15 | 20 | 30 | 40 | 45 | 55 | 60 | 65 | 80 |

XV

| | | | | | | | | | | |
|---|---|---|---|---|---|---|---|---|---|---|
| *Glycine max* | 0 | 0 | 0 | 0 | 0 | 0 | 0 | 0 | 4 | 10 |
| *Setaria faberii* | 15 | 25 | 45 | 60 | 70 | 80 | 90 | 95 | 100 | 100 |
| *Lamium amplexicaule* | 0 | 0 | 0 | 3 | 6 | 10 | 20 | 25 | 30 | 40 |
| *Amaranthus retroflexus* | 0 | 0 | 5 | 10 | 15 | 20 | 22 | 29 | 34 | 40 |

XVI

| | | | | | | | | | | |
|---|---|---|---|---|---|---|---|---|---|---|
| *Glycine max* | 0 | 0 | 0 | 0 | 0 | 0 | 0 | 0 | 5 | 10 |
| *Setaria faberii* | 10 | 20 | 40 | 55 | 65 | 75 | 87 | 92 | 98 | 100 |
| *Lamium amplexicaule* | 0 | 0 | 0 | 2 | 5 | 10 | 20 | 24 | 30 | 40 |
| *Amaranthus retroflexus* | 0 | 0 | 0 | 5 | 10 | 15 | 20 | 25 | 30 | 37 |

XVII

| | | | | | | | | | | |
|---|---|---|---|---|---|---|---|---|---|---|
| Crop plant: | | | | | | | | | | |
| *Glycine max* | 0 | 0 | 0 | 0 | 0 | 0 | 5 | 7 | 10 | 20 |
| Unwanted plants: | | | | | | | | | | |
| *Setaria faberii* | 30 | 50 | 60 | 75 | 90 | 100 | 100 | 100 | 100 | 100 |
| *Lamium amplexicaule* | 0 | 0 | 4 | 10 | 15 | 20 | 25 | 27 | 30 | 40 |
| *Amaranthus retroflexus* | 5 | 10 | 20 | 28 | 40 | 50 | 58 | 60 | 65 | 70 |

XVIII

| | | | | | | | | | | |
|---|---|---|---|---|---|---|---|---|---|---|
| *Glycine max* | 0 | 0 | 0 | 0 | 0 | 0 | 6 | 10 | 12 | 20 |
| *Setaria faberii* | 35 | 55 | 65 | 80 | 90 | 96 | 100 | 100 | 100 | 100 |
| *Lamium amplexicaule* | 0 | 0 | 2 | 5 | 10 | 15 | 22 | 26 | 30 | 45 |
| *Amaranthus retroflexus* | 6 | 10 | 20 | 25 | 40 | 50 | 55 | 60 | 70 | 75 |

I + V

| kg/ha | 0.25 / 0.25 | 0.5 / 0.5 | 0.75 / 0.25 | 0.25 / 0.75 | 1 / 0.5 | 0.5 / 1 | 0.75 / 0.75 | 1 / 1 | 0.5 / 1.5 | 1.5 / 0.5 | 2 / 0.5 | 0.5 / 2 | 2.5 / 0.25 |
|---|---|---|---|---|---|---|---|---|---|---|---|---|---|
| Crop plant: | | | | | | | | | | | | | |
| *Glycine max* | 0 | 0 | 0 | 0 | 0 | 0 | 0 | 0 | 0 | 0 | 0 | 0 | 5 |
| Unwanted plants: | | | | | | | | | | | | | |
| *Setaria faberii* | 58 | 75 | 67 | 85 | 82 | 100 | 93 | 100 | 100 | 95 | 98 | 100 | 100 |
| *Lamium amplexicaule* | 46 | 55 | 60 | 60 | 70 | 72 | 77 | 87 | 88 | 87 | 100 | 95 | 100 |
| *Amaranthus retroflexus* | 70 | 85 | 85 | 86 | 95 | 98 | 97 | 100 | 100 | 100 | 100 | 100 | 100 |

| kg/ha | 0.25 / 2.5 | 0.5 / 2.5 | 2.5 / 0.5 | 1.5 / 1.5 | 1 / 3 | 3 / 1 | 2 / 2 | 2 / 1 | 1 / 2 |
|---|---|---|---|---|---|---|---|---|---|
| *Glycine max* | 0 | 0 | 5 | 0 | 7 | 10 | 0 | 0 | 0 |
| *Setaria faberii* | 100 | 100 | 100 | 100 | 100 | 100 | 100 | 100 | 100 |
| *Lamium amplexicaule* | 96 | 100 | 100 | 100 | 100 | 100 | 100 | 100 | 100 |
| *Amaranthus retroflexus* | 100 | 100 | 100 | 100 | 100 | 100 | 100 | 100 | 100 |

I + VI

| kg/ha | 0.25 / 0.25 | 0.5 / 0.5 | 0.75 / 0.25 | 0.25 / 0.75 | 1 / 0.5 | 0.5 / 1 | 0.75 / 0.75 | 1 / 1 | 0.5 / 1.5 | 1.5 / 0.5 | 2 / 0.5 | 0.5 / 2 | 0.5 / 0.25 |
|---|---|---|---|---|---|---|---|---|---|---|---|---|---|
| Crop plant: | | | | | | | | | | | | | |
| *Glycine max* | 0 | 0 | 0 | 0 | 0 | 0 | 0 | 0 | 0 | 0 | 0 | 0 | 5 |
| Unwanted plants: | | | | | | | | | | | | | |
| *Setaria faberii* | 58 | 70 | 72 | 80 | 90 | 95 | 93 | 98 | 100 | 94 | 100 | 100 | 100 |
| *Lamium amplexicaule* | 46 | 50 / 60 | 57 | 65 | 52 | 72 | 87 | 85 | 80 | 98 | 97 | 98 | |
| *Amaranthus retroflexus* | 70 | 83 | 85 | 80 | 92 | 98 | 95 | 100 | 100 | 100 | 100 | 100 | 100 |

| kg/ha | 0.25 / 2.5 | 0.5 / 2.5 | 2.5 / 0.5 | 1.5 / 1.5 | 1 / 3 | 3 / 1 | 2 / 2 |
|---|---|---|---|---|---|---|---|
| *Glycine max* | 3 | 3 | 5 | 0 | 10 | 10 | 0 |
| *Setaria faberii* | 100 | 100 | 100 | 100 | 100 | 100 | 100 |
| *Lamium amplexicaule* | 95 | 100 | 100 | 100 | 100 | 100 | 100 |
| *Amaranthus retroflexus* | 100 | 100 | 100 | 100 | 100 | 100 | 100 |

I + VII

| kg/ha | 0.25 / 0.25 | 0.5 / 0.5 | 0.75 / 0.25 | 0.25 / 0.75 | 1 / 0.5 | 0.5 / 1 | 0.75 / 0.75 | 1 / 1 | 0.5 / 1.5 | 1.5 / 0.5 | 2 / 0.5 | 0.5 / 2 | 2.5 / 0.25 |
|---|---|---|---|---|---|---|---|---|---|---|---|---|---|
| Crop plant: | | | | | | | | | | | | | |
| *Glycine max* | 0 | 0 | 0 | 0 | 0 | 0 | 0 | 0 | 0 | 0 | 0 | 0 | 5 |

-continued

| Unwanted plants: | | | | | | | | | | | | | |
|---|---|---|---|---|---|---|---|---|---|---|---|---|---|
| Setaria faberii | 60 | 65 | 63 | 70 | 72 | 85 | 80 | 90 | 100 | 80 | 86 | 100 | 90 |
| Lamium amplexicaule | 46 | 50 | 60 | 47 | 70 | 65 | 70 | 85 | 70 | 80 | 98 | 75 | 100 |
| Amaranthus retroflexus | 60 | 68 | 73 | 62 | 80 | 77 | 78 | 85 | 90 | 100 | 100 | 100 | 100 |

| kg/ha | 0.25 | 0.5 | 2.5 | 1.5 | 1 | 3 | 2 | | | | | | |
|---|---|---|---|---|---|---|---|---|---|---|---|---|---|
| | 2.5 | 2.5 | 0.5 | 1.5 | 3 | 1 | 2 | | | | | | |

| Glycine max | 0 | 0 | 5 | 0 | 5 | 10 | 0 | | | | | | |
|---|---|---|---|---|---|---|---|---|---|---|---|---|---|
| Setaria faberii | 100 | 100 | 95 | 100 | 100 | 100 | 100 | | | | | | |
| Lamium amplexicaule | 75 | 80 | 100 | 100 | 100 | 100 | 100 | | | | | | |
| Amaranthus retroflexus | 100 | 100 | 100 | 100 | 100 | 100 | 100 | | | | | | |

I + VIII

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |

| Crop plant: | | | | | | | | | | | | | |
|---|---|---|---|---|---|---|---|---|---|---|---|---|---|
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 59 | 70 | 65 | 70 | 75 | 85 | 80 | 90 | 100 | 85 | 89 | 100 | 90 |
| Lamium amplexicaule | 46 | 50 | 60 | 47 | 65 | 61 | 65 | 80 | 66 | 80 | 98 | 75 | 97 |
| Amaranthus retroflexus | 60 | 69 | 73 | 63 | 80 | 80 | 75 | 90 | 90 | 100 | 100 | 100 | 100 |

| kg/ha | 0.25 | 0.5 | 2.5 | 1.5 | 1 | 3 | 2 | | | | | | |
|---|---|---|---|---|---|---|---|---|---|---|---|---|---|
| | 2.5 | 2.5 | 0.5 | 1.5 | 3 | 1 | 2 | | | | | | |

| Glycine max | 0 | 0 | 5 | 0 | 4 | 10 | 0 | | | | | | |
|---|---|---|---|---|---|---|---|---|---|---|---|---|---|
| Setaria faberii | 100 | 100 | 98 | 100 | 100 | 100 | 100 | | | | | | |
| Lamium amplexicaule | 90 | 80 | 95 | 95 | 100 | 100 | 100 | | | | | | |
| Amaranthus retroflexus | 100 | 100 | 100 | 100 | 100 | 100 | 100 | | | | | | |

I + IX

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |

| Crop plant: | | | | | | | | | | | | | |
|---|---|---|---|---|---|---|---|---|---|---|---|---|---|
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 58 | 75 | 68 | 78 | 80 | 98 | 87 | 100 | 100 | 90 | 95 | 100 | 90 |
| Lamium amplexicaule | 45 | 50 | 60 | 46 | 65 | 60 | 63 | 68 | 64 | 80 | 90 | 72 | 98 |
| Amaranthus retroflexus | 59 | 67 | 73 | 60 | 79 | 76 | 75 | 85 | 90 | 100 | 100 | 100 | 100 |

| kg/ha | 0.25 | 0.5 | 2.5 | 1.5 | 1 | 3 | 2 | 2 | 1 | | | | |
|---|---|---|---|---|---|---|---|---|---|---|---|---|---|
| | 2.5 | 2.5 | 0.5 | 1.5 | 3 | 1 | 2 | 1 | 2 | | | | |

| Glycine max | 0 | 0 | 5 | 0 | 6 | 10 | 0 | 0 | 0 | | | | |
|---|---|---|---|---|---|---|---|---|---|---|---|---|---|
| Setaria faberii | 100 | 100 | 100 | 100 | 100 | 100 | 100 | 93 | 100 | | | | |
| Lamium amplexicaule | 80 | 85 | 100 | 90 | 100 | 100 | 100 | 100 | 90 | | | | |
| Amaranthus retroflexus | 100 | 100 | 100 | 100 | 100 | 100 | 100 | 100 | 100 | | | | |

I + X

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |

| Crop plant: | | | | | | | | | | | | | |
|---|---|---|---|---|---|---|---|---|---|---|---|---|---|
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 62 | 80 | 72 | 85 | 87 | 100 | 95 | 100 | 100 | 95 | 97 | 100 | 100 |
| Lamium amplexicaule | 48 | 60 | 60 | 62 | 80 | 75 | 80 | 95 | 90 | 89 | 100 | 100 | 100 |
| Amaranthus retroflexus | 75 | 90 | 90 | 91 | 98 | 100 | 100 | 100 | 100 | 100 | 100 | 100 | 100 |

| kg/ha | 0.25 | 0.5 | 2.5 | 1.5 | 1 | 3 | 2 | | | | | | |
|---|---|---|---|---|---|---|---|---|---|---|---|---|---|
| | 2.5 | 2.5 | 0.5 | 1.5 | 3 | 1 | 2 | | | | | | |

| Glycine max | 5 | 5 | 5 | 0 | 10 | 10 | 0 | | | | | | |
|---|---|---|---|---|---|---|---|---|---|---|---|---|---|
| Setaria faberii | 100 | 100 | 100 | 100 | 100 | 100 | 100 | | | | | | |
| Lamium amplexicaule | 100 | 100 | 100 | 100 | 100 | 100 | 100 | | | | | | |
| Amaranthus retroflexus | 100 | 100 | 100 | 100 | 100 | 100 | 100 | | | | | | |

I + XI

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |

| Crop plant: | | | | | | | | | | | | | |
|---|---|---|---|---|---|---|---|---|---|---|---|---|---|
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 60 | 75 | 67 | 85 | 80 | 100 | 92 | 100 | 100 | 87 | 93 | 100 | 93 |
| Lamium amplexicaule | 47 | 58 | 60 | 60 | 72 | 70 | 75 | 85 | 83 | 88 | 98 | 90 | 100 |
| Amaranthus retroflexus | 70 | 86 | 85 | 82 | 96 | 98 | 95 | 100 | 100 | 100 | 100 | 100 | 100 |

| kg/ha | 0.25 | 0.5 | 2.5 | 1.5 | 1 | 3 | 2 | | | | | | |
|---|---|---|---|---|---|---|---|---|---|---|---|---|---|
| | 2.5 | 2.5 | 0.5 | 1.5 | 3 | 1 | 2 | | | | | | |

| Glycine max | 0 | 0 | 5 | 0 | 6 | 10 | 0 | | | | | | |
|---|---|---|---|---|---|---|---|---|---|---|---|---|---|
| Setaria faberii | 100 | 100 | 100 | 100 | 100 | 100 | 100 | | | | | | |
| Lamium amplexicaule | 97 | 100 | 100 | 100 | 100 | 100 | 100 | | | | | | |
| Amaranthus retroflexus | 100 | 100 | 100 | 100 | 100 | 100 | 100 | | | | | | |

I + XII

-continued

| kg/ha | 0.25 0.25 | 0.5 0.5 | 0.75 0.25 | 0.25 0.75 | 1 0.5 | 0.5 1 | 0.75 0.75 | 1 1 | 0.5 1.5 | 1.5 0.5 | 2 0.5 | 0.5 2 | 2.5 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 0 |
| Unwanted plants: | | | | | | | | | | | | | |
| Setaria faberii | 62 | 80 | 79 | 90 | 92 | 100 | 100 | 100 | 100 | 100 | 100 | 100 | 100 |
| Lamium amplexicaule | 45 | 56 | 59 | 60 | 70 | 70 | 75 | 90 | 80 | 85 | 100 | 95 | 100 |
| Amaranthus retroflexus | 60 | 80 | 80 | 80 | 88 | 92 | 93 | 100 | 100 | 100 | 100 | 100 | 100 |

| kg/ha | 0.25 2.5 | 0.5 2.5 | 2.5 0.5 | 1.5 1.5 | 1 3 | 3 1 | 2 2 | | | | | | |
|---|---|---|---|---|---|---|---|---|---|---|---|---|---|
| Glycine max | 0 | 0 | 5 | 0 | 5 | 10 | 0 | | | | | | |
| Setaria faberii | 100 | 100 | 100 | 100 | 100 | 100 | 100 | | | | | | |
| Lamium amplexicaule | 100 | 100 | 100 | 100 | 100 | 100 | 100 | | | | | | |
| Amaranthus retroflexus | 100 | 100 | 100 | 100 | 100 | 100 | 100 | | | | | | |

I + XIII

| kg/ha | 0.25 0.25 | 0.5 0.5 | 0.75 0.25 | 0.25 0.75 | 1 0.5 | 0.5 1 | 0.75 0.75 | 1 1 | 0.5 1.5 | 1.5 0.5 | 2 0.5 | 0.5 2 | 2.5 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 57 | 76 | 67 | 85 | 87 | 97 | 95 | 100 | 100 | 98 | 100 | 100 | 100 |
| Lamium amplexicaule | 46 | 51 | 60 | 55 | 65 | 68 | 70 | 80 | 73 | 80 | 98 | 82 | 100 |
| Amaranthus retroflexus | 58 | 74 | 75 | 72 | 82 | 87 | 88 | 95 | 95 | 100 | 100 | 100 | 100 |

| kg/ha | 0.25 2.5 | 0.5 2.5 | 2.5 0.5 | 1.5 1.5 | 1 3 | 3 1 | 2 2 | 2 1 | 1 2 | | | | |
|---|---|---|---|---|---|---|---|---|---|---|---|---|---|
| Glycine max | 0 | 0 | 5 | 0 | 4 | 10 | 0 | 0 | 0 | | | | |
| Setaria faberii | 100 | 100 | 100 | 100 | 100 | 100 | 100 | 100 | 100 | | | | |
| Lamium amplexicaule | 90 | 92 | 100 | 100 | 100 | 100 | 100 | 100 | 95 | | | | |
| Amaranthus retroflexus | 100 | 100 | 100 | 100 | 100 | 100 | 100 | 100 | 100 | | | | |

I + XIV

| kg/ha | 0.25 0.25 | 0.5 0.5 | 0.75 0.25 | 0.25 0.75 | 1 0.5 | 0.5 1 | 0.75 0.75 | 1 1 | 0.5 1.5 | 1.5 0.5 | 2 0.5 | 0.5 2 | 0.5 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 60 | 75 | 67 | 80 | 82 | 95 | 86 | 97 | 100 | 88 | 94 | 100 | 97 |
| Lamium amplexicaule | 45 | 50 | 60 | 47 | 65 | 63 | 63 | 75 | 71 | 80 | 97 | 82 | 100 |
| Amaranthus retroflexus | 67 | 85 | 83 | 80 | 92 | 98 | 100 | 100 | 100 | 100 | 100 | 100 | 100 |

| kg/ha | 0.25 2.5 | 0.5 2.5 | 2.5 0.5 | 1.5 1.5 | 1 3 | 3 1 | 2 2 | | | | | | |
|---|---|---|---|---|---|---|---|---|---|---|---|---|---|
| Glycine max | 3 | 3 | 5 | 0 | 10 | 10 | 0 | | | | | | |
| Setaria faberii | 100 | 100 | 100 | 100 | 100 | 100 | 100 | | | | | | |
| Lamium amplexicaule | 84 | 91 | 100 | 100 | 100 | 100 | 100 | | | | | | |
| Amaranthus retroflexus | 100 | 100 | 100 | 100 | 100 | 100 | 100 | | | | | | |

I + XV

| kg/ha | 0.25 0.25 | 0.5 0.5 | 0.75 0.25 | 0.25 0.75 | 1 0.5 | 0.5 1 | 0.75 0.75 | 1 1 | 0.5 1.5 | 1.5 0.5 | 2 0.5 | 0.5 2 | 2.5 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 55 | 65 | 62 | 75 | 75 | 97 | 82 | 100 | 100 | 80 | 90 | 100 | 92 |
| Lamium amplexicaule | 46 | 50 | 57 | 47 | 65 | 52 | 60 | 68 | 60 | 80 | 97 | 70 | 100 |
| Amaranthus retroflexus | 57 | 68 | 73 | 60 | 80 | 75 | 75 | 82 | 88 | 100 | 100 | 100 | 100 |

| kg/ha | 0.25 2.5 | 0.5 2.5 | 2.5 0.5 | 1.5 1.5 | 1 3 | 3 1 | 2 2 | 2 1 | 1 2 | | | | |
|---|---|---|---|---|---|---|---|---|---|---|---|---|---|
| Glycine max | 0 | 0 | 5 | 0 | 4 | 10 | 0 | 0 | 0 | | | | |
| Setaria faberii | 100 | 100 | 100 | 100 | 100 | 100 | 100 | 100 | 100 | | | | |
| Lamium amplexicaule | 74 | 75 | 100 | 90 | 100 | 100 | 100 | 100 | 80 | | | | |
| Amaranthus retroflexus | 100 | 100 | 100 | 100 | 100 | 100 | 100 | 100 | 100 | | | | |

I + XVI

| kg/ha | 0.25 0.25 | 0.5 0.5 | 0.75 0.25 | 0.25 0.75 | 1 0.5 | 0.5 1 | 0.75 0.75 | 1 1 | 0.5 1.5 | 1.5 0.5 | 2 0.5 | 0.5 2 | 2.5 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 57 | 75 | 67 | 78 | 80 | 98 | 86 | 100 | 100 | 96 | 95 | 100 | 95 |
| Lamium amplexicaule | 45 | 50 | 60 | 47 | 65 | 60 | 63 | 70 | 67 | 80 | 96 | 75 | 100 |
| Amaranthus retroflexus | 60 | 70 | 75 | 63 | 80 | 80 | 77 | 90 | 90 | 100 | 100 | 100 | 100 |

| kg/ha | 0.25 2.5 | 0.5 2.5 | 2.5 0.5 | 1.5 1.5 | 1 3 | 3 1 | 2 2 | | | | | | |
|---|---|---|---|---|---|---|---|---|---|---|---|---|---|
| Glycine max | 0 | 0 | 5 | 0 | 5 | 10 | 0 | | | | | | |
| Setaria faberii | 100 | 100 | 100 | 100 | 100 | 100 | 100 | | | | | | |

-continued

| | | | | | | | | | | | | | |
|---|---|---|---|---|---|---|---|---|---|---|---|---|---|
| Lamium amplexicaule | 70 | 77 | 100 | 95 | 100 | | 100 | 100 | | | | | |
| Amaranthus retroflexus | 95 | 100 | 100 | 100 | 100 | | 100 | 100 | | | | | |

I + XVII

| kg/ha | 0.25 0.25 | 0.5 0.5 | 0.75 0.25 | 0.25 0.75 | 1 0.5 | 0.5 1 | 0.75 0.75 | 1 1 | 0.5 1.5 | 1.5 0.5 | 2 0.5 | 0.5 2 | 2.5 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 80 | 93 | 87 | 100 | 100 | 100 | 100 | 100 | 100 | 100 | 100 | 100 | 100 |
| Lamium amplexicaule | 44 | 50 | 60 | 47 | 65 | 60 | 60 | 80 | 65 | 80 | 97 | 70 | 100 |
| Amaranthus retroflexus | 65 | 80 | 70 | 80 | 90 | 97 | 95 | 100 | 100 | 100 | 100 | 100 | 100 |

| kg/ha | 0.25 2.5 | 0.5 2.5 | 2.5 0.5 | 1.5 1.5 | 1 3 | 3 1 | 2 2 |
|---|---|---|---|---|---|---|---|
| Glycine max | 5 | 5 | 5 | 0 | 10 | 10 | 0 |
| Setaria faberii | 100 | 100 | 100 | 100 | 100 | 100 | 100 |
| Lamium amplexicaule | 70 | 75 | 100 | 96 | 100 | 100 | 100 |
| Amaranthus retroflexus | 100 | 100 | 100 | 100 | 100 | 100 | 100 |

I + XVIII

| kg/ha | 0.25 0.25 | 0.5 0.5 | 0.75 0.25 | 0.25 0.75 | 1 0.5 | 0.5 1 | 0.75 0.75 | 1 1 | 0.5 1.5 | 1.5 0.5 | 2 0.5 | 0.5 2 | 2.5 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 0 |
| Unwanted plants: | | | | | | | | | | | | | |
| Setaria faberii | 77 | 98 | 87 | 100 | 100 | 100 | 100 | 100 | 100 | 100 | 100 | 100 | 100 |
| Lamium amplexicaule | 45 | 50 | 60 | 47 | 65 | 53 | 62 | 75 | 63 | 80 | 95 | 80 | 100 |
| Amaranthus retroflexus | 60 | 76 | 75 | 75 | 87 | 95 | 90 | 100 | 100 | 100 | 100 | 100 | 100 |

| kg/ha | 0.25 2.5 | 0.5 2.5 | 2.5 0.5 | 1.5 1.5 | 1 3 | 3 1 | 2 2 |
|---|---|---|---|---|---|---|---|
| Glycine max | 6 | 6 | 5 | 0 | 12 | 10 | 0 |
| Setaria faberii | 100 | 100 | 100 | 100 | 100 | 100 | 100 |
| Lamium amplexicaule | 70 | 72 | 100 | 89 | 100 | 100 | 100 |
| Amaranthus retroflexus | 100 | 100 | 100 | 100 | 100 | 100 | 100 |

II + V

| kg/ha | 0.25 0.25 | 0.5 0.5 | 0.75 0.25 | 0.25 0.75 | 1 0.5 | 0.5 1 | 0.75 0.75 | 1 1 | 0.5 1.5 | 1.5 0.5 | 2 0.5 | 0.5 2 | 2.5 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 63 | 76 | 70 | 86 | 88 | 100 | 95 | 100 | 100 | 96 | 100 | 100 | 100 |
| Lamium amplexicaule | 45 | 54 | 63 | 60 | 70 | 70 | 75 | 85 | 85 | 90 | 100 | 95 | 98 |
| Amaranthus retroflexus | 60 | 70 | 85 | 75 | 96 | 89 | 98 | 100 | 100 | 100 | 100 | 100 | 100 |

| kg/ha | 0.25 2.5 | 0.5 2.5 | 2.5 0.5 | 1.5 1.5 | 1 3 | 3 1 | 2 2 | 2 1 | 1 2 |
|---|---|---|---|---|---|---|---|---|---|
| Glycine max | 0 | 0 | 5 | 0 | 7 | 15 | 0 | 0 | 0 |
| Setaria faberii | 100 | 100 | 100 | 100 | 100 | 100 | 100 | 100 | 100 |
| Lamium amplexicaule | 96 | 98 | 100 | 100 | 100 | 100 | 100 | 100 | 100 |
| Amaranthus retroflexus | 100 | 100 | 100 | 100 | 100 | 100 | 100 | 100 | 100 |

II + VI

| kg/ha | 0.25 0.25 | 0.5 0.5 | 0.75 0.25 | 0.25 0.75 | 1 0.5 | 0.5 1 | 0.75 0.75 | 1 1 | 0.5 1.5 | 1.5 0.5 | 2 0.5 | 0.5 2 | 2.5 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 58 | 70 | 65 | 83 | 85 | 96 | 90 | 100 | 100 | 95 | 100 | 100 | 100 |
| Lamium amplexicaule | 46 | 50 | 60 | 60 | 71 | 70 | 70 | 85 | 88 | 85 | 96 | 98 | 98 |
| Amaranthus retroflexus | 60 | 70 | 83 | 70 | 97 | 85 | 95 | 100 | 100 | 100 | 100 | 100 | 100 |

| kg/ha | 0.25 2.5 | 0.5 2.5 | 2.5 0.5 | 1.5 1.5 | 1 3 | 3 1 | 2 2 |
|---|---|---|---|---|---|---|---|
| Glycine max | 3 | 3 | 5 | 0 | 10 | 15 | 0 |
| Setaria faberii | 100 | 100 | 100 | 100 | 100 | 100 | 100 |
| Lamium amplexicaule | 100 | 100 | 100 | 100 | 100 | 100 | 100 |
| Amaranthus retroflexus | 100 | 100 | 100 | 100 | 100 | 100 | 100 |

II + VII

| kg/ha | 0.25 0.25 | 0.5 0.5 | 0.75 0.25 | 0.25 0.75 | 1 0.5 | 0.5 1 | 0.75 0.75 | 1 1 | 0.5 1.5 | 1.5 0.5 | 2 0.5 | 0.5 2 | 2.5 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 58 | 65 | 65 | 74 | 75 | 86 | 80 | 95 | 100 | 88 | 89 | 100 | 90 |
| Lamium amplexicaule | 46 | 52 | 60 | 47 | 65 | 65 | 65 | 80 | 70 | 84 | 87 | 75 | 95 |
| Amaranthus retroflexus | 50 | 55 | 75 | 53 | 85 | 63 | 75 | 90 | 75 | 100 | 100 | 91 | 100 |

-continued

| kg/ha | 0.25 | 0.5 | 2.5 | 1.5 | 1 | 3 | 2 | | | | | | |
|---|---|---|---|---|---|---|---|---|---|---|---|---|---|
| | 2.5 | 2.5 | 0.5 | 1.5 | 3 | 1 | 2 | | | | | | |
| Glycine max | 0 | 0 | 5 | 0 | 5 | 15 | 0 | | | | | | |
| Setaria faberii | 100 | 100 | 96 | 100 | 100 | 100 | 100 | | | | | | |
| Lamium amplexicaule | 70 | 78 | 98 | 100 | 100 | 100 | 100 | | | | | | |
| Amaranthus retroflexus | 96 | 100 | 100 | 100 | 100 | 100 | 100 | | | | | | |

II + VIII

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 61 | 78 | 76 | 75 | 85 | 84 | 80 | 95 | 100 | 95 | 95 | 100 | 100 |
| Lamium amplexicaule | 45 | 50 | 60 | 49 | 65 | 60 | 60 | 70 | 65 | 85 | 95 | 68 | 98 |
| Amaranthus retroflexus | 50 | 55 | 72 | 53 | 86 | 70 | 75 | 95 | 75 | 100 | 100 | 90 | 100 |

| kg/ha | 0.25 | 0.5 | 2.5 | 1.5 | 1 | 3 | 2 | | | | | | |
|---|---|---|---|---|---|---|---|---|---|---|---|---|---|
| | 2.5 | 2.5 | 0.5 | 1.5 | 3 | 1 | 2 | | | | | | |
| Glycine max | 0 | 0 | 5 | 0 | 4 | 15 | 0 | | | | | | |
| Setaria faberii | 100 | 100 | 100 | 100 | 100 | 100 | 100 | | | | | | |
| Lamium amplexicaule | 80 | 83 | 98 | 97 | 100 | 100 | 100 | | | | | | |
| Amaranthus retroflexus | 95 | 100 | 100 | 100 | 100 | 100 | 100 | | | | | | |

II + IX

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 60 | 74 | 70 | 80 | 85 | 98 | 90 | 100 | 100 | 98 | 100 | 100 | 92 |
| Lamium amplexicaule | 45 | 50 | 60 | 47 | 65 | 60 | 60 | 68 | 67 | 84 | 96 | 80 | 97 |
| Amaranthus retroflexus | 50 | 55 | 70 | 53 | 84 | 70 | 75 | 91 | 80 | 100 | 100 | 95 | 100 |

| kg/ha | 0.25 | 0.5 | 2.5 | 1.5 | 1 | 3 | 2 | 2 | 1 | | | | |
|---|---|---|---|---|---|---|---|---|---|---|---|---|---|
| | 2.5 | 2.5 | 0.5 | 1.5 | 3 | 1 | 2 | 1 | 2 | | | | |
| Glycine max | 0 | 0 | 5 | 0 | 6 | 15 | 0 | 0 | 0 | | | | |
| Setaria faberii | 100 | 100 | 100 | 100 | 100 | 100 | 100 | 100 | 100 | | | | |
| Lamium amplexicaule | 80 | 80 | 97 | 98 | 98 | 100 | 100 | 100 | 100 | | | | |
| Amaranthus retroflexus | 95 | 100 | 100 | 100 | 100 | 100 | 100 | 100 | 100 | | | | |

II + X

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 66 | 80 | 75 | 90 | 93 | 100 | 97 | 100 | 100 | 98 | 100 | 100 | 100 |
| Lamium amplexicaule | 44 | 57 | 60 | 60 | 70 | 75 | 73 | 90 | 90 | 91 | 100 | 100 | 100 |
| Amaranthus retroflexus | 65 | 75 | 87 | 80 | 100 | 91 | 100 | 100 | 100 | 100 | 100 | 100 | 100 |

| kg/ha | 0.25 | 0.5 | 2.5 | 1.5 | 1 | 3 | 2 | | | | | | |
|---|---|---|---|---|---|---|---|---|---|---|---|---|---|
| | 2.5 | 2.5 | 0.5 | 1.5 | 3 | 1 | 2 | | | | | | |
| Glycine max | 5 | 5 | 5 | 0 | 10 | 15 | 0 | | | | | | |
| Setaria faberii | 100 | 100 | 100 | 100 | 100 | 100 | 100 | | | | | | |
| Lamium amplexicaule | 100 | 100 | 100 | 100 | 100 | 100 | 100 | | | | | | |
| Amaranthus retroflexus | 100 | 100 | 100 | 100 | 100 | 100 | 100 | | | | | | |

II + XI

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 62 | 74 | 70 | 85 | 87 | 100 | 93 | 100 | 100 | 95 | 97 | 100 | 95 |
| Lamium amplexicaule | 45 | 57 | 61 | 60 | 72 | 70 | 75 | 85 | 83 | 91 | 100 | 85 | 100 |
| Amaranthus retroflexus | 60 | 62 | 85 | 70 | 100 | 88 | 95 | 100 | 100 | 100 | 100 | 100 | 100 |

| kg/ha | 0.25 | 0.5 | 2.5 | 1.5 | 1 | 3 | 2 | | | | | | |
|---|---|---|---|---|---|---|---|---|---|---|---|---|---|
| | 2.5 | 2.5 | 0.5 | 1.5 | 3 | 1 | 2 | | | | | | |
| Glycine max | 0 | 0 | 5 | 0 | 6 | 15 | 0 | | | | | | |
| Setaria faberii | 100 | 100 | 100 | 100 | 100 | 100 | 100 | | | | | | |
| Lamium amplexicaule | 87 | 90 | 100 | 100 | 100 | 100 | 100 | | | | | | |
| Amaranthus retroflexus | 100 | 100 | 100 | 100 | 100 | 100 | 100 | | | | | | |

II + XII

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |
| Crop plant: | | | | | | | | | | | | | |
| Glycine max | 0 | 0 | 0 | 0 | 0 | 0 | 0 | 0 | 0 | 0 | 0 | 0 | 5 |

-continued

| | | | | | | | | | | | | | |
|---|---|---|---|---|---|---|---|---|---|---|---|---|---|
| Unwanted plants: | | | | | | | | | | | | | |
| Setaria faberii | 75 | 86 | 85 | 96 | 98 | 100 | 100 | 100 | 100 | 100 | 100 | 100 | 100 |
| Lamium amplexicaule | 47 | 57 | 60 | 60 | 72 | 70 | 75 | 80 | 80 | 91 | 97 | 93 | 97 |
| Amaranthus retroflexus | 55 | 65 | 78 | 70 | 90 | 80 | 93 | 100 | 95 | 100 | 100 | 100 | 100 |

| kg/ha | 0.25 / 2.5 | 0.5 / 2.5 | 2.5 / 0.5 | 1.5 / 1.5 | 1 / 3 | 3 / 1 | 2 / 2 | | | | | | |
|---|---|---|---|---|---|---|---|---|---|---|---|---|---|
| Glycine max | 0 | 0 | 5 | 0 | 5 | 15 | 0 | | | | | | |
| Setaria faberii | 100 | 100 | 100 | 100 | 100 | 100 | 100 | | | | | | |
| Lamium amplexicaule | 97 | 98 | 100 | 100 | 100 | 100 | 100 | | | | | | |
| Amaranthus retroflexus | 100 | 100 | 100 | 100 | 100 | 100 | 100 | | | | | | |

II + XIII

| kg/ha | 0.25 / 0.25 | 0.5 / 0.5 | 0.75 / 0.25 | 0.25 / 0.75 | 1 / 0.5 | 0.5 / 1 | 0.75 / 0.75 | 1 / 1 | 0.5 / 1.5 | 1.5 / 0.5 | 2 / 0.5 | 0.5 / 2 | 2.5 / 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 5 |
| Setaria faberii | 61 | 79 | 70 | 90 | 92 | 97 | 96 | 100 | 100 | 100 | 100 | 100 | 100 |
| Lamium amplexicaule | 45 | 50 | 56 | 55 | 65 | 67 | 70 | 80 | 75 | 84 | 90 | 80 | 96 |
| Amaranthus retroflexus | 49 | 56 | 73 | 62 | 88 | 75 | 87 | 100 | 89 | 100 | 100 | 96 | 100 |

| kg/ha | 0.25 / 2.5 | 0.5 / 2.5 | 2.5 / 0.5 | 1.5 / 1.5 | 1 / 3 | 3 / 1 | 2 / 2 | 2 / 1 | 1 / 2 | | | | |
|---|---|---|---|---|---|---|---|---|---|---|---|---|---|
| Glycine max | 0 | 0 | 5 | 0 | 4 | 15 | 0 | 0 | 0 | | | | |
| Setaria faberii | 100 | 100 | 100 | 100 | 100 | 100 | 100 | 100 | 100 | | | | |
| Lamium amplexicaule | 80 | 83 | 98 | 100 | 100 | 100 | 100 | 100 | 90 | | | | |
| Amaranthus retroflexus | 95 | 100 | 100 | 100 | 100 | 100 | 100 | 100 | 100 | | | | |

II + XIV

| kg/ha | 0.25 / 0.25 | 0.5 / 0.5 | 0.75 / 0.25 | 0.25 / 0.75 | 1 / 0.5 | 0.5 / 1 | 0.75 / 0.75 | 1 / 1 | 0.5 / 1.5 | 1.5 / 0.5 | 2 / 0.5 | 0.5 / 2 | 2.5 / 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 60 | 74 | 71 | 81 | 85 | 95 | 90 | 100 | 100 | 96 | 98 | 100 | 98 |
| Lamium amplexicaule | 46 | 50 | 57 | 49 | 63 | 60 | 62 | 74 | 70 | 82 | 95 | 78 | 96 |
| Amaranthus retroflexus | 56 | 70 | 80 | 70 | 97 | 85 | 95 | 100 | 98 | 100 | 100 | 100 | 100 |

| kg/ha | 0.25 / 2.5 | 0.5 / 2.5 | 2.5 / 0.5 | 1.5 / 1.5 | 1 / 3 | 3 / 1 | 2 / 2 | | | | | | |
|---|---|---|---|---|---|---|---|---|---|---|---|---|---|
| Glycine max | 3 | 3 | 5 | 0 | 10 | 15 | 0 | | | | | | |
| Setaria faberii | 100 | 100 | 100 | 100 | 100 | 100 | 100 | | | | | | |
| Lamium amplexicaule | 85 | 80 | 98 | 100 | 100 | 100 | 100 | | | | | | |
| Amaranthus retroflexus | 100 | 100 | 100 | 100 | 100 | 100 | 100 | | | | | | |

II + XV

| kg/ha | 0.25 / 0.25 | 0.5 / 0.5 | 0.75 / 0.25 | 0.25 / 0.75 | 1 / 0.5 | 0.5 / 1 | 0.75 / 0.75 | 1 / 1 | 0.5 / 1.5 | 1.5 / 0.5 | 2 / 0.5 | 0.5 / 2 | 2.5 / 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 57 | 66 | 65 | 77 | 75 | 98 | 95 | 100 | 100 | 84 | 90 | 100 | 95 |
| Lamium amplexicaule | 45 | 51 | 60 | 48 | 65 | 57 | 60 | 65 | 66 | 82 | 95 | 69 | 96 |
| Amaranthus retroflexus | 50 | 55 | 73 | 53 | 82 | 65 | 76 | 84 | 77 | 100 | 100 | 90 | 100 |

| kg/ha | 0.25 / 2.5 | 0.5 / 2.5 | 2.5 / 0.5 | 1.5 / 1.5 | 1 / 3 | 3 / 1 | 2 / 2 | 2 / 1 | 1 / 2 | | | | |
|---|---|---|---|---|---|---|---|---|---|---|---|---|---|
| Glycine max | 0 | 0 | 5 | 0 | 4 | 15 | 0 | 0 | 0 | | | | |
| Setaria faberii | 100 | 100 | 100 | 100 | 100 | 100 | 100 | 100 | 100 | | | | |
| Lamium amplexicaule | 70 | 75 | 97 | 95 | 95 | 100 | 100 | 97 | 75 | | | | |
| Amaranthus retroflexus | 95 | 95 | 100 | 100 | 100 | 100 | 100 | 100 | 100 | | | | |

II + XVI

| kg/ha | 0.25 / 0.25 | 0.5 / 0.5 | 0.75 / 0.25 | 0.25 / 0.75 | 1 / 0.5 | 0.5 / 1 | 0.75 / 0.75 | 1 / 1 | 0.5 / 1.5 | 1.5 / 0.5 | 2 / 0.5 | 0.5 / 2 | 2.5 / 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 63 | 75 | 70 | 80 | 85 | 97 | 90 | 100 | 100 | 96 | 98 | 100 | 95 |
| Lamium amplexicaule | 47 | 50 | 60 | 49 | 65 | 60 | 60 | 70 | 65 | 81 | 96 | 75 | 97 |
| Amaranthus retroflexus | 50 | 55 | 73 | 50 | 85 | 69 | 75 | 95 | 78 | 100 | 100 | 90 | 100 |

| kg/ha | 0.25 / 2.5 | 0.5 / 2.5 | 2.5 / 0.5 | 1.5 / 1.5 | 1 / 3 | 3 / 1 | 2 / 2 | | | | | | |
|---|---|---|---|---|---|---|---|---|---|---|---|---|---|
| Glycine max | 0 | 0 | 5 | 0 | 5 | 15 | 0 | | | | | | |
| Setaria faberii | 100 | 100 | 100 | 100 | 100 | 100 | 100 | | | | | | |
| Lamium amplexicaule | 75 | 79 | 98 | 98 | 97 | 100 | 100 | | | | | | |
| Amaranthus retroflexus | 95 | 100 | 100 | 100 | 100 | 100 | 100 | | | | | | |

II + XVII

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|

-continued

| kg/ha | 0.25 | 0.5 | 0.25 | 0.75 | 0.5 | 1 | 0.75 | 1 | 1.5 | 0.5 | 0.5 | 2 | 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 80 | 92 | 90 | 100 | 100 | 100 | 100 | 100 | 100 | 100 | 100 | 100 | 100 |
| Lamium amplexicaule | 45 | 50 | 60 | 47 | 61 | 60 | 60 | 75 | 65 | 80 | 95 | 70 | 96 |
| Amaranthus retroflexus | 55 | 63 | 75 | 70 | 90 | 85 | 92 | 100 | 100 | 100 | 100 | 100 | 100 |

| kg/ha | 0.25 | 0.5 | 2.5 | 1.5 | 1 | 3 | 2 |
|---|---|---|---|---|---|---|---|
| | 2.5 | 2.5 | 0.5 | 1.5 | 3 | 1 | 2 |
| Glycine max | 5 | 5 | 5 | 0 | 10 | 15 | 0 |
| Setaria faberii | 100 | 100 | 100 | 100 | 100 | 100 | 100 |
| Lamium amplexicaule | 75 | 80 | 97 | 96 | 97 | 100 | 100 |
| Amaranthus retroflexus | 100 | 100 | 100 | 100 | 100 | 100 | 100 |

II + XVIII

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |
| Crop plant: | | | | | | | | | | | | | |
| Glycine max | 0 | 0 | 0 | 0 | 0 | 0 | 0 | 0 | 0 | 0 | 0 | 0 | 0 |
| Unwanted plants: | | | | | | | | | | | | | |
| Setaria faberii | 79 | 98 | 90 | 100 | 100 | 100 | 100 | 100 | 100 | 100 | 100 | 100 | 100 |
| Lamium amplexicaule | 48 | 50 | 60 | 79 | 63 | 60 | 60 | 65 | 70 | 80 | 95 | 70 | 96 |
| Amaranthus retroflexus | 52 | 62 | 75 | 65 | 97 | 80 | 90 | 100 | 100 | 100 | 100 | 100 | 100 |

| kg/ha | 0.25 | 0.5 | 2.5 | 1.5 | 1 | 3 | 2 |
|---|---|---|---|---|---|---|---|
| | 2.5 | 2.5 | 0.5 | 1.5 | 3 | 1 | 2 |
| Glycine max | 6 | 6 | 5 | 0 | 12 | 15 | 0 |
| Setaria faberii | 100 | 100 | 100 | 100 | 100 | 100 | 100 |
| Lamium amplexicaule | 70 | 75 | 96 | 96 | 95 | 100 | 100 |
| Amaranthus retroflexus | 100 | 100 | 100 | 100 | 100 | 100 | 100 |

III + V

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |
| Crop plant: | | | | | | | | | | | | | |
| Glycine max | 0 | 0 | 0 | 0 | 0 | 0 | 0 | 0 | 0 | 0 | 0 | 0 | 7 |
| Unwanted plants: | | | | | | | | | | | | | |
| Setaria faberii | 56 | 75 | 65 | 82 | 80 | 100 | 90 | 100 | 100 | 90 | 100 | 100 | 100 |
| Lamium amplexicaule | 45 | 60 | 60 | 60 | 75 | 70 | 75 | 90 | 85 | 90 | 98 | 86 | 98 |
| Amaranthus retroflexus | 65 | 80 | 90 | 78 | 100 | 95 | 100 | 100 | 100 | 100 | 100 | 100 | 100 |

| kg/ha | 0.25 | 0.5 | 2.5 | 1.5 | 1 | 3 | 2 | 2 | 1 |
|---|---|---|---|---|---|---|---|---|---|
| | 2.5 | 2.5 | 0.5 | 1.5 | 3 | 1 | 2 | 1 | 2 |
| Glycine max | 0 | 0 | 7 | 0 | 7 | 12 | 0 | 0 | 0 |
| Setaria faberii | 100 | 100 | 100 | 100 | 100 | 100 | 100 | 100 | 100 |
| Lamium amplexicaule | 98 | 100 | 100 | 100 | 100 | 100 | 100 | 100 | 100 |
| Amaranthus retroflexus | 100 | 100 | 100 | 100 | 100 | 100 | 100 | 100 | |

III + VI

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |
| Crop plant: | | | | | | | | | | | | | |
| Glycine max | 0 | 0 | 0 | 0 | 0 | 0 | 0 | 0 | 0 | 0 | 0 | 0 | 7 |
| Unwanted plants: | | | | | | | | | | | | | |
| Setaria faberii | 60 | 75 | 66 | 80 | 86 | 100 | 92 | 100 | 100 | 95 | 100 | 100 | 100 |
| Lamium amplexicaule | 45 | 60 | 60 | 62 | 75 | 70 | 75 | 90 | 85 | 90 | 98 | 95 | 98 |
| Amaranthus retroflexus | 62 | 80 | 90 | 80 | 100 | 93 | 98 | 100 | 100 | 100 | 100 | 100 | 100 |

| kg/ha | 0.25 | 0.5 | 2.5 | 1.5 | 1 | 3 | 2 |
|---|---|---|---|---|---|---|---|
| | 2.5 | 2.5 | 0.5 | 1.5 | 3 | 1 | 2 |
| Glycine max | 3 | 3 | 7 | 0 | 10 | 12 | 0 |
| Setaria faberii | 100 | 100 | 100 | 100 | 100 | 100 | 100 |
| Lamium amplexicaule | 98 | 100 | 100 | 100 | 100 | 100 | 100 |
| Amaranthus retroflexus | 100 | 100 | 100 | 100 | 100 | 100 | 100 |

III + VII

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |
| Crop plant: | | | | | | | | | | | | | |
| Glycine max | 0 | 0 | 0 | 0 | 0 | 0 | 0 | 0 | 0 | 0 | 0 | 0 | 7 |
| Unwanted plants: | | | | | | | | | | | | | |
| Setaria faberii | 55 | 65 | 62 | 70 | 74 | 85 | 77 | 88 | 100 | 85 | 90 | 100 | 90 |
| Lamium amplexicaule | 48 | 50 | 60 | 48 | 70 | 65 | 70 | 85 | 70 | 82 | 90 | 75 | 95 |
| Amaranthus retroflexus | 55 | 63 | 76 | 60 | 90 | 75 | 80 | 97 | 90 | 100 | 100 | 98 | 100 |

| kg/ha | 0.25 | 0.5 | 2.5 | 1.5 | 1 | 3 | 2 |
|---|---|---|---|---|---|---|---|
| | 2.5 | 2.5 | 0.5 | 1.5 | 3 | 1 | 2 |
| Glycine max | 0 | 0 | 7 | 0 | 5 | 12 | 0 |
| Setaria faberii | 100 | 100 | 95 | 100 | 100 | 100 | 100 |
| Lamium amplexicaule | 77 | 78 | 97 | 100 | 100 | 100 | 100 |

| Amaranthus retroflexus | 100 | 100 | 100 | 100 | 100 | 100 | 100 | | | | | | |

III + VIII

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |

| Crop plant: | | | | | | | | | | | | | |
|---|---|---|---|---|---|---|---|---|---|---|---|---|---|
| Glycine max | 0 | 0 | 0 | 0 | 0 | 0 | 0 | 0 | 0 | 0 | 0 | 0 | 7 |
| Unwanted plants: | | | | | | | | | | | | | |
| Setaria faberii | 56 | 70 | 65 | 69 | 75 | 85 | 75 | 90 | 100 | 85 | 90 | 100 | 91 |
| Lamium amplexicaule | 45 | 50 | 60 | 47 | 67 | 60 | 64 | 75 | 69 | 83 | 92 | 76 | 96 |
| Amaranthus retroflexus | 55 | 63 | 75 | 58 | 89 | 77 | 80 | 95 | 90 | 100 | 100 | 97 | 100 |

| kg/ha | 0.25 | 0.5 | 2.5 | 1.5 | 1 | 3 | 2 |
|---|---|---|---|---|---|---|---|
| | 2.5 | 2.5 | 0.5 | 1.5 | 3 | 1 | 2 |

| Glycine max | 0 | 0 | 7 | 0 | 4 | 12 | 0 |
|---|---|---|---|---|---|---|---|
| Setaria faberii | 100 | 100 | 100 | 100 | 100 | 100 | 100 |
| Lamium amplexicaule | 86 | 85 | 98 | 98 | 100 | 100 | 100 |
| Amaranthus retroflexus | 95 | 100 | 100 | 100 | 100 | 100 | 100 |

III + IX

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |

| Crop plant: | | | | | | | | | | | | | |
|---|---|---|---|---|---|---|---|---|---|---|---|---|---|
| Glycine max | 0 | 0 | 0 | 0 | 0 | 0 | 0 | 0 | 0 | 0 | 0 | 0 | 7 |
| Unwanted plants: | | | | | | | | | | | | | |
| Setaria faberii | 60 | 64 | 65 | 77 | 80 | 90 | 90 | 100 | 100 | 90 | 98 | 100 | 92 |
| Lamium amplexicaule | 45 | 50 | 57 | 50 | 65 | 60 | 65 | 73 | 67 | 82 | 92 | 85 | 96 |
| Amaranthus retroflexus | 53 | 63 | 75 | 60 | 90 | 76 | 78 | 96 | 90 | 100 | 100 | 100 | 100 |

| kg/ha | 0.25 | 0.5 | 2.5 | 1.5 | 1 | 3 | 2 | 2 | 1 |
|---|---|---|---|---|---|---|---|---|---|
| | 2.5 | 2.5 | 0.5 | 1.5 | 3 | 1 | 2 | 1 | 2 |

| Glycine max | 0 | 0 | 7 | 0 | 6 | 12 | 0 | 0 | 0 |
|---|---|---|---|---|---|---|---|---|---|
| Setaria faberii | 100 | 100 | 100 | 100 | 100 | 100 | 100 | 100 | 100 |
| Lamium amplexicaule | 77 | 83 | 96 | 95 | 97 | 100 | 100 | 100 | 100 |
| Amaranthus retroflexus | 95 | 100 | 100 | 100 | 100 | 100 | 100 | 100 | 100 |

III + X

| kg/ha | 0.25 | 0.5 | 0.75 | 0.25 | 1 | 0.5 | 0.75 | 1 | 0.5 | 1.5 | 2 | 0.5 |
|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 |

| Crop plant: | | | | | | | | | | | | |
|---|---|---|---|---|---|---|---|---|---|---|---|---|
| Glycine max | 0 | 0 | 0 | 0 | 0 | 0 | 0 | 0 | 0 | 0 | 0 | 0 |
| Unwanted plants: | | | | | | | | | | | | |
| Setaria faberii | 64 | 75 | 72 | 85 | 87 | 100 | 95 | 100 | 100 | 98 | 100 | 100 |
| Lamium amplexicaule | 46 | 57 | 60 | 62 | 75 | 70 | 95 | 90 | 90 | 93 | 98 | 100 |
| Amaranthus retroflexus | 68 | 82 | 90 | 85 | 100 | 100 | 100 | 100 | 100 | 100 | 100 | 100 |

| kg/ha | 2.5 | 0.25 | 0.5 | 2.5 | 1.5 | 1 | 3 | 2 |
|---|---|---|---|---|---|---|---|---|
| | 0.25 | 2.5 | 2.5 | 0.5 | 1.5 | 3 | 1 | 2 |

| Crop plant: | | | | | | | | |
|---|---|---|---|---|---|---|---|---|
| Glycine max | 7 | 5 | 5 | 7 | 0 | 10 | 12 | 0 |
| Unwanted plants: | | | | | | | | |
| Setaria faberii | 100 | 100 | 100 | 100 | 100 | 100 | 100 | 100 |
| Lamium amplexicaule | 95 | 100 | 100 | 100 | 100 | 100 | 100 | 100 |
| Amaranthus retroflexus | 100 | 100 | 100 | 100 | 100 | 100 | 100 | 100 |

III + XI

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |

| Crop plant: | | | | | | | | | | | | | |
|---|---|---|---|---|---|---|---|---|---|---|---|---|---|
| Glycine max | 0 | 0 | 0 | 0 | 0 | 0 | 0 | 0 | 0 | 0 | 0 | 0 | 7 |
| Unwanted plants: | | | | | | | | | | | | | |
| Setaria faberii | 60 | 73 | 67 | 80 | 84 | 95 | 92 | 100 | 93 | 92 | 96 | 100 | 100 |
| Lamium amplexicaule | 45 | 57 | 60 | 60 | 75 | 70 | 75 | 90 | 92 | 95 | 98 | 100 | 100 |
| Amaranthus retroflexus | 53 | 80 | 88 | 76 | 100 | 95 | 98 | 100 | 100 | 100 | 100 | 100 | 100 |

| kg/ha | 0.25 | 0.5 | 2.5 | 1.5 | 1 | 3 | 2 |
|---|---|---|---|---|---|---|---|
| | 2.5 | 2.5 | 0.5 | 1.5 | 3 | 1 | 2 |

| Glycine max | 0 | 0 | 7 | 0 | 6 | 12 | 0 |
|---|---|---|---|---|---|---|---|
| Setaria faberii | 100 | 100 | 100 | 100 | 100 | 100 | 100 |
| Lamium amplexicaule | 100 | 100 | 100 | 100 | 100 | 100 | 100 |
| Amaranthus retroflexus | 100 | 100 | 100 | 100 | 100 | 100 | 100 |

III + XII

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |

| Crop plant: | | | | | | | | | | | | | |
|---|---|---|---|---|---|---|---|---|---|---|---|---|---|
| Glycine max | 0 | 0 | 0 | 0 | 0 | 0 | 0 | 0 | 0 | 0 | 0 | 0 | 7 |
| Unwanted plants: | | | | | | | | | | | | | |
| Setaria faberii | 70 | 80 | 80 | 95 | 95 | 100 | 100 | 100 | 100 | 100 | 100 | 100 | 100 |
| Lamium amplexicaule | 45 | 55 | 60 | 60 | 75 | 70 | 75 | 90 | 80 | 92 | 95 | 93 | 97 |

-continued

| | | | | | | | | | | | | | |
|---|---|---|---|---|---|---|---|---|---|---|---|---|---|
| Amaranthus retroflexus | 60 | 70 | 80 | 75 | 95 | 90 | 97 | 100 | 100 | 100 | 100 | 100 | 100 |

| kg/ha | 0.25 | 0.5 | 2.5 | 1.5 | 1 | 3 | 2 |
|---|---|---|---|---|---|---|---|
| | 2.5 | 2.5 | 0.5 | 1.5 | 3 | 1 | 2 |

Crop plant:
| | | | | | | | |
|---|---|---|---|---|---|---|---|
| Glycine max | 0 | 0 | 7 | 0 | 5 | 12 | 0 |
| Setaria faberii | 100 | 100 | 100 | 100 | 100 | 100 | 100 |
| Lamium amplexicaule | 96 | 98 | 100 | 100 | 100 | 100 | 100 |
| Amaranthus retroflexus | 100 | 100 | 100 | 100 | 100 | 100 | 100 |

III + XIII

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |

Crop plant:
| | | | | | | | | | | | | | |
|---|---|---|---|---|---|---|---|---|---|---|---|---|---|
| Glycine max | 0 | 0 | 0 | 0 | 0 | 0 | 0 | 0 | 0 | 0 | 0 | 0 | 7 |

Unwanted plants:
| | | | | | | | | | | | | | |
|---|---|---|---|---|---|---|---|---|---|---|---|---|---|
| Setaria faberii | 59 | 75 | 76 | 85 | 87 | 100 | 97 | 100 | 100 | 98 | 100 | 100 | 100 |
| Lamium amplexicaule | 46 | 50 | 60 | 55 | 63 | 67 | 70 | 85 | 80 | 85 | 90 | 85 | 95 |
| Amaranthus retroflexus | 53 | 70 | 75 | 67 | 80 | 82 | 90 | 100 | 95 | 100 | 100 | 100 | 100 |

| kg/ha | 0.25 | 0.5 | 2.5 | 1.5 | 1 | 3 | 2 | 2 | 1 |
|---|---|---|---|---|---|---|---|---|---|
| | 2.5 | 2.5 | 0.5 | 1.5 | 3 | 1 | 2 | 1 | 2 |

| | | | | | | | | | |
|---|---|---|---|---|---|---|---|---|---|
| Glycine max | 0 | 0 | 7 | 0 | 4 | 12 | 0 | 0 | 0 |
| Setaria faberii | 100 | 100 | 100 | 100 | 100 | 100 | 100 | 100 | 100 |
| Lamium amplexicaule | 80 | 80 | 100 | 100 | 100 | 100 | 100 | 100 | 95 |
| Amaranthus retroflexus | 100 | 100 | 100 | 100 | 100 | 100 | 100 | 100 | 100 |

III + XIV

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |

Crop plant:
| | | | | | | | | | | | | | |
|---|---|---|---|---|---|---|---|---|---|---|---|---|---|
| Glycine max | 0 | 0 | 0 | 0 | 0 | 0 | 0 | 0 | 0 | 0 | 0 | 0 | 7 |

Unwanted plants:
| | | | | | | | | | | | | | |
|---|---|---|---|---|---|---|---|---|---|---|---|---|---|
| Setaria faberii | 61 | 75 | 66 | 78 | 80 | 92 | 85 | 98 | 100 | 93 | 97 | 100 | 100 |
| Lamium amplexicaule | 45 | 49 | 58 | 48 | 67 | 60 | 62 | 80 | 70 | 85 | 92 | 82 | 95 |
| Amaranthus retroflexus | 62 | 78 | 86 | 75 | 100 | 94 | 97 | 100 | 100 | 100 | 100 | 100 | 100 |

| kg/ha | 0.25 | 0.5 | 2.5 | 1.5 | 1 | 3 | 2 |
|---|---|---|---|---|---|---|---|
| | 2.5 | 2.5 | 0.5 | 1.5 | 3 | 1 | 2 |

| | | | | | | | | |
|---|---|---|---|---|---|---|---|---|
| Glycine max | 3 | 3 | 7 | 0 | 10 | 12 | 0 |
| Setaria faberii | 100 | 100 | 100 | 100 | 100 | 100 | 100 |
| Lamium amplexicaule | 85 | 87 | 97 | 100 | 100 | 100 | 100 |
| Amaranthus retroflexus | 100 | 100 | 100 | 100 | 100 | 100 | 100 |

III + XV

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |

Crop plant:
| | | | | | | | | | | | | | |
|---|---|---|---|---|---|---|---|---|---|---|---|---|---|
| Glycine max | 0 | 0 | 0 | 0 | 0 | 0 | 0 | 0 | 0 | 0 | 0 | 0 | 7 |

Unwanted plants:
| | | | | | | | | | | | | | |
|---|---|---|---|---|---|---|---|---|---|---|---|---|---|
| Setaria faberii | 55 | 65 | 63 | 73 | 75 | 90 | 80 | 100 | 100 | 85 | 90 | 100 | 95 |
| Lamium amplexicaule | 45 | 50 | 60 | 50 | 68 | 60 | 60 | 70 | 70 | 92 | 90 | 70 | 95 |
| Amaranthus retroflexus | 55 | 65 | 75 | 55 | 89 | 75 | 80 | 90 | 91 | 100 | 100 | 95 | 100 |

| kg/ha | 0.25 | 0.5 | 2.5 | 1.5 | 1 | 3 | 2 | 2 | 1 |
|---|---|---|---|---|---|---|---|---|---|
| | 2.5 | 2.5 | 0.5 | 1.5 | 3 | 1 | 2 | 1 | 2 |

| | | | | | | | | | |
|---|---|---|---|---|---|---|---|---|---|
| Glycine max | 0 | 0 | 7 | 0 | 4 | 12 | 0 | 0 | 0 |
| Setaria faberii | 100 | 100 | 98 | 100 | 100 | 100 | 100 | 100 | 100 |
| Lamium amplexicaule | 72 | 75 | 95 | 95 | 100 | 100 | 100 | 93 | 80 |
| Amaranthus retroflexus | 94 | 95 | 100 | 100 | 100 | 100 | 100 | 100 | 100 |

III + XVI

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |

Crop plant:
| | | | | | | | | | | | | | |
|---|---|---|---|---|---|---|---|---|---|---|---|---|---|
| Glycine max | 0 | 0 | 0 | 0 | 0 | 0 | 0 | 0 | 0 | 0 | 0 | 0 | 7 |

Unwanted plants:
| | | | | | | | | | | | | | |
|---|---|---|---|---|---|---|---|---|---|---|---|---|---|
| Setaria faberii | 60 | 73 | 70 | 77 | 80 | 96 | 85 | 100 | 100 | 95 | 98 | 100 | 95 |
| Lamium amplexicaule | 46 | 50 | 60 | 49 | 70 | 60 | 62 | 75 | 70 | 85 | 90 | 75 | 95 |
| Amaranthus retroflexus | 57 | 62 | 76 | 60 | 89 | 77 | 78 | 98 | 90 | 100 | 100 | 100 | 100 |

| kg/ha | 0.25 | 0.5 | 2.5 | 1.5 | 1 | 3 | 2 |
|---|---|---|---|---|---|---|---|
| | 2.5 | 2.5 | 0.5 | 1.5 | 3 | 1 | 2 |

| | | | | | | | | |
|---|---|---|---|---|---|---|---|---|
| Glycine max | 0 | 0 | 7 | 0 | 5 | 12 | 0 |
| Setaria faberii | 100 | 100 | 100 | 100 | 100 | 100 | 100 |
| Lamium amplexicaule | 76 | 80 | 98 | 100 | 100 | 100 | 100 |
| Amaranthus retroflexus | 95 | 98 | 100 | 100 | 100 | 100 | 100 |

III + XVII

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|

-continued

| kg/ha | 0.25 | 0.5 | 0.25 | 0.75 | 0.5 | 1 | 0.75 | 1 | 1.5 | 0.5 | 0.5 | 2 | 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 7 |
| Unwanted plants: | | | | | | | | | | | | | |
| Setaria faberii | 75 | 90 | 85 | 100 | 97 | 100 | 100 | 100 | 100 | 100 | 100 | 100 | 100 |
| Lamium amplexicaule | 45 | 50 | 60 | 50 | 70 | 60 | 64 | 80 | 65 | 85 | 92 | 70 | 95 |
| Amaranthus retroflexus | 60 | 75 | 82 | 75 | 98 | 95 | 98 | 100 | 100 | 100 | 100 | 100 | 100 |

| kg/ha | 0.25 | 0.5 | 2.5 | 1.5 | 1 | 3 | 2 |
|---|---|---|---|---|---|---|---|
| | 2.5 | 2.5 | 0.5 | 1.5 | 3 | 1 | 2 |
| Glycine max | 5 | 5 | 7 | 0 | 10 | 12 | 0 |
| Setaria faberii | 100 | 100 | 100 | 100 | 100 | 100 | 100 |
| Lamium amplexicaule | 70 | 75 | 95 | 100 | 100 | 100 | 100 |
| Amaranthus retroflexus | 100 | 100 | 100 | 100 | 100 | 100 | 100 |

III + XVIII

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |
| Crop plant: | | | | | | | | | | | | | |
| Glycine max | 0 | 0 | 0 | 0 | 0 | 0 | 0 | 0 | 0 | 0 | 0 | 0 | 7 |
| Unwanted plants: | | | | | | | | | | | | | |
| Setaria faberii | 77 | 95 | 87 | 100 | 100 | 100 | 100 | 100 | 100 | 100 | 100 | 100 | 100 |
| Lamium amplexicaule | 46 | 51 | 60 | 49 | 70 | 55 | 62 | 74 | 73 | 82 | 92 | 70 | 96 |
| Amaranthus retroflexus | 53 | 70 | 80 | 70 | 97 | 90 | 95 | 100 | 100 | 100 | 100 | 100 | 100 |

| kg/ha | 0.25 | 0.5 | 2.5 | 1.5 | 1 | 3 | 2 |
|---|---|---|---|---|---|---|---|
| | 2.5 | 2.5 | 0.5 | 1.5 | 3 | 1 | 2 |
| Glycine max | 6 | 6 | 7 | 0 | 12 | 12 | 0 |
| Setaria faberii | 100 | 100 | 100 | 100 | 100 | 100 | 100 |
| Lamium amplexicaule | 65 | 70 | 95 | 93 | 100 | 100 | 100 |
| Amaranthus retroflexus | 100 | 100 | 100 | 100 | 100 | 100 | 100 |

IV + V

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 56 | 75 | 70 | 81 | 85 | 100 | 95 | 100 | 100 | 95 | 98 | 100 | 100 |
| Lamium amplexicaule | 45 | 55 | 62 | 60 | 80 | 70 | 80 | 95 | 85 | 95 | 100 | 98 | 100 |
| Amaranthus retroflexus | 63 | 78 | 85 | 85 | 97 | 95 | 98 | 100 | 100 | 100 | 100 | 100 | 100 |

| kg/ha | 0.25 | 0.5 | 2.5 | 1.5 | 1 | 3 | 2 | 2 | 1 |
|---|---|---|---|---|---|---|---|---|---|
| | 2.5 | 2.5 | 0.5 | 1.5 | 3 | 1 | 2 | 1 | 2 |
| Glycine max | 0 | 0 | 5 | 0 | 7 | 10 | 0 | 0 | 0 |
| Setaria faberii | 100 | 100 | 100 | 100 | 100 | 100 | 100 | 100 | 100 |
| Lamium amplexicaule | 95 | 98 | 100 | 100 | 100 | 100 | 100 | 100 | 100 |
| Amaranthus retroflexus | 100 | 100 | 100 | 100 | 100 | 100 | 100 | 100 | 100 |

IV + VI

| kg/ha | 0.25 | 0.5 | 0.75 | 0.25 | 1 | 0.5 | 0.75 | 1 | 0.5 | 2.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 53 | 70 | 65 | 76 | 85 | 95 | 90 | 100 | 100 | 98 | 100 | 100 | 100 |
| Lamium amplexicaule | 44 | 49 | 65 | 61 | 80 | 68 | 80 | 95 | 85 | 94 | 100 | 100 | 100 |
| Amaranthus retroflexus | 67 | 75 | 80 | 80 | 97 | 95 | 95 | 100 | 100 | 100 | 100 | 100 | 100 |

| kg/ha | 0.25 | 0.5 | 2.5 | 1.5 | 1 | 3 | 2 |
|---|---|---|---|---|---|---|---|
| | 2.5 | 2.5 | 0.5 | 1.5 | 3 | 1 | 2 |
| Glycine max | 3 | 3 | 5 | 0 | 10 | 10 | 0 |
| Setaria faberii | 100 | 100 | 100 | 100 | 100 | 100 | 100 |
| Lamium amplexicaule | 100 | 100 | 100 | 100 | 100 | 100 | 100 |
| Amaranthus retroflexus | 100 | 100 | 100 | 100 | 100 | 100 | 100 |

IV + VII

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 55 | 65 | 63 | 68 | 75 | 84 | 80 | 95 | 100 | 85 | 90 | 100 | 90 |
| Lamium amplexicaule | 45 | 50 | 65 | 47 | 72 | 60 | 68 | 75 | 69 | 85 | 96 | 75 | 100 |
| Amaranthus retroflexus | 60 | 65 | 75 | 63 | 85 | 77 | 78 | 90 | 88 | 100 | 100 | 100 | 100 |

| kg/ha | 0.25 | 0.5 | 2.5 | 1.5 | 1 | 3 | 2 |
|---|---|---|---|---|---|---|---|
| | 2.5 | 2.5 | 0.5 | 1.5 | 3 | 1 | 2 |
| Glycine max | 0 | 0 | 5 | 0 | 5 | 10 | 0 |
| Setaria faberii | 100 | 100 | 95 | 100 | 100 | 100 | 100 |
| Lamium amplexicaule | 70 | 75 | 100 | 100 | 100 | 100 | 100 |

-continued

| Amaranthus retroflexus | 100 | 100 | 100 | 100 | 100 | 100 | 100 | | | | | | |

IV + VIII

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 58 | 70 | 70 | 80 | 83 | 85 | 84 | 90 | 100 | 87 | 95 | 100 | 90 |
| Lamium amplexicaule | 45 | 50 | 67 | 65 | 70 | 68 | 70 | 80 | 70 | 85 | 95 | 80 | 100 |
| Amaranthus retroflexus | 58 | 64 | 72 | 75 | 85 | 78 | 77 | 95 | 88 | 100 | 100 | 98 | 100 |

| kg/ha | 0.25 | 0.5 | 2.5 | 1.5 | 1 | 3 | 2 |
|---|---|---|---|---|---|---|---|
| | 2.5 | 2.5 | 0.5 | 1.5 | 3 | 1 | 2 |
| Glycine max | 0 | 0 | 5 | 0 | 4 | 10 | 0 |
| Setaria faberii | 100 | 100 | 100 | 100 | 100 | 100 | 100 |
| Lamium amplexicaule | 78 | 83 | 100 | 100 | 100 | 100 | 100 |
| Amaranthus retroflexus | 96 | 100 | 100 | 100 | 100 | 100 | 100 |

IV + IX

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 60 | 75 | 70 | 76 | 83 | 95 | 90 | 100 | 100 | 96 | 98 | 100 | 90 |
| Lamium amplexicaule | 45 | 50 | 65 | 50 | 70 | 60 | 68 | 75 | 72 | 85 | 95 | 80 | 100 |
| Amaranthus retroflexus | 60 | 65 | 72 | 60 | 85 | 74 | 75 | 90 | 87 | 100 | 100 | 100 | 100 |

| kg/ha | 0.25 | 0.5 | 2.5 | 1.5 | 1 | 3 | 2 | 2 | 1 |
|---|---|---|---|---|---|---|---|---|---|
| | 2.5 | 2.5 | 0.5 | 1.5 | 3 | 1 | 2 | 1 | 2 |
| Glycine max | 0 | 0 | 5 | 0 | 6 | 10 | 0 | 0 | 0 |
| Setaria faberii | 100 | 100 | 100 | 100 | 100 | 100 | 100 | 100 | 100 |
| Lamium amplexicaule | 80 | 83 | 100 | 97 | 100 | 100 | 100 | 100 | 100 |
| Amaranthus retroflexus | 100 | 100 | 100 | 100 | 100 | 100 | 100 | 100 | 100 |

IV + X

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 62 | 80 | 75 | 85 | 90 | 100 | 94 | 100 | 100 | 96 | 98 | 100 | 100 |
| Lamium amplexicaule | 45 | 55 | 65 | 60 | 83 | 70 | 80 | 92 | 90 | 95 | 100 | 100 | 100 |
| Amaranthus retroflexus | 70 | 80 | 86 | 90 | 100 | 100 | 100 | 100 | 100 | 100 | 100 | 100 | 100 |

| kg/ha | 0.25 | 0.5 | 2.5 | 1.5 | 1 | 3 | 2 |
|---|---|---|---|---|---|---|---|
| | 2.5 | 2.5 | 0.5 | 1.5 | 3 | 1 | 2 |
| Glycine max | 5 | 5 | 5 | 0 | 10 | 10 | 0 |
| Setaria faberii | 100 | 100 | 100 | 100 | 100 | 100 | 100 |
| Lamium amplexicaule | 100 | 100 | 100 | 100 | 100 | 100 | 100 |
| Amaranthus retroflexus | 100 | 100 | 100 | 100 | 100 | 100 | 100 |

IV + XI

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 58 | 70 | 73 | 80 | 85 | 98 | 95 | 100 | 100 | 98 | 98 | 100 | 92 |
| Lamium amplexicaule | 45 | 56 | 63 | 60 | 80 | 65 | 80 | 90 | 86 | 93 | 100 | 85 | 100 |
| Amaranthus retroflexus | 68 | 80 | 82 | 80 | 98 | 95 | 95 | 100 | 100 | 100 | 100 | 100 | 100 |

| kg/ha | 0.25 | 0.5 | 2.5 | 1.5 | 1 | 3 | 2 |
|---|---|---|---|---|---|---|---|
| | 2.5 | 2.5 | 0.5 | 1.5 | 3 | 1 | 2 |
| Glycine max | 0 | 0 | 5 | 0 | 6 | 10 | 0 |
| Setaria faberii | 100 | 100 | 100 | 100 | 100 | 100 | 100 |
| Lamium amplexicaule | 86 | 100 | 100 | 100 | 100 | 100 | 100 |
| Amaranthus retroflexus | 100 | 100 | 100 | 100 | 100 | 100 | 100 |

IV + XII

| kg/ha | 0.25 | 0.5 | 0.75 | 0.25 | 1 | 0.5 | 0.75 | 1 | 0.5 | 1.5 | 2 | 0.5 | 2.5 |
|---|---|---|---|---|---|---|---|---|---|---|---|---|---|
| | 0.25 | 0.5 | 0.25 | 0.75 | 0.5 | 1 | 0.75 | 1 | 1.5 | 0.5 | 0.5 | 2 | 0.25 |
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 70 | 85 | 85 | 95 | 96 | 100 | 100 | 100 | 100 | 100 | 100 | 100 | 100 |
| Lamium amplexicaule | 47 | 57 | 65 | 60 | 80 | 70 | 81 | 93 | 80 | 95 | 100 | 85 | 100 |
| Amaranthus retroflexus | 62 | 75 | 75 | 79 | 95 | 90 | 95 | 100 | 100 | 100 | 100 | 100 | 100 |

| kg/ha | 0.25 | 0.5 | 2.5 | 1.5 | 1 | 3 | 2 |
|---|---|---|---|---|---|---|---|

-continued

| kg/ha | 2.5 | 2.5 | 0.5 | 1.5 | 3 | 1 | 2 | | | | | | |
|---|---|---|---|---|---|---|---|---|---|---|---|---|---|
| Glycine max | 0 | 0 | 5 | 0 | 5 | 10 | 0 | | | | | | |
| Setaria faberii | 100 | 100 | 100 | 100 | 100 | 100 | 100 | | | | | | |
| Lamium amplexicaule | 86 | 90 | 100 | 100 | 100 | 100 | 100 | | | | | | |
| Amaranthus retroflexus | 100 | 100 | 100 | 100 | 100 | 100 | 100 | | | | | | |

IV + XIII

| kg/ha | 0.25 / 0.25 | 0.5 / 0.5 | 0.75 / 0.25 | 0.25 / 0.75 | 1 / 0.5 | 0.5 / 1 | 0.75 / 0.75 | 1 / 1 | 0.5 / 1.5 | 1.5 / 0.5 | 2 / 0.5 | 0.5 / 2 | 2.5 / 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 56 | 74 | 70 | 85 | 89 | 100 | 100 | 100 | 100 | 100 | 100 | 100 | 100 |
| Lamium amplexicaule | 46 | 50 | 65 | 65 | 75 | 70 | 75 | 90 | 77 | 88 | 96 | 85 | 100 |
| Amaranthus retroflexus | 57 | 70 | 73 | 70 | 90 | 85 | 87 | 100 | 95 | 100 | 100 | 100 | 100 |

| kg/ha | 0.25 / 2.5 | 0.5 / 2.5 | 2.5 / 0.5 | 1.5 / 1.5 | 1 / 3 | 3 / 1 | 2 / 2 | 2 / 1 | 1 / 2 | | | | |
|---|---|---|---|---|---|---|---|---|---|---|---|---|---|
| Glycine max | 0 | 0 | 5 | 0 | 4 | 10 | 0 | 0 | 0 | | | | |
| Setaria faberii | 100 | 100 | 100 | 100 | 100 | 100 | 100 | 100 | 100 | | | | |
| Lamium amplexicaule | 80 | 85 | 100 | 100 | 100 | 100 | 100 | 100 | 100 | | | | |
| Amaranthus retroflexus | 100 | 100 | 100 | 100 | 100 | 100 | 100 | 100 | 100 | | | | |

IV + XIV

| kg/ha | 0.25 / 0.25 | 0.5 / 0.5 | 0.75 / 0.25 | 0.25 / 0.75 | 1 / 0.5 | 0.5 / 1 | 0.75 / 0.75 | 1 / 1 | 0.5 / 1.5 | 1.5 / 0.5 | 2 / 0.5 | 0.5 / 2 | 2.5 / 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 57 | 73 | 70 | 70 | 81 | 90 | 90 | 98 | 100 | 93 | 100 | 100 | 95 |
| Lamium amplexicaule | 45 | 50 | 60 | 65 | 75 | 67 | 68 | 85 | 77 | 85 | 95 | 85 | 100 |
| Amaranthus retroflexus | 65 | 78 | 80 | 80 | 97 | 90 | 93 | 100 | 100 | 100 | 100 | 100 | 100 |

| kg/ha | 0.25 / 2.5 | 0.5 / 2.5 | 2.5 / 0.5 | 1.5 / 1.5 | 1 / 3 | 3 / 1 | 2 / 2 | | | | | | |
|---|---|---|---|---|---|---|---|---|---|---|---|---|---|
| Glycine max | 3 | 3 | 5 | 0 | 10 | 10 | 0 | | | | | | |
| Setaria faberii | 100 | 100 | 100 | 100 | 100 | 100 | 100 | | | | | | |
| Lamium amplexicaule | 85 | 90 | 100 | 100 | 100 | 100 | 100 | | | | | | |
| Amaranthus retroflexus | 100 | 100 | 100 | 100 | 100 | 100 | 100 | | | | | | |

IV + XV

| kg/ha | 0.25 / 0.25 | 0.5 / 0.5 | 0.75 / 0.25 | 0.25 / 0.75 | 1 / 0.5 | 0.5 / 1 | 0.75 / 0.75 | 1 / 1 | 0.5 / 1.5 | 1.5 / 0.5 | 2 / 0.5 | 0.5 / 2 | 2.5 / 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 53 | 65 | 65 | 71 | 75 | 95 | 85 | 100 | 100 | 90 | 90 | 100 | 98 |
| Lamium amplexicaule | 45 | 50 | 63 | 49 | 75 | 65 | 65 | 79 | 60 | 86 | 96 | 70 | 100 |
| Amaranthus retroflexus | 58 | 65 | 70 | 60 | 86 | 67 | 75 | 89 | 88 | 100 | 100 | 100 | 100 |

| kg/ha | 0.25 / 2.5 | 0.5 / 2.5 | 2.5 / 0.5 | 1.5 / 1.5 | 1 / 3 | 3 / 1 | 2 / 2 | 2 / 1 | 1 / 2 | | | | |
|---|---|---|---|---|---|---|---|---|---|---|---|---|---|
| Glycine max | 0 | 0 | 5 | 0 | 4 | 10 | 0 | 0 | 0 | | | | |
| Setaria faberii | 100 | 100 | 100 | 100 | 100 | 100 | 100 | 100 | 100 | | | | |
| Lamium amplexicaule | 70 | 75 | 100 | 95 | 100 | 100 | 100 | 100 | 85 | | | | |
| Amaranthus retroflexus | 95 | 100 | 100 | 100 | 100 | 100 | 100 | 100 | 100 | | | | |

IV + XVI

| kg/ha | 0.25 / 0.25 | 0.5 / 0.5 | 0.75 / 0.25 | 0.25 / 0.75 | 1 / 0.5 | 0.5 / 1 | 0.75 / 0.75 | 1 / 1 | 0.5 / 1.5 | 1.5 / 0.5 | 2 / 0.5 | 0.5 / 2 | 2.5 / 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 58 | 70 | 70 | 75 | 82 | 95 | 90 | 100 | 100 | 94 | 97 | 100 | 96 |
| Lamium amplexicaule | 46 | 51 | 63 | 49 | 72 | 60 | 69 | 78 | 65 | 87 | 97 | 70 | 100 |
| Amaranthus retroflexus | 58 | 63 | 73 | 60 | 85 | 75 | 78 | 98 | 87 | 100 | 100 | 98 | 100 |

| kg/ha | 0.25 / 2.5 | 0.5 / 2.5 | 2.5 / 0.5 | 1.5 / 1.5 | 1 / 3 | 3 / 1 | 2 / 2 | | | | | | |
|---|---|---|---|---|---|---|---|---|---|---|---|---|---|
| Glycine max | 0 | 0 | 5 | 0 | 5 | 10 | 0 | | | | | | |
| Setaria faberii | 100 | 100 | 100 | 100 | 100 | 100 | 100 | | | | | | |
| Lamium amplexicaule | 75 | 80 | 100 | 100 | 100 | 100 | 100 | | | | | | |
| Amaranthus retroflexus | 97 | 100 | 100 | 100 | 100 | 100 | 100 | | | | | | |

IV + XVII

| kg/ha | 0.25 / 0.25 | 0.5 / 0.5 | 0.75 / 0.25 | 0.25 / 0.75 | 1 / 0.5 | 0.5 / 1 | 0.75 / 0.75 | 1 / 1 | 0.5 / 1.5 | 1.5 / 0.5 | 2 / 0.5 | 0.5 / 2 | 2.5 / 0.25 |
|---|---|---|---|---|---|---|---|---|---|---|---|---|---|
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |

-continued

| | | | | | | | | | | | | | |
|---|---|---|---|---|---|---|---|---|---|---|---|---|---|
| Setaria faberii | 74 | 90 | 90 | 100 | 100 | 100 | 100 | 100 | 100 | 100 | 100 | 100 | 100 |
| Lamium amplexicaule | 47 | 50 | 65 | 50 | 70 | 65 | 68 | 85 | 60 | 83 | 96 | 70 | 100 |
| Amaranthus retroflexus | 65 | 71 | 78 | 80 | 96 | 95 | 95 | 100 | 100 | 100 | 100 | 100 | 100 |

| | | | | | | | |
|---|---|---|---|---|---|---|---|
| kg/ha | 0.25<br>2.5 | 0.5<br>2.5 | 2.5<br>0.5 | 1.5<br>1.5 | 1<br>3 | 3<br>1 | 2<br>2 |
| Glycine max | 5 | 5 | 5 | 0 | 10 | 10 | 0 |
| Setaria faberii | 100 | 100 | 100 | 100 | 100 | 100 | 100 |
| Lamium amplexicaule | 71 | 75 | 100 | 100 | 100 | 100 | 100 |
| Amaranthus retroflexus | 100 | 100 | 100 | 100 | 100 | 100 | 100 |

IV + XVIII

| kg/ha | | | | | | | | | | | | | |
|---|---|---|---|---|---|---|---|---|---|---|---|---|---|
| | 0.25<br>0.25 | 0.5<br>0.5 | 0.75<br>0.25 | 0.25<br>0.75 | 1<br>0.5 | 0.5<br>1 | 0.75<br>0.75 | 1<br>1 | 0.5<br>1.5 | 1.5<br>0.5 | 2<br>0.5 | 0.5<br>2 | 2.5<br>0.25 |
| Crop plant: | | | | | | | | | | | | | |
| Glycine max | 0 | 0 | 0 | 0 | 0 | 0 | 0 | 0 | 0 | 0 | 0 | 0 | 5 |
| Unwanted plants: | | | | | | | | | | | | | |
| Setaria faberii | 76 | 90 | 90 | 100 | 100 | 100 | 100 | 100 | 100 | 100 | 100 | 100 | 100 |
| Lamium amplexicaule | 45 | 50 | 65 | 50 | 75 | 60 | 65 | 85 | 65 | 80 | 96 | 69 | 100 |
| Amaranthus retroflexus | 60 | 70 | 75 | 75 | 95 | 90 | 90 | 100 | 100 | 100 | 100 | 100 | 100 |

| kg/ha | 0.25<br>2.5 | 0.5<br>2.5 | 2.5<br>0.5 | 1.5<br>1.5 | 1<br>3 | 3<br>1 | 2<br>2 |
|---|---|---|---|---|---|---|---|
| Glycine max | 6 | 6 | 5 | 0 | 12 | 10 | 0 |
| Setaria faberii | 100 | 100 | 100 | 100 | 100 | 100 | 100 |
| Lamium amplexicaule | 70 | 75 | 100 | 100 | 100 | 100 | 100 |
| Amaranthus retroflexus | 100 | 100 | 100 | 100 | 100 | 100 | 100 |

0 = no damage
100 = complete destruction

EXAMPLE 3

In the open, various plants were treated at a growth height of from 2 to 18 cm with the following amounts of the following individual active ingredients and compositions thereof as dispersions, emulsions or aqueous solutions:

I 3-isopropyl-2,1,3-benzothiadiazinone-(4)-2,2-dioxide

II 3-isopropyl-2,1,3-benzothiadiazine-(4)-2,2-dioxide, sodium salt

III 3-isopropyl-2,1,3-benzothiadiazinone-(4)-2,2-dioxide, dimethylammonium salt

IV 3-isopropyl-2,1,3-benzothiadiazinone-(4)-2,2-dioxide, diethanolammonium salt

V 0-(methylaminosulfonyl)-glycolic acid hexamethylene amide

XXXII S-4-chlorobenzyl-2,2,4-trimethylazetidiene-1-carbothiolate

XXXIII S-benzyl-2,2,4-trimethylazetidine-1-carbothiolate each of these compositions at rates of 0.25, 0.5, 0.75, 1, 1.5, 2, 2.5, 2.75, 3 and 4 kg/ha; I+V, II+V, III+V, I+XXXII, II+XXXII, III+XXXII, IV+XXXII, I+XXXIII, II+XXXIII, III+XXXIII and IV+XXXIII each composition at rates of 0.25+0.25+0.5+0.5, 0.75+0.5, 0.25+0.75, 1+0.5 0.5+1, 0.75+0.75, 1+1, 0.5+1.5, 1.5+0.5, 2+0.5, 0.5+2, 2.5+0.25, 0.25+2.5, 0.5+2.5, 2.5+0.5, 1.5+1.5, 1 , 2 , 3+1, 1 and 2+ Kgha.

During experiment the plants were kept fairly dry.

After 3 to 4 weeks it was ascertained that at the lower application rates the compositions has a better herbicidal action than their components, combined with the same crop plant compatibility. At the higher application rates the compatibility with Indian corn was still good.

The results are given below:

| Active ingredient kg/ha | 0.25 | 0.5 | 0.75 | 1 | I<br>1.5 | 2 | 2.5 | 2.75 | 3 | 4 |
|---|---|---|---|---|---|---|---|---|---|---|
| Crop plant: | | | | | | | | | | |
| Zea mays | 0 | 0 | 0 | 0 | 0 | 0 | 0 | 0 | 0 | 0 |
| Unwanted plants: | | | | | | | | | | |
| Setaria faberii | 0 | 5 | 7 | 10 | 10 | 15 | 20 | 23 | 25 | 30 |
| Lamium amplexicaule | 5 | 10 | 20 | 30 | 40 | 60 | 65 | 68 | 70 | 95 |
| | | | | | II | | | | | |
| Zea mays | 0 | 0 | 0 | 0 | 0 | 0 | 0 | 0 | 0 | 0 |
| Setaria faberii | 0 | 6 | 10 | 15 | 20 | 25 | 28 | 32 | 35 | 40 |
| Lamium amplexicaule | 5 | 10 | 15 | 25 | 40 | 54 | 60 | 65 | 75 | 90 |
| | | | | | III | | | | | |
| Zea mays | 0 | 0 | 0 | 0 | 0 | 0 | 0 | 0 | 0 | 0 |
| Setaria faberii | 0 | 4 | 7 | 10 | 15 | 20 | 25 | 27 | 30 | 35 |
| Lamium amplexicaule | 5 | 10 | 20 | 30 | 45 | 50 | 55 | 58 | 60 | 80 |
| | | | | | IV | | | | | |
| Zea mays | 0 | 0 | 0 | 0 | 0 | 0 | 0 | 0 | 0 | 0 |
| Setaria faberii | 0 | 5 | 10 | 15 | 20 | 23 | 25 | 28 | 30 | 35 |
| Lamium amplexicaule | 6 | 10 | 25 | 35 | 48 | 60 | 65 | 70 | 75 | 87 |
| Crop plant: | | | | | | | | | | |
| Zea mays | 0 | 0 | 0 | 0 | 0 | 0 | 0 | 0 | 0 | 10 |
| Unwanted plants: | | | | | | | | | | |
| Setaria faberii | 20 | 30 | 45 | 60 | 80 | 90 | 98 | 100 | 100 | 100 |
| Lamium amplexicaule | 0 | 5 | 15 | 20 | 35 | 45 | 47 | 53 | 55 | 60 |

-continued

| kg/ha | 0.25 0.25 | 0.5 0.5 | 0.75 0.25 | I + V 0.25 0.75 | 1 0.5 | 0.5 1 | 0.75 0.75 | 1 1 | 0.5 1.5 | 1.5 0.5 | 2 0.5 | | |
|---|---|---|---|---|---|---|---|---|---|---|---|---|---|
| Zea mays | 0 | 0 | 0 | 0 | 0 | 0 | 0 | 0 | 0 | 0 | 0 | | |
| Setaria faberii | 58 | 75 | 67 | 85 | 82 | 100 | 93 | 100 | 100 | 87 | 90 | | |
| Lamium amplexicaule | 46 | 55 | 60 | 60 | 70 | 72 | 77 | 87 | 88 | 87 | 95 | | |

| kg/ha | 0.5 2 | 2.5 0.25 | 0.25 2.5 | I + V 0.5 2.5 | 2.5 0.5 | 1.5 1.5 | 1 3 | 3 1 | 2 2 | | | | |
|---|---|---|---|---|---|---|---|---|---|---|---|---|---|
| Zea mays | 0 | 0 | 0 | 0 | 0 | 0 | 0 | 0 | 0 | | | | |
| Setaria faberii | 100 | 100 | 100 | 100 | 100 | 100 | 100 | 100 | 100 | | | | |
| Lamium amplexicaule | 95 | 100 | 96 | 100 | 100 | 100 | 100 | 100 | 100 | | | | |

| kg/ha | 0.25 0.25 | 0.5 0.5 | 0.75 0.25 | II + V 0.25 0.75 | 1 0.5 | 0.5 1 | 0.75 0.75 | 1 1 | 0.5 1.5 | 1.5 0.5 | 2 0.5 | 0.5 2 | |
|---|---|---|---|---|---|---|---|---|---|---|---|---|---|
| Crop plant: Zea mays | 0 | 0 | 0 | 0 | 0 | 0 | 0 | 0 | 0 | 0 | 0 | 0 | |
| Unwanted plants: Setaria faberii | 63 | 76 | 70 | 86 | 88 | 100 | 95 | 100 | 100 | 96 | 97 | 100 | |
| Lamium amplexicaule | 45 | 54 | 63 | 60 | 70 | 70 | 75 | 85 | 85 | 90 | 100 | 95 | |

| kg/ha | 2.5 0.25 | 0.25 2.5 | 0.5 2.5 | II + V 2.5 0.5 | 1.5 1.5 | 1 3 | 3 1 | 2 2 | | | | | |
|---|---|---|---|---|---|---|---|---|---|---|---|---|---|
| Zea mays | 0 | 0 | 0 | 0 | 0 | 0 | 0 | 0 | | | | | |
| Setaria faberii | 100 | 100 | 100 | 100 | 100 | 100 | 100 | 100 | | | | | |
| Lamium amplexicaule | 96 | 96 | 98 | 100 | 100 | 100 | 100 | | | | | | |

| kg/ha | 0.25 0.25 | 0.5 0.5 | 0.75 0.25 | III + V 0.25 0.75 | 1 0.5 | 0.5 1 | 0.75 075 | 1 1 | 0.5 1.5 | 1.5 0.5 | 2 0.5 | 0.5 2 | 2.5 0.25 |
|---|---|---|---|---|---|---|---|---|---|---|---|---|---|
| Zea mays | 0 | 0 | 0 | 0 | 0 | 0 | 0 | 0 | 0 | 0 | 0 | 0 | 0 |
| Setaria faberii | 56 | 75 | 65 | 82 | 80 | 100 | 90 | 100 | 100 | 90 | 100 | 100 | 100 |
| Lamium amplexicaule | 45 | 60 | 60 | 60 | 75 | 70 | 75 | 90 | 85 | 90 | 98 | 96 | 98 |

| kg/ha | 0.25 2.5 | 0.5 2.5 | III + V 2.5 0.5 | 1.5 1.5 | 1 3 | 3 1 | 2 2 | | | | | | |
|---|---|---|---|---|---|---|---|---|---|---|---|---|---|
| Crop plant: Zea mays | 0 | 0 | 0 | 0 | 0 | 0 | 0 | | | | | | |
| Unwanted plants: Setaria faberii | 100 | 100 | 100 | 100 | 100 | 100 | 100 | | | | | | |
| Lamium amplexicaule | 98 | 100 | 100 | 100 | 100 | 100 | 100 | | | | | | |

| kg/ha | 0.25 0.25 | 0.5 0.5 | 0.75 0.25 | IV + V 0.25 0.75 | 1 0.5 | 0.5 1 | 0.75 0.75 | 1 1 | 0.5 1.5 | 1.5 0.5 | 2 0.5 | 0.5 2 | 2.5 0.25 | 0.25 2.5 |
|---|---|---|---|---|---|---|---|---|---|---|---|---|---|---|
| Zea mays | 0 | 0 | 0 | 0 | 0 | 0 | 0 | 0 | 0 | 0 | 0 | 0 | 0 | 0 |
| Setaria faberii | 56 | 75 | 70 | 81 | 85 | 100 | 95 | 100 | 100 | 95 | 100 | 100 | 100 | 100 |
| Lamium amplexicaule | 45 | 55 | 62 | 60 | 80 | 70 | 80 | 95 | 86 | 95 | 100 | 98 | 100 | 95 |

| kg/ha | 0.5 2.5 | 2.5 0.5 | IV + V 1.5 1.5 | 1 3 | 3 1 | 2 2 | | | | | | | |
|---|---|---|---|---|---|---|---|---|---|---|---|---|---|
| Zea mays | 0 | 0 | 0 | 0 | 0 | 0 | | | | | | | |
| Setaria faberii | 100 | 100 | 100 | 100 | 100 | 100 | | | | | | | |
| Lamium amplexicaule | 98 | 100 | 100 | 100 | 100 | 100 | | | | | | | |

| kg/ha | I + V 2 1 | I + V 1 2 | II + V 2 1 | II + V 1 2 | III + V 2 1 | III + V 1 2 | IV + V 2 1 | IV + V 1 2 | | | | | |
|---|---|---|---|---|---|---|---|---|---|---|---|---|---|
| Crop plant: Zea mays | 0 | 0 | 0 | 0 | 0 | 0 | 0 | 0 | | | | | |
| Unwanted plants: Setaria faberii | 100 | 100 | 100 | 100 | 100 | 100 | 100 | 100 | | | | | |
| Lamium amplexicaule | 100 | 100 | 100 | 100 | 100 | 100 | 100 | 100 | | | | | |

| kg/ha | 0.25 | 0.5 | 0.75 | XXXII 1 | 1.5 | 2 | 2.5 | | | | | | |
|---|---|---|---|---|---|---|---|---|---|---|---|---|---|
| Zea mays | 0 | 0 | 0 | 0 | 0 | 0 | 0 | | | | | | |
| Setaria faberii | 20 | 30 | 40 | 55 | 80 | 90 | 95 | | | | | | |
| Lamium amplexicaule | 0 | 3 | 7 | 15 | 20 | 30 | 45 | | | | | | |

| kg/ha | 2.75 | XXXII 3 | 4 | 0.25 | 0.5 | 0.75 | 1 | XXXIII 1.5 | 2 | 2.5 | 2.75 | 3 | 4 |
|---|---|---|---|---|---|---|---|---|---|---|---|---|---|
| Zea mays | 5 | 10 | 15 | 0 | 0 | 0 | 0 | 0 | 0 | 0 | 0 | 5 | 15 |
| Setaria faberii | 100 | 100 | 100 | 15 | 25 | 40 | 60 | 80 | 85 | 90 | 100 | 100 | 100 |
| Lamium amplexicaule | 50 | 55 | 60 | 3 | 5 | 10 | 15 | 20 | 40 | 47 | 55 | 60 | 70 |

| kg/ha | 0.25 0.25 | 0.5 0.5 | 0.75 0.25 | I + XXXII 0.25 0.75 | 1 0.5 | 0.5 1 | 0.75 0.75 | 1 1 | | | | | |
|---|---|---|---|---|---|---|---|---|---|---|---|---|---|
| Crop plant: Zea mays | 0 | 0 | 0 | 0 | 0 | 0 | 0 | 0 | | | | | |
| Unwanted plants: Setaria faberii | 60 | 75 | 67 | 80 | 85 | 97 | 87 | 100 | | | | | |
| Lamium amplexicaule | 47 | 54 | 60 | 52 | 63 | 65 | 67 | 85 | | | | | |

| kg/ha | 0.5 1.5 | 1.5 0.5 | I + XXXII 2 0.5 | 0.5 2 | 2.5 0.25 | 0.25 2.5 | 0.5 2.5 | 2.5 0.5 | 1.5 1.5 | 2 1 | 1 2 | 1 3 | 3 1 | 2 2 |
|---|---|---|---|---|---|---|---|---|---|---|---|---|---|---|
| Zea mays | 0 | 0 | 0 | 0 | 0 | 0 | 0 | 0 | 0 | 0 | 0 | 10 | 0 | 0 |

-continued

| | | | | | | | | | | | | | | | |
|---|---|---|---|---|---|---|---|---|---|---|---|---|---|---|---|
| Setaria faberii | 100 | 92 | 98 | 100 | 100 | 100 | 100 | 100 | 100 | 100 | 100 | 100 | 100 | 100 | |
| Lamium amplexicaule | 70 | 83 | 100 | 80 | 100 | 90 | 100 | 100 | 100 | 100 | 100 | 100 | 100 | 100 | |
| | | | II + | XXXII | | | | | | | | | | | |
| kg/ha | 0.25 | 0.5 | 0.75 | 0.25 | 1 | 0.5 | 0.75 | | | | | | | | |
| | 0.25 | 0.5 | 0.25 | 0.75 | 0.5 | 1 | 0.75 | | | | | | | | |

| | | | | | | | |
|---|---|---|---|---|---|---|---|
| Zea mays | 0 | 0 | 0 | 0 | 0 | 0 | 0 |
| Setaria faberii | 60 | 76 | 70 | 80 | 85 | 98 | 90 |
| Lamium amplexicaule | 46 | 53 | 55 | 52 | 68 | 65 | 62 |

| | | | | | | | | | | | | | | |
|---|---|---|---|---|---|---|---|---|---|---|---|---|---|---|
| | | | | | | | II + | XXXII | | | | | | |
| kg/ha | 1 | 0.5 | 1.5 | 2 | 0.5 | 2.5 | 0.25 | 0.5 | 2.5 | 1.5 | 2 | 1 | 1 | 3 | 2 |
| | 1 | 1.5 | 0.5 | 0.5 | 2 | 0.25 | 2.5 | 2.5 | 0.5 | 1.5 | 1 | 2 | 3 | 1 | 2 |

| | | | | | | | | | | | | | | | |
|---|---|---|---|---|---|---|---|---|---|---|---|---|---|---|---|
| Crop plant: | | | | | | | | | | | | | | | |
| Zea mays | 0 | 0 | 0 | 0 | 0 | 0 | 0 | 0 | 0 | 0 | 0 | 0 | 10 | 0 | 0 |
| Unwanted plants: | | | | | | | | | | | | | | | |
| Setaria faberii | 100 | 100 | 95 | 98 | 100 | 100 | 100 | 100 | 100 | 100 | 100 | 100 | 100 | 100 | 100 |
| Lamium amplexicaule | 80 | 70 | 83 | 97 | 80 | 100 | 90 | 95 | 100 | 100 | 100 | 100 | 100 | 100 | 100 |
| | | | III + | XXXII | | | | | | | | | | | |
| kg/ha | 0.25 | 0.5 | 0.75 | 0.25 | 1 | 0.5 | | | | | | | | | |
| | 0.25 | 0.5 | 0.25 | 0.75 | 0.5 | 1 | | | | | | | | | |

| | | | | | | |
|---|---|---|---|---|---|---|
| Zea mays | 0 | 0 | 0 | 0 | 0 | 0 |
| Setaria faberii | 61 | 74 | 67 | 80 | 85 | 98 |
| Lamium amplexicaule | 45 | 53 | 60 | 52 | 73 | 65 |

| | | | | | | | | | | | | | | | |
|---|---|---|---|---|---|---|---|---|---|---|---|---|---|---|---|
| | | | | | | | III + | XXXII | | | | | | | |
| kg/ha | 0.75 | 1 | 0.5 | 1.5 | 2 | 0.5 | 2.5 | 0.25 | 0.5 | 2.5 | 1.5 | 1 | 2 | 1 | 3 | 2 |
| | 0.75 | 1 | 1.5 | 0.5 | 0.5 | 2 | 0.25 | 2.5 | 2.5 | 0.5 | 1.5 | 2 | 1 | 3 | 1 | 2 |

| | | | | | | | | | | | | | | | |
|---|---|---|---|---|---|---|---|---|---|---|---|---|---|---|---|
| Zea mays | 0 | 0 | 0 | 0 | 0 | 0 | 0 | 0 | 0 | 0 | 0 | 0 | 10 | 0 | 0 |
| Setaria faberii | 87 | 100 | 100 | 93 | 98 | 100 | 100 | 100 | 100 | 100 | 100 | 100 | 100 | 100 | 100 |
| Lamium amplexicaule | 68 | 85 | 70 | 88 | 95 | 90 | 95 | 100 | 100 | 100 | 100 | 100 | 100 | 100 | 100 |
| | | | IV + | XXXII | | | | | | | | | | | |
| kg/ha | 0.25 | 0.5 | 0.75 | 0.25 | 1 | | | | | | | | | | |
| | 0.25 | 0.5 | 0.25 | 0.75 | 0.5 | | | | | | | | | | |

| | | | | | | |
|---|---|---|---|---|---|---|
| Crop plant: | | | | | | |
| Zea mays | 0 | 0 | 0 | 0 | 0 | |
| Unwanted plants: | | | | | | |
| Setaria faberii | 59 | 75 | 70 | 80 | 85 | |
| Lamium amplexicaule | 47 | 53 | 65 | 53 | 78 | |
| | | | IV+ | XXXII | | |

| | | | | | | | | | | | |
|---|---|---|---|---|---|---|---|---|---|---|---|
| kg/ha | 0.5 | 0.75 | 1 | 0.5 | 1.5 | 2 | 0.5 | 2.5 | 0.25 | 0.5 | 2.5 | 1.5 |
| | 1 | 0.75 | 1 | 1.5 | 0.5 | 0.5 | 2 | 0.25 | 2.5 | 2.5 | 0.5 | 1.5 |

| | | | | | | | | | | | | |
|---|---|---|---|---|---|---|---|---|---|---|---|---|
| Zea mays | 0 | 0 | 0 | 0 | 0 | 0 | 0 | 0 | 0 | 0 | 0 | |
| Setaria faberii | 100 | 90 | 100 | 100 | 95 | 98 | 100 | 100 | 100 | 100 | 100 | |
| Lamium amplexicaule | 65 | 73 | 90 | 70 | 90 | 100 | 80 | 100 | 92 | 95 | 95 | 100 |
| | | | IV + | XXXII | | | I + | XXXIII | | | | |
| kg/ha | 2 | 1 | 1 | 3 | 2 | 0.25 | 0.5 | 0.75 | 0.25 | | | |
| | 1 | 2 | 3 | 1 | 2 | 0.25 | 0.5 | 0.25 | 0.75 | | | |

| | | | | | | | | | | |
|---|---|---|---|---|---|---|---|---|---|---|
| Zea mays | 0 | 0 | 10 | 0 | 0 | 0 | 0 | 0 | 0 | |
| Setaria faberii | 100 | 100 | 100 | 100 | 100 | 55 | 70 | 65 | 80 | |
| Lamium amplexicaule | 100 | 100 | 100 | 100 | 100 | 50 | 55 | 63 | 58 | |
| | | | | | | I + | XXXIII | | | |
| kg/ha | 1 | 0.5 | 0.75 | 1 | 0.5 | 1.5 | 2 | 0.5 | 2.5 | 0.25 | 0.5 | 2.5 | 1.5 |
| | 0.5 | 1 | 0.75 | 1 | 1.5 | 0.5 | 0.5 | 2 | 0.25 | 2.5 | 2.5 | 0.5 | 1.5 |

| | | | | | | | | | | | | |
|---|---|---|---|---|---|---|---|---|---|---|---|---|
| Crop plant: | | | | | | | | | | | | |
| Zea mays | 0 | 0 | 0 | 0 | 0 | 0 | 0 | 0 | 0 | 0 | 0 | 0 |
| Unwanted plants: | | | | | | | | | | | | |
| Setaria faberii | 83 | 100 | 87 | 100 | 100 | 90 | 94 | 100 | 100 | 100 | 100 | 100 | 100 |
| Lamium amplexicaule | 75 | 65 | 70 | 85 | 70 | 85 | 100 | 90 | 100 | 89 | 97 | 100 | 100 |
| | | | I + | XXXIII | | | II + | XXXIII | | | | |
| kg/ha | 2 | 1 | 1 | 3 | 2 | 0.25 | 0.5 | 0.75 | | | | |
| | 1 | 2 | 3 | 1 | 2 | 0.25 | 0.5 | 0.25 | | | | |

| | | | | | | | | |
|---|---|---|---|---|---|---|---|---|
| Zea mays | 0 | 0 | 5 | 0 | 0 | | 0 | 0 | 0 |
| Setaria faberii | 100 | 100 | 100 | 100 | 100 | | 55 | 71 | 65 |
| Lamium amplexicaule | 100 | 100 | 100 | 100 | 100 | | 49 | 55 | 58 |
| | | | | | | II + | XXXIII | | |
| kg/ha | 0.25 | 1 | 0.5 | 0.75 | 1 | 0.5 | 1.5 | 2 | 0.5 | 2.5 | 0.25 | 0.5 | 2.5 | 1.5 |
| | 0.75 | 0.5 | 1 | 0.75 | 1 | 1.5 | 0.5 | 0.5 | 2 | 0.25 | 2.5 | 2.5 | 0.5 | 1.5 |

| | | | | | | | | | | | | | |
|---|---|---|---|---|---|---|---|---|---|---|---|---|---|
| Crop plant: | | | | | | | | | | | | | |
| Zea mays | 0 | 0 | 0 | 0 | 0 | 0 | 0 | 0 | 0 | 0 | 0 | 0 | 0 |
| Unwanted plants: | | | | | | | | | | | | | |
| Setaria faberii | 65 | 85 | 100 | 90 | 100 | 100 | 90 | 95 | 100 | 100 | 100 | 100 | 100 | 100 |
| Lamium amplexicaule | 58 | 70 | 65 | 67 | 80 | 70 | 85 | 98 | 90 | 100 | 92 | 98 | 100 | 100 |
| | | | II + | XXXIII | | | | | | | | | |
| kg/ha | 1 | 2 | 1 | 3 | 2 | | | | | | | | |
| | 2 | 1 | 3 | 1 | 2 | | | | | | | | |

| | | | | | | |
|---|---|---|---|---|---|---|
| Zea mays | 0 | 0 | 5 | 0 | 0 | |
| Setaria faberii | 100 | 100 | 100 | 100 | 100 | |
| Lamium amplexicaule | 100 | 100 | 100 | 100 | 100 | |
| | | | III + | XXXIII | | |
| kg/ha | 0.25 | 0.5 | 0.75 | 0.25 | 1 | 0.5 | 0.75 | 1 | 0.5 | 1.5 | 2 | 0.5 |
| | 0.25 | 0.5 | 0.25 | 0.75 | 0.5 | 1 | 0.75 | 1 | 1.5 | 0.5 | 0.5 | 2 |

| | | | | | | | | | | | | |
|---|---|---|---|---|---|---|---|---|---|---|---|---|
| Crop plant: | | | | | | | | | | | | |
| Zea mays | 0 | 0 | 0 | 0 | 0 | 0 | 0 | 0 | 0 | 0 | 0 | |
| Unwanted plants: | | | | | | | | | | | | |
| Setaria faberii | 57 | 69 | 62 | 80 | 85 | 100 | 87 | 100 | 100 | 90 | 94 | 100 |

-continued

| | | | | | | | | | | | | |
|---|---|---|---|---|---|---|---|---|---|---|---|---|
| Lamium amplexicaule | 48 | 55 | 63 | 55 | 75 | 65 | 70 | 85 | 70 | 90 | 95 | 90 |
| | | | III + | XXXIII | | | | | | | | |
| | 2.5 | 0.25 | 0.5 | 2.5 | 1.5 | 1 | 2 | 1 | 3 | 2 | | |
| kg/ha | 0.25 | 2.5 | 2.5 | 0.5 | 1.5 | 2 | 1 | 3 | 1 | 2 | | |
| Zea mays | 0 | 0 | 0 | 0 | 0 | 0 | 0 | 5 | 0 | 0 | | |
| Setaria faberii | 100 | 100 | 100 | 100 | 100 | 100 | 100 | 100 | 100 | 100 | | |
| Lamium amplexicaule | 98 | 92 | 97 | 100 | 100 | 100 | 100 | 100 | 100 | 100 | | |
| | | | | | | | IV + | XXXIII | | | | |
| | 0.25 | 0.5 | 0.75 | 0.25 | 1 | 0.5 | 0.75 | 1 | 0.5 | 1.5 | 2 | 0.5 |
| kg/ha | 0.25 | 0.5 | 0.25 | 0.75 | 0.5 | 1 | 0.75 | 1 | 1.5 | 0.5 | 0.5 | 2 |
| Crop plant: | | | | | | | | | | | | |
| Zea mays | 0 | 0 | 0 | 0 | 0 | 0 | 0 | 0 | 0 | 0 | 0 | 0 |
| Unwanted plants: | | | | | | | | | | | | |
| Setaria faberii | 55 | 70 | 65 | 80 | 85 | 100 | 90 | 100 | 100 | 90 | 95 | 100 |
| Lamium amlexicaule | 49 | 55 | 68 | 57 | 80 | 68 | 75 | 90 | 70 | 93 | 100 | 90 |
| | | | | | | | V + | XXXIII | | | | |
| | 2.5 | 0.25 | 0.5 | 2.5 | 1.5 | 1 | 2 | 1 | 3 | 2 | | |
| kg/ha | 0.25 | 2.5 | 2.5 | 0.5 | 1.5 | 2 | 1 | 3 | 1 | 2 | | |
| Zea mays | 0 | 0 | 0 | 0 | 0 | 0 | 0 | 5 | 0 | 0 | | |
| Setaria faberii | 100 | 100 | 100 | 100 | 100 | 100 | 100 | 100 | 100 | 100 | | |
| Lamium amplexicaule | 100 | 93 | 97 | 100 | 100 | 100 | 100 | 100 | 100 | 100 | | |

0 = no damage
100 = complete destruction

EXAMPLE 4

In the greenhouse, various plants were treated at a growth height of from 3 to 25 cm with the following amounts of the following individual active ingredients and compositions thereof as dispersions, emulsions, suspensions or aqueous solutions:

I  3-isopropyl-2,1,3-benzothiadiazinone-(4)-2,2,-dioxide
II  3-isopropyl-2,1,3-benzothiadiazinone-(4)-2,2-dioxide, sodium salt
III  3-isopropyl-2,1,3-benzothiadiazinone-(4)-2,2-dioxide, dimethylammonium salt
IV  3-isopropyl-2,1,3-benzothiadiazinone-(4)-2,2-dioxide, diethanolammonium salt
V  O-(methylaminosulfonyl)-glycolic acid hexamethylene amide
VI  O-(ethylaminosulfonyl)-glycolic acid hexamethylene amide
VIII  3-(methylaminosulfonyloxyacetyl)-3-azabicyclo-[3,2,2]-nonane
VIII  O-(methylaminosulfonyl)-glycolic acid heptamethylene amide
IX  3-(isopropylaminosulfonyloxyacetyl)-3-azabicyclo-[3,2,2]-nonane
XXIV  S-ethyl-2,3-dimethylhexahydro-1H-azepine-1-carbothiolate
XXV  S-benzyl-2,3-dimethylhexahydro-1H-azepine-1-carbothiolate
XXVI  S-4-chlorobenzyl-2,3-dimethylhexahydro-1H-azepine-1-carbothiolate each of these compounds at rates of 0.25, 0.5, 0.75, 1, 1.25, 1.5, 2, 3 and 4 kg/ha;

XXXII  S-(4-chlorobenzyl)-2,2,4-trimethylazetidine-1-carbothiolate
at rates of 0.5, 0.75, 1, 1,5 and 2 kg/ha;

XXXI  N-4-chlorophenyl-N', N'-dimethylurea (comparative agent) at rates of 3 and 4 kg/ha; I+V, I+VI, I+VII, I+VIII, I+IX, II+V, II+VI, II+VII, II+VIII, II+IX, III+V, III+VI, III+VII, III+VIII, III+IX, IV+V, IV+VI, IV+VII, IV+VIII, IV+IX, I+XXIV, I+XXV, I+XXVI, II+XXIV, II+XXV, II+XXVI, III+XXIV, III+XXV, III+XXVI, IV+XXIV, IV+XXV, and IV+XXVI each composition at rates of 0.25+0.25, 0.5+0.5, 0.75+0.25, 0.25+0.75, 1+0.25, 0.25+1, 1+0.5, 0.5+1, 0.75+0.75, 2+1, 1+2, 1+1, 0.5+1.5, 1.5+0.5, 1.5+1.5, 1+3, 3+1 and 2+2 kg/ha; I+XXXII, II+XXXII each at rates of 1+05, 0.5+1, 0.75+0.75, 1.5+0.5 and 0.5+1.5 kg/ha;

XXXI+I at a rate of 3+1 kg/ha.

After 2 to 3 weeks it was ascertained that the compositions of I, II, III and IV with V, VI, VII, VIII, IX, XXIV, XXV and XXVI had, at the lower application rates, a better herbicidal action than the compounds when used individually, combined with the same crop plant compatibility. Compositions of I to IV with V to IX and XXIV to XXVI had better compatibility with rice than compound XXXI and the composition of I+XXXI.

The results are given below:

| Active ingredient kg/ha | 0.25 | 0.5 | 0.75 | 1 | I 1.25 | 1.5 | 2 | 3 | 4 |
|---|---|---|---|---|---|---|---|---|---|
| Crop plant: | | | | | | | | | |
| Oryza sativa | 0 | 0 | 0 | 0 | 0 | 0 | 0 | 0 | 5 |
| Unwanted plants: | | | | | | | | | |
| Cyperus esculentus | 20 | 35 | 50 | 65 | 70 | 80 | 90 | 95 | 100 |
| Echinochloa crus-galli | 0 | 5 | 8 | 10 | 15 | 15 | 20 | 25 | 30 |
| Alisma plantago aquatica | 35 | 40 | 50 | 55 | 60 | 70 | 80 | 95 | 100 |
| | | | | | II | | | | |
| Oryza sativa | 0 | 0 | 0 | 0 | 0 | 0 | 0 | 0 | 5 |
| Cyperus esculentus | 10 | 20 | 30 | 50 | 58 | 70 | 80 | 95 | 100 |
| Echinochloa crus-galli | 0 | 5 | 10 | 15 | 17 | 20 | 24 | 30 | 40 |
| Alisma plantago aquatica | 20 | 26 | 34 | 50 | 60 | 72 | 85 | 95 | 100 |
| | | | | | III | | | | |
| Crop plant: | | | | | | | | | |
| Oryza sativa | 0 | 0 | 0 | 0 | 0 | 0 | 0 | 0 | 4 |

-continued

| | | | | | | | | | | | |
|---|---|---|---|---|---|---|---|---|---|---|---|
| Unwanted plants: | | | | | | | | | | | |
| Cyperus esculentus | 15 | 20 | 35 | 50 | 62 | 70 | 80 | 90 | 98 | | |
| Echinochloa crus-galli | 0 | 5 | 9 | 10 | 10 | 13 | 15 | 25 | 40 | | |
| Alisma plantago aquatica | 20 | 30 | 37 | 52 | 64 | 80 | 90 | 98 | 100 | | |
| | | | | | IV | | | | | | |
| Oryza sativa | 0 | 0 | 0 | 0 | 0 | 0 | 0 | 0 | 6 | | |
| Cyperus esculentus | 10 | 25 | 30 | 50 | 60 | 75 | 90 | 95 | 100 | | |
| Echinochloa crus-galli | 5 | 7 | 10 | 14 | 17 | 20 | 24 | 30 | 35 | | |
| Alisma plantago aquatica | 20 | 30 | 40 | 58 | 65 | 80 | 90 | 96 | 100 | | |
| | | | | | V | | | | | | |
| Oryza sativa | 0 | 0 | 0 | 0 | 0 | 0 | 0 | 5 | 10 | | |
| Cyperus esculentus | 10 | 20 | 30 | 40 | 45 | 50 | 65 | 80 | 95 | | |
| Echinochloa crus-galli | 30 | 40 | 50 | 70 | 75 | 80 | 90 | 98 | 100 | | |
| Alisma plantago aquatica | 0 | 5 | 10 | 15 | 20 | 25 | 30 | 35 | 40 | | |
| | | | | | VI | | | | | | |
| Crop plant: | | | | | | | | | | | |
| Oryza sativa | 0 | 0 | 0 | 0 | 0 | 0 | 5 | 10 | 20 | | |
| Unwanted plants: | | | | | | | | | | | |
| Cyperus esculentus | 10 | 20 | 30 | 38 | 45 | 50 | 67 | 80 | 94 | | |
| Echinochloa crus-galli | 30 | 45 | 55 | 75 | 75 | 85 | 95 | 100 | 100 | | |
| Alisma plantago aquatica | 0 | 6 | 10 | 14 | 20 | 26 | 30 | 34 | 44 | | |
| | | | | | VII | | | | | | |
| Oryza sativa | 0 | 0 | 0 | 0 | 0 | 0 | 0 | 5 | 10 | | |
| Cyperus esculentus | 0 | 7 | 10 | 20 | 25 | 30 | 40 | 50 | 65 | | |
| Echinochloa crus-galli | 20 | 30 | 45 | 65 | 70 | 75 | 85 | 95 | 100 | | |
| Alisma plantago aquatica | 0 | 0 | 5 | 8 | 10 | 15 | 20 | 30 | 40 | | |
| | | | | | VIII | | | | | | |
| Oryza sativa | 0 | 0 | 0 | 0 | 0 | 0 | 0 | 3 | 10 | | |
| Cyperus esculentus | 0 | 5 | 10 | 15 | 20 | 30 | 40 | 50 | 60 | | |
| Echinochloa crus-galli | 30 | 35 | 50 | 75 | 80 | 87 | 90 | 98 | 100 | | |
| Alisma plantago aquatica | 0 | 0 | 0 | 5 | 10 | 15 | 20 | 25 | 35 | | |
| | | | | | IX | | | | | | |
| Crop plant: | | | | | | | | | | | |
| Oryza sativa | 0 | 0 | 0 | 0 | 0 | 0 | 0 | 7 | 15 | | |
| Unwanted plants: | | | | | | | | | | | |
| Cyperus esculentus | 0 | 5 | 10 | 15 | 20 | 25 | 30 | 40 | 50 | | |
| Echinochloa crus-galli | 15 | 25 | 40 | 60 | 65 | 70 | 80 | 95 | 100 | | |
| Alisma plantago aquatica | 0 | 0 | 0 | 5 | 7 | 10 | 15 | 25 | 30 | | |
| | | | | | XXIV | | | | | | |
| Oryza sativa | 0 | 0 | 0 | 0 | 0 | 0 | 0 | 5 | 10 | | |
| Cyperus esculentus | 0 | 0 | 0 | 0 | 0 | 5 | 10 | 15 | 20 | | |
| Echinochloa crus-galli | 10 | 17 | 20 | 25 | 30 | 38 | 50 | 70 | 90 | | |
| Alisma plantago aquatica | 5 | 12 | 15 | 18 | 20 | 25 | 32 | 35 | 40 | | |
| | | | | | XXV | | | | | | |
| Crop plant: | | | | | | | | | | | |
| Oryza sativa | 0 | 0 | 0 | 0 | 0 | 0 | 0 | 5 | 10 | | |
| Unwanted plants: | | | | | | | | | | | |
| Cyperus esculentus | 0 | 0 | 0 | 0 | 3 | 7 | 10 | 15 | 25 | | |
| Echinochloa crus-galli | 15 | 20 | 25 | 30 | 37 | 40 | 65 | 85 | 95 | | |
| Alisma plantago aquatica | 5 | 10 | 18 | 25 | 30 | 35 | 39 | 45 | 55 | | |
| | | | | | XXVI | | | | | | |
| Oryza sativa | 0 | 0 | 0 | 0 | 0 | 0 | 0 | 0 | 10 | | |
| Cyperus esculentus | 0 | 0 | 0 | 0 | 0 | 2 | 8 | 10 | 20 | | |
| Echinochloa crus-galli | 10 | 15 | 17 | 20 | 27 | 35 | 50 | 70 | 80 | | |
| Alisma plantago aquatica | 3 | 8 | 10 | 12 | 16 | 20 | 25 | 30 | 35 | | |
| | | | | | I + V | | | | | | |
| | 0.25 | 0.5 | 0.75 | 0.25 | 1 | 0.25 | 1 | 0.5 | 0.75 | 1 | 0.5 |
| kg/ha | 0.25 | 0.5 | 0.25 | 0.75 | 0.25 | 1 | 0.5 | 1 | 0.75 | 1 | 1.5 |
| Crop plant: | | | | | | | | | | | |
| Oryza sativa | 0 | 0 | 0 | 0 | 0 | 0 | 0 | 0 | 0 | 0 | 0 |
| Unwanted plants: | | | | | | | | | | | |
| Cyperus esculentus | 67 | 81 | 100 | 90 | 100 | 100 | 100 | 100 | 100 | 100 | 100 |
| Echinochloa crus-galli | 65 | 80 | 77 | 85 | 85 | 90 | 90 | 96 | 91 | 100 | 100 |
| Alisma plantago aquatica | 73 | 83 | 88 | 82 | 90 | 90 | 95 | 95 | 97 | 100 | 100 |
| | | | | I + V | | | | | I + VII | | |
| | 1.5 | 1.5 | 1 | 3 | 2 | 2 | 1 | | 2 | 1 | |
| kg/ha | 0.5 | 1.5 | 3 | 1 | 2 | 1 | 2 | | 1 | 2 | |
| Oryza sativa | 0 | 0 | 5 | 0 | 0 | 0 | 0 | | 0 | 0 | |
| Cyperus esculentus | 100 | 100 | 100 | 100 | 100 | 100 | 100 | | 100 | 100 | |
| Echinochloa crus-galli | 100 | 100 | 100 | 100 | 100 | 100 | 100 | | 100 | 100 | |
| Alisma plantago aquatica | 100 | 100 | 100 | 100 | 100 | 100 | 100 | | 100 | 100 | |
| | | | | | I + VI | | | | | | |
| | 0.25 | 0.5 | 0.75 | 0.25 | 1 | 0.25 | 1 | 0.5 | 0.75 | 1 | 0.5 |
| kg/ha | 0.25 | 0.5 | 0.25 | 0.75 | 0.25 | 1 | 0.5 | 1 | 0.75 | 1 | 1.5 |
| Crop plant: | | | | | | | | | | | |
| Oryza sativa | 0 | 0 | 0 | 0 | 0 | 0 | 0 | 0 | 0 | 0 | 0 |
| Unwanted plants: | | | | | | | | | | | |
| Cyperus esculentus | 65 | 80 | 100 | 85 | 100 | 100 | 100 | 100 | 100 | 100 | 100 |
| Echinochloa crus-galli | 68 | 80 | 75 | 80 | 82 | 92 | 93 | 100 | 93 | 100 | 100 |
| Alisma plantago aquatica | 72 | 80 | 87 | 80 | 90 | 89 | 95 | 93 | 95 | 100 | 100 |
| | | | | I + VI | | | | | I + VIII | | |
| | 1.5 | 1.5 | 1 | 3 | 2 | 2 | 1 | | 2 | 1 | |

-continued

| kg/ha | 0.5 | 1.5 | 3 | 1 | 2 | 1 | 2 | | 1 | 2 | |
|---|---|---|---|---|---|---|---|---|---|---|---|
| Oryza sativa | 0 | 0 | 10 | 0 | 5 | 0 | 5 | | 0 | 0 | |
| Cyperus esculentus | 100 | 100 | 100 | 100 | 100 | 100 | 100 | | 100 | 100 | |
| Echinochloa crus-galli | 100 | 100 | 100 | 100 | 100 | 100 | 100 | | 100 | 100 | |
| Alisma plantago aquatica | 100 | 100 | 100 | 100 | 100 | 100 | 100 | | 100 | 100 | |

I + VII

| kg/ha | 0.25 / 0.25 | 0.5 / 0.5 | 0.75 / 0.25 | 0.25 / 0.75 | 1 / 0.25 | 0.25 / 1 | 1 / 0.5 | 0.5 / 1 | 0.75 / 0.75 | 1 / 1 | 0.5 / 1.5 | 1.5 / 0.5 |
|---|---|---|---|---|---|---|---|---|---|---|---|---|
| Crop plant: | | | | | | | | | | | | |
| Oryza sativa | 0 | 0 | 0 | 0 | 0 | 0 | 0 | 0 | 0 | 0 | 0 | 0 |
| Unwanted plants: | | | | | | | | | | | | |
| Cyperus esculentus | 60 | 65 | 97 | 64 | 98 | 70 | 98 | 80 | 100 | 100 | 80 | 100 |
| Echinochloa crus-galli | 62 | 70 | 72 | 75 | 77 | 80 | 80 | 89 | 83 | 95 | 100 | 90 |
| Alisma plantago aquatica | 70 | 77 | 85 | 75 | 92 | 85 | 90 | 85 | 90 | 98 | 95 | 100 |

I + VII / I + VIII

| kg/ha | 1.5 / 1.5 | 1 / 3 | 3 / 1 | 2 / 2 | | 0.25 / 0.25 | 0.5 / 0.5 | 0.75 / 0.25 | 0.25 / 0.75 | 1 / 0.25 |
|---|---|---|---|---|---|---|---|---|---|---|
| Oryza sativa | 0 | 5 | 0 | 0 | | 0 | 0 | 0 | 0 | 0 |
| Cyperus esculentus | 100 | 100 | 100 | 100 | | 58 | 65 | 96 | 63 | 97 |
| Echinochloa crus-galli | 100 | 100 | 100 | 100 | | 68 | 75 | 78 | 80 | 84 |
| Alisma plantago aquatica | 100 | 100 | 100 | 100 | | 73 | 78 | 85 | 77 | 90 |

I + VIII

| kg/ha | 0.25 / 1 | 1 / 0.5 | 0.5 / 1 | 0.75 / 0.75 | 1 / 1 | 0.5 / 1.5 | 1.5 / 0.5 | 1.5 / 1.5 | 1 / 2 | 3 / 1 | 2 / 2 |
|---|---|---|---|---|---|---|---|---|---|---|---|
| Crop plant: | | | | | | | | | | | |
| Oryza sativa | 0 | 0 | 0 | 0 | 0 | 0 | 0 | 0 | 3 | 0 | 0 |
| Unwanted plants: | | | | | | | | | | | |
| Cyperus esculentus | 67 | 98 | 80 | 98 | 100 | 90 | 100 | 100 | 100 | 100 | 100 |
| Echinochloa crus-galli | 85 | 87 | 90 | 90 | 95 | 100 | 93 | 100 | 100 | 100 | 100 |
| Alisma plantago aquatica | 88 | 93 | 91 | 90 | 95 | 94 | 100 | 100 | 100 | 100 | 100 |

I + IX

| kg/ha | 0.25 / 0.25 | 0.5 / 0.5 | 0.75 / 0.25 | 0.25 / 0.75 | 1 / 0.25 | 0.25 / 1 | 1 / 0.5 | 0.5 / 1 | 0.75 / 0.75 | 1 / 1 |
|---|---|---|---|---|---|---|---|---|---|---|
| Oryza sativa | 0 | 0 | 0 | 0 | 0 | 0 | 0 | 0 | 0 | 0 |
| Cyperus esculentus | 60 | 65 | 96 | 63 | 98 | 70 | 98 | 80 | 100 | 100 |
| Echinochloa crus-galli | 70 | 77 | 78 | 80 | 82 | 88 | 85 | 95 | 93 | 100 |
| Alisma plantago aquatica | 75 | 80 | 90 | 78 | 93 | 90 | 95 | 95 | 94 | 100 |

I + IX / II + V

| kg/ha | 0.5 / 1.5 | 1.5 / 0.5 | 1.5 / 1.5 | 1 / 2 | 3 / 1 | 2 / 2 | 0.25 / 0.25 | 0.5 / 0.5 | 0.75 / 0.25 | 0.25 / 0.75 | 1 / 0.25 |
|---|---|---|---|---|---|---|---|---|---|---|---|
| Crop plant: | | | | | | | | | | | |
| Oryza sativa | 0 | 0 | 0 | 7 | 0 | 0 | 0 | 0 | 0 | 0 | 0 |
| Unwanted plants: | | | | | | | | | | | |
| Cyperus esculentus | 90 | 100 | 100 | 100 | 100 | 100 | 60 | 78 | 80 | 80 | 90 |
| Echinochloa crus-galli | 100 | 97 | 100 | 100 | 100 | 100 | 67 | 75 | 78 | 79 | 80 |
| Alisma plantago aquatica | 96 | 100 | 100 | 100 | 100 | 100 | 60 | 71 | 74 | 67 | 89 |

II + V

| kg/ha | 0.25 / 1 | 1 / 0.5 | 0.5 / 1 | 0.75 / 0.75 | 1 / 1 | 0.5 / 1.5 | 1.5 / 0.5 | 1.5 / 1.5 | 1 / 3 | 3 / 1 | 2 / 2 |
|---|---|---|---|---|---|---|---|---|---|---|---|
| Oryza sativa | 0 | 0 | 0 | 0 | 0 | 0 | 0 | 0 | 5 | 0 | 0 |
| Cyperus esculentus | 90 | 100 | 100 | 100 | 100 | 100 | 100 | 100 | 100 | 100 | 100 |
| Echinochloa crus-galli | 90 | 90 | 92 | 91 | 100 | 100 | 96 | 100 | 100 | 100 | 100 |
| Alisma plantago aquatica | 76 | 95 | 90 | 90 | 100 | 97 | 100 | 100 | 100 | 100 | 100 |

II + VI

| kg/ha | 0.25 / 0.25 | 0.5 / 0.5 | 0.75 / 0.25 | 0.25 / 0.75 | 1 / 0.25 | 0.25 / 1 | 1 / 0.5 | 0.5 / 1 | 0.75 / 0.75 | 1 / 1 | 0.5 / 1.5 | 1.5 / 0.5 |
|---|---|---|---|---|---|---|---|---|---|---|---|---|
| Crop plant: | | | | | | | | | | | | |
| Oryza sativa | 0 | 0 | 0 | 0 | 0 | 0 | 0 | 0 | 0 | 0 | 0 | 0 |
| Unwanted plants: | | | | | | | | | | | | |
| Cyperus esculentus | 55 | 75 | 75 | 76 | 88 | 85 | 98 | 95 | 95 | 100 | 100 | 100 |
| Echinochloa crus-galli | 65 | 75 | 78 | 79 | 80 | 90 | 85 | 95 | 92 | 100 | 100 | 97 |
| Alisma plantago aquatica | 60 | 66 | 72 | 65 | 85 | 75 | 90 | 85 | 86 | 100 | 92 | 100 |

II + VI / II + VII

| kg/ha | 1.5 / 1.5 | 1 / 3 | 3 / 1 | 2 / 2 | 0.25 / 0.25 | 0.5 / 0.5 | 0.75 / 0.25 | 0.25 / 0.75 | 1 / 0.25 |
|---|---|---|---|---|---|---|---|---|---|
| Oryza sativa | 0 | 10 | 0 | 5 | 0 | 0 | 0 | 0 | 0 |
| Cyperus esculentus | 100 | 100 | 100 | 100 | 50 | 60 | 65 | 53 | 80 |
| Echinochloa crus-galli | 100 | 100 | 100 | 100 | 60 | 69 | 73 | 75 | 75 |
| Alisma plantago aquatica | 100 | 100 | 100 | 100 | 60 | 66 | 70 | 70 | 80 |

II + VII

| kg/ha | 0.25 / 1 | 1 / 0.5 | 0.5 / 1 | 0.75 / 0.75 | 1 / 1 | 0.5 / 1.5 | 1.5 / 0.5 | 1.5 / 1.5 | 1 / 3 | 3 / 1 | 2 / 2 |
|---|---|---|---|---|---|---|---|---|---|---|---|
| Crop plant: | | | | | | | | | | | |
| Oryza sativa | 0 | 0 | 0 | 0 | 0 | 0 | 0 | 0 | 5 | 0 | 0 |
| Unwanted plants: | | | | | | | | | | | |
| Cyperus esculentus | 65 | 85 | 70 | 82 | 87 | 80 | 100 | 100 | 100 | 100 | 100 |
| Echinochloa crus-galli | 82 | 84 | 85 | 85 | 90 | 100 | 92 | 100 | 100 | 100 | 100 |
| Alisma plantago aquatica | 80 | 90 | 80 | 80 | 93 | 90 | 100 | 100 | 100 | 100 | 100 |

II + VIII

| kg/ha | 0.25 / 0.25 | 0.5 / 0.5 | 0.75 / 0.25 | 0.25 / 0.75 | 1 / 0.25 | 0.25 / 1 | 1 / 0.5 | 0.5 / 1 | 0.75 / 0.75 | 1 / 1 |
|---|---|---|---|---|---|---|---|---|---|---|
| Oryza sativa | 0 | 0 | 0 | 0 | 0 | 0 | 0 | 0 | 0 | 0 |
| Cyperus esculentus | 50 | 60 | 70 | 53 | 80 | 65 | 85 | 70 | 80 | 88 |
| Echinochloa crus-galli | 65 | 72 | 75 | 79 | 80 | 82 | 85 | 85 | 88 | 92 |

-continued

| | | | | | | | | | | | | |
|---|---|---|---|---|---|---|---|---|---|---|---|---|
| Alisma plantago aquatica | 60 | 65 | 73 | 64 | 85 | 70 | 88 | 80 | 85 | 94 | | |
| | | II+ VIII | | | | | II + IX | | | | | |
| | 0.5 | 1.5 | 1.5 | 1 | 3 | 2 | 0.25 | 0.5 | 0.75 | 0.25 | 1 | |
| kg/ha | 1.5 | 0.5 | 1.5 | 3 | 1 | 2 | 0.25 | 0.5 | 0.25 | 0.75 | 0.25 | |
| Crop plant: | | | | | | | | | | | | |
| Oryza sativa | 0 | 0 | 0 | 3 | 0 | 0 | 0 | 0 | 0 | 0 | 0 | |
| Unwanted plants: | | | | | | | | | | | | |
| Cyperus esculentus | 83 | 100 | 100 | 100 | 100 | 100 | 51 | 60 | 68 | 54 | 80 | |
| Echinochloa crus-galli | 100 | 95 | 100 | 100 | 100 | 100 | 65 | 75 | 77 | 80 | 80 | |
| Alisma plantago aquatica | 90 | 100 | 100 | 100 | 100 | 100 | 60 | 66 | 74 | 65 | 88 | |
| | | | | | II + IX | | | | | | | |
| | 0.25 | 1 | 0.5 | 0.75 | 1 | 0.5 | 1.5 | 1.5 | 1 | 3 | 2 | |
| kg/ha | 1 | 0.5 | 1 | 0.75 | 1 | 1.5 | 0.5 | 1.5 | 3 | 1 | 2 | |
| Oryza sativa | 0 | 0 | 0 | 0 | 0 | 0 | 0 | 0 | 7 | 0 | 0 | |
| Cyperus esculentus | 63 | 85 | 72 | 80 | 90 | 70 | 100 | 100 | 100 | 100 | 100 | |
| Echinochloa crus-galli | 85 | 85 | 90 | 95 | 100 | 100 | 100 | 100 | 100 | 100 | 100 | |
| Alisma plantago aquatica | 75 | 90 | 75 | 84 | 95 | 85 | 100 | 100 | 100 | 100 | 100 | |
| | | | | | III + V | | | | | | | |
| | 0.25 | 0.5 | 0.75 | 0.25 | 1 | 0.25 | 1 | 0.5 | 0.75 | 1 | 0.5 | 1.5 |
| kg/ha | 0.25 | 0.5 | 0.25 | 0.75 | 0.25 | 1 | 0.5 | 1 | 0.75 | 1 | 1.5 | 0.5 |
| Crop plant: | | | | | | | | | | | | |
| Oryza sativa | 0 | 0 | 0 | 0 | 0 | 0 | 0 | 0 | 0 | 0 | 0 | 0 |
| Unwanted plants: | | | | | | | | | | | | |
| Cyperus esculentus | 63 | 78 | 85 | 85 | 95 | 95 | 100 | 100 | 100 | 100 | 100 | 100 |
| Echinochloa crus-galli | 67 | 79 | 80 | 80 | 83 | 90 | 95 | 100 | 93 | 100 | 100 | 97 |
| Alisma plantago aquatica | 60 | 75 | 77 | 78 | 90 | 80 | 97 | 92 | 90 | 100 | 98 | 100 |
| | | III + V | | | | | III + VI | | | | | |
| | 1.5 | 1 | 3 | 2 | | 0.25 | 0.5 | 0.75 | 0.25 | 1 | | |
| kg/ha | 1.5 | 3 | 1 | 2 | | 0.25 | 0.5 | 0.25 | 0.75 | 0.25 | | |
| Oryza sativa | 0 | 5 | 0 | 0 | | 0 | 0 | 0 | 0 | 0 | | |
| Cyperus esculentus | 100 | 100 | 100 | 100 | | 62 | 78 | 80 | 80 | 90 | | |
| Echinochloa crus-galli | 100 | 100 | 100 | 100 | | 70 | 79 | 80 | 80 | 82 | | |
| Alisma plantago aquatica | 100 | 100 | 100 | 100 | | 60 | 70 | 77 | 65 | 90 | | |
| | | | | | III + VI | | | | | | | |
| | 0.25 | 1 | 0.5 | 0.75 | 1 | 0.5 | 1.5 | 1.5 | 1 | 3 | 2 | |
| kg/ha | 1 | 0.5 | 1 | 0.75 | 1 | 1.5 | 0.5 | 1.5 | 3 | 1 | 2 | |
| Crop plant: | | | | | | | | | | | | |
| Oryza sativa | 0 | 0 | 0 | 0 | 0 | 0 | 0 | 0 | 10 | 0 | 5 | |
| Unwanted plants: | | | | | | | | | | | | |
| Cyperus esculentus | 90 | 100 | 95 | 100 | 100 | 100 | 100 | 100 | 100 | 100 | 100 | |
| Echinochloa crus-galli | 92 | 85 | 97 | 94 | 100 | 100 | 98 | 100 | 100 | 100 | 100 | |
| Alisma plantago aquatica | 80 | 92 | 90 | 90 | 100 | 95 | 100 | 100 | 100 | 100 | 100 | |
| | | | | III + VII | | | | | | | | |
| | 0.25 | 0.5 | 0.75 | 0.25 | 1 | 0.25 | 1 | 0.5 | 0.75 | 1 | | |
| kg/ha | 0.25 | 0.5 | 0.25 | 0.75 | 0.25 | 1 | 0.5 | 1 | 0.75 | 1 | | |
| Oryza sativa | 0 | 0 | 0 | 0 | 0 | 0 | 0 | 0 | 0 | 0 | | |
| Cyperus esculentus | 56 | 60 | 74 | 59 | 82 | 65 | 85 | 70 | 84 | 88 | | |
| Echinochloa crus-galli | 65 | 70 | 73 | 74 | 77 | 85 | 80 | 90 | 87 | 95 | | |
| Alisma plantago aquatica | 60 | 70 | 75 | 63 | 90 | 75 | 92 | 84 | 82 | 95 | | |
| | | | | III + VII | | | | III + VIII | | | | |
| | 0.5 | 1.5 | 1.5 | 1 | 3 | 2 | 0.25 | 0.5 | 0.75 | 0.25 | 1 | |
| kg/ha | 1.5 | 0.5 | 1.5 | 3 | 1 | 2 | 0.25 | 0.5 | 0.25 | 0.75 | 0.25 | |
| Crop plant: | | | | | | | | | | | | |
| Oryza sativa | 0 | 0 | 0 | 5 | 0 | 0 | 0 | 0 | 0 | 0 | 0 | |
| Unwanted plants: | | | | | | | | | | | | |
| Cyperus esculentus | 80 | 100 | 100 | 90 | 100 | 100 | 57 | 60 | 73 | 60 | 82 | |
| Echinochloa crus-galli | 100 | 92 | 100 | 100 | 100 | 100 | 69 | 77 | 78 | 80 | 83 | |
| Alisma plantago aquatica | 94 | 100 | 100 | 100 | 100 | 100 | 60 | 70 | 76 | 64 | 90 | |
| | | | | III + VIII | | | | | | | | |
| | 0.25 | 1 | 0.5 | 0.75 | 1 | 0.5 | 1.5 | 1.5 | 1 | 3 | 2 | |
| kg/ha | 1 | 0.5 | 1 | 0.75 | 1 | 1.5 | 0.5 | 1.5 | 3 | 1 | 2 | |
| Oryza sativa | 0 | 0 | 0 | 0 | 0 | 0 | 0 | 0 | 3 | 0 | 0 | |
| Cyperus esculentus | 65 | 85 | 70 | 83 | 88 | 80 | 100 | 100 | 100 | 100 | 100 | |
| Echinochloa crus-galli | 85 | 88 | 90 | 89 | 95 | 100 | 93 | 100 | 100 | 100 | 100 | |
| Alisma plantago aquatica | 78 | 93 | 80 | 85 | 96 | 90 | 100 | 100 | 100 | 100 | 100 | |
| | | | | III + | IX | | | | | | | |
| | 0.25 | 0.5 | 0.75 | 0.25 | 1 | 0.25 | 1 | 0.5 | 0.75 | 1 | 0.5 | |
| kg/ha | 0.25 | 0.5 | 0.25 | 0.75 | 0.25 | 1 | 0.5 | 1 | 0.75 | 1 | 1.5 | |
| Crop plant: | | | | | | | | | | | | |
| Oryza sativa | 0 | 0 | 0 | 0 | 0 | 0 | 0 | 0 | 0 | 0 | 0 | |
| Unwanted plants: | | | | | | | | | | | | |
| Cyperus esculentus | 56 | 60 | 72 | 60 | 80 | 63 | 85 | 70 | 80 | 88 | 80 | |
| Echinochloa crus-galli | 68 | 77 | 79 | 80 | 80 | 90 | 85 | 93 | 94 | 98 | 100 | |
| Alisma plantago aquatica | 60 | 70 | 75 | 62 | 90 | 75 | 92 | 82 | 80 | 97 | 94 | |
| | | III + IX | | | | | IV + V | | | | | |
| | 1.5 | 1.5 | 3 | 3 | 2 | | 0.25 | 0.5 | 0.75 | 0.25 | 1 | |
| kg/ha | 0.5 | 1.5 | 3 | 1 | 2 | | 0.25 | 0.5 | 0.25 | 0.75 | 0.25 | |
| Oryza sativa | 0 | 0 | 7 | 0 | 0 | | 0 | 0 | 0 | 0 | 0 | |
| Cyperus esculentus | 100 | 100 | 100 | 100 | 100 | | 60 | 82 | 80 | 80 | 98 | |
| Echinochloa crus-galli | 95 | 100 | 100 | 100 | 100 | | 72 | 80 | 80 | 83 | 85 | |
| Alisma plantago aquatica | 100 | 100 | 100 | 100 | 100 | | 61 | 75 | 79 | 70 | 98 | |
| | | | | | IV + V | | | | | | | |
| | 0.25 | 1 | 0.5 | 0.75 | 1 | 0.5 | 1.5 | 1.5 | 1 | 3 | 2 | |
| kg/ha | 1 | 0.5 | 1 | 0.75 | 1 | 1.5 | 0.5 | 1.5 | 3 | 1 | 2 | |

-continued

| Crop plant: | | | | | | | | | | | |
|---|---|---|---|---|---|---|---|---|---|---|---|
| Oryza sativa | 0 | 0 | 0 | 0 0 | 0 | 0 | 0 | 5 | 0 | 0 | |
| Unwanted plants: | | | | | | | | | | | |
| Cyperus esculentus | 90 | 100 | 100 | 100 100 | 100 | 100 | 100 | 100 | 100 | 100 | |
| Echinochloa crus-galli | 93 | 95 | 97 | 90 100 | 100 | 100 | 100 | 100 | 100 | 100 | |
| Alisma plantago aquatica | 80 | 100 | 88 | 90 100 | 100 | 100 | 100 | 100 | 100 | 100 | |
| | | | | IV + VI | | | | | | | |
| kg/ha | 0.25 | 0.5 | 0.75 | 0.25 1 | 0.25 | 1 | 0.5 | 0.75 | 1 | | |
| | 0.25 | 0.5 | 0.25 | 0.75 0.25 | 1 | 0.5 | 1 | 0.75 | 1 | | |

| Oryza sativa | 0 | 0 | 0 | 0 0 | 0 | 0 | 0 | 0 | 0 | | |
|---|---|---|---|---|---|---|---|---|---|---|---|
| Cyperus esculentus | 56 | 83 | 75 | 75 90 | 85 | 100 | 100 | 95 | 100 | | |
| Echinochloa crus-galli | 70 | 80 | 80 | 83 85 | 98 | 87 | 100 | 98 | 100 | | |
| Alisma plantago aquatica | 62 | 70 | 80 | 76 96 | 80 | 97 | 90 | 95 | 100 | | |
| | | | IV + VI | | | | IV + VII | | | | |
| kg/ha | 0.5 | 1.5 | 1.5 | 1 3 | 2 | 0.25 | 0.5 | 0.75 | 0.25 | 1 | 0.25 |
| | 1.5 | 0.5 | 1.5 | 3 1 | 2 | 0.25 | 0.5 | 0.25 | 0.75 | 0.25 | 1 |

| Crop plant: | | | | | | | | | | | |
|---|---|---|---|---|---|---|---|---|---|---|---|
| Oryza sativa | 0 | 0 | 0 | 10 0 | 5 | 0 | 0 | 0 | 0 | 0 | 0 |
| Unwanted plants: | | | | | | | | | | | |
| Cyperus esculentus | 100 | 100 | 100 | 100 100 | 100 | 50 | 65 | 70 | 64 | 88 | 68 |
| Echinochloa crus-galli | 100 | 98 | 100 | 100 100 | 100 | 66 | 75 | 75 | 78 | 80 | 85 |
| Alisma plantago aquatica | 95 | 100 | 100 | 100 100 | 100 | 61 | 70 | 79 | 65 | 97 | 70 |
| | | | | IV + VII | | | | | | | |
| kg/ha | 1 | 0.5 | 0.75 | 1 0.5 | 1.5 | 1.5 | 1 | 3 | 2 | | |
| | 0.5 | 1 | 0.75 | 1 1.5 | 0.5 | 1.5 | 3 | 1 | 2 | | |

| Oryza sativa | 0 | 0 | 0 | 0 0 | 0 | 0 | 5 | 0 | 0 | | |
|---|---|---|---|---|---|---|---|---|---|---|---|
| Cyperus esculentus | 90 | 82 | 84 | 94 100 | 100 | 100 | 100 | 100 | 100 | | |
| Echinochloa crus-galli | 87 | 90 | 85 | 97 100 | 98 | 100 | 100 | 100 | 100 | | |
| Alisma plantago aquatica | 98 | 80 | 83 | 100 98 | 100 | 100 | 100 | 100 | 100 | | |
| | | | | IV + VIII | | | | | | | |
| kg/ha | 0.25 | 0.5 | 0.75 | 0.25 1 | 0.25 | 1 | 0.5 | 0.75 | 1 | 0.5 | |
| | 0.25 | 0.5 | 0.25 | 0.75 0.25 | 1 | 0.5 | 1 | 0.75 | 1 | 1.5 | |

| Crop plant: | | | | | | | | | | | |
|---|---|---|---|---|---|---|---|---|---|---|---|
| Oryza sativa | 0 | 0 | 0 | 0 0 | 0 | 0 | 0 | 0 | 0 | 0 | |
| Unwanted plants: | | | | | | | | | | | |
| Cyperus esculentus | 50 | 63 | 70 | 54 88 | 65 | 90 | 67 | 80 | 93 | 95 | |
| Echinochloa crus-galli | 71 | 77 | 78 | 80 82 | 88 | 90 | 90 | 92 | 97 | 100 | |
| Alisma plantago aquatica | 61 | 70 | 79 | 65 95 | 77 | 97 | 80 | 80 | 100 | 88 | |
| | | IV + VIII | | | | | IV + IX | | | | |
| kg/ha | 1.5 | 1.5 | 1 | 3 2 | | 0.25 | 0.5 | 0.75 | 0.25 | 1 | |
| | 0.5 | 1.5 | 3 | 1 2 | | 0.25 | 0.5 | 0.25 | 0.75 | 0.25 | |

| Oryza sativa | 0 | 0 | 3 | 0 0 | | 0 | 0 | 0 | 0 | 0 | |
|---|---|---|---|---|---|---|---|---|---|---|---|
| Cyperus esculentus | 100 | 100 | 100 | 100 100 | | 52 | 65 | 70 | 55 | 88 | |
| Echinochloa crus-galli | 95 | 100 | 100 | 100 100 | | 70 | 78 | 80 | 86 | 88 | |
| Alisma plantago aquatica | 100 | 100 | 100 | 100 100 | | 61 | 70 | 80 | 65 | 95 | |
| | | | | IV + IX | | | | | | | |
| kg/ha | 0.25 | 1 | 0.5 | 0.75 1 | 0.5 | 1.5 | 1.5 | 1 | 3 | 2 | |
| | 1 | 0.5 | 1 | 0.75 1 | 1.5 | 0.5 | 1.5 | 3 | 1 | 2 | |

| Crop plant: | | | | | | | | | | | |
|---|---|---|---|---|---|---|---|---|---|---|---|
| Oryza sativa | 0 | 0 | 0 | 0 0 | 0 | 0 | 0 | 7 | 0 | 0 | |
| Unwanted plants: | | | | | | | | | | | |
| Cyperus esculentus | 65 | 95 | 80 | 80 98 | 94 | 100 | 100 | 100 | 100 | 100 | |
| Echinochloa crus-galli | 91 | 93 | 95 | 96 100 | 100 | 100 | 100 | 100 | 100 | 100 | |
| Alisma plantago aquatica | 80 | 100 | 80 | 83 100 | 96 | 100 | 100 | 100 | 100 | 100 | |
| | | | | I + XXIV | | | | | | | |
| kg/ha | 0.25 | 0.5 | 0.75 | 0.25 1 | 0.25 | 1 | 0.5 | 0.75 | 1 | | |
| | 0.25 | 0.5 | 0.25 | 0.75 0.25 | 1 | 0.5 | 1 | 0.75 | 1 | | |

| Oryza sativa | 0 | 0 | 0 | 0 0 | 0 | 0 | 0 | 0 | 0 | | |
|---|---|---|---|---|---|---|---|---|---|---|---|
| Cyperus esculentus | 60 | 67 | 98 | 62 98 | 70 | 100 | 80 | 100 | 100 | | |
| Echinochloa crus-galli | 50 | 62 | 58 | 60 65 | 65 | 67 | 70 | 68 | 80 | | |
| Alisma plantago aquatica | 78 | 90 | 92 | 90 95 | 94 | 100 | 96 | 100 | 100 | | |
| | | | I + XXIV | | | | I + XXV | | | | |
| kg/ha | 0.5 | 1.5 | 1.5 | 1 3 | 2 | 0.25 | 0.5 | 0.75 | 0.25 | 1 | |
| | 1.5 | 0.5 | 1.5 | 3 1 | 2 | 0.25 | 0.5 | 0.25 | 0.75 | 0.25 | |

| Crop plant: | | | | | | | | | | | |
|---|---|---|---|---|---|---|---|---|---|---|---|
| Oryza sativa | 0 | 0 | 0 | 0 5 | 0 | 0 | 0 | 0 | 0 | 0 | |
| Unwanted destruction: | | | | | | | | | | | |
| Cyperus esculentus | 85 | 100 | 100 | 100 100 | 100 | 58 | 65 | 97 | 67 | 98 | |
| Echinochloa crus-galli | 83 | 80 | 93 | 100 95 | 100 | 55 | 65 | 63 | 65 | 67 | |
| Alisma plantago aquatica | 100 | 100 | 100 | 100 100 | 100 | 75 | 80 | 90 | 90 | 95 | |
| | | | | I + XXV | | | | | | | |
| kg/ha | 0.25 | 1 | 0.5 | 0.75 1 | 0.5 | 1.5 | 1.5 | 1 | 3 | 2 | |
| | 1 | 0.5 | 1 | 0.75 1 | 1.5 | 0.5 | 1.5 | 2 | 1 | 2 | |

| Oryza sativa | 0 | 0 | 0 | 0 0 | 0 | 0 | 0 | 5 | 0 | 0 | |
|---|---|---|---|---|---|---|---|---|---|---|---|
| Cyperus esculentus | 70 | 100 | 80 | 100 100 | 87 | 100 | 100 | 100 | 100 | 100 | |
| Echinochloa grus-galli | 70 | 70 | 75 | 73 80 | 85 | 80 | 95 | 100 | 98 | 100 | |
| Alisma plantago aquatica | 96 | 100 | 100 | 100 100 | 100 | 100 | 100 | 100 | 100 | 100 | |
| | | | | I + XXVI | | | | | | | |
| kg/ha | 0.25 | 0.5 | 0.75 | 0.25 1 | 0.25 | 1 | 0.5 | 0.75 | 1 | 0.5 | |
| | 0.25 | 0.5 | 0.25 | 0.75 0.25 | 1 | 0.5 | 1 | 0.75 | 1 | 1.5 | |

| Crop plant: | | | | | | | | | | | |
|---|---|---|---|---|---|---|---|---|---|---|---|
| Oryza sativa | 0 | 0 | 0 | 0 0 | 0 | 0 | 0 | 0 | 0 | 0 | |
| Unwanted plants: | | | | | | | | | | | |
| Cyperus esculentus | 57 | 65 | 96 | 67 98 | 68 | 98 | 83 | 100 | 100 | 85 | |
| Echinochloa crus-galli | 50 | 60 | 58 | 57 63 | 65 | 68 | 70 | 70 | 74 | 80 | |

-continued

| | | | | | | | | | | | |
|---|---|---|---|---|---|---|---|---|---|---|---|
| Alisma plantago aquatica | 75 | 85 | 90 | 85 | 95 | 87 | 100 | 96 | 100 | 100 | 100 |

| | I + XXVI | | | | | | II + XXIV | | | | |
|---|---|---|---|---|---|---|---|---|---|---|---|
| kg/ha | 1.5 | 1.5 | 1 | 3 | 2 | | 0.25 | 0.5 | 0.75 | 0.25 | 1 |
| | 0.5 | 1.5 | 3 | 1 | 2 | | 0.25 | 0.5 | 0.25 | 0.75 | 0.25 |

| | | | | | | | | | | | |
|---|---|---|---|---|---|---|---|---|---|---|---|
| Oryza sativa | 0 | 0 | 0 | 0 | 0 | | 0 | 0 | 0 | 0 | 0 |
| Cyperus esculentus | 100 | 100 | 100 | 100 | 100 | | 50 | 58 | 68 | 60 | 85 |
| Echinochloa crus-galli | 75 | 90 | 100 | 91 | 100 | | 50 | 57 | 60 | 60 | 63 |
| Alisma plantago aquatica | 100 | 100 | 100 | 100 | 100 | | 65 | 76 | 78 | 75 | 90 |

| | II + | | | | XXIV | | | | | | |
|---|---|---|---|---|---|---|---|---|---|---|---|
| kg/ha | 0.25 | 1 | 0.5 | 0.75 | 1 | 0.5 | 1.5 | 1.5 | 1 | 3 | 2 |
| | 1 | 0.5 | 1 | 0.75 | 1 | 1.5 | 0.5 | 1.5 | 3 | 1 | 2 |

| | | | | | | | | | | | |
|---|---|---|---|---|---|---|---|---|---|---|---|
| Crop plant: | | | | | | | | | | | |
| Oryza sativa | 0 | 0 | 0 | 0 | 0 | 0 | 0 | 0 | 5 | 0 | 0 |
| Unwanted plants: | | | | | | | | | | | |
| Cyperus esculentus | 65 | 87 | 70 | 72 | 89 | 77 | 100 | 100 | 100 | 100 | 100 |
| Echinochloa crus-galli | 65 | 67 | 68 | 70 | 75 | 78 | 80 | 96 | 100 | 100 | 100 |
| Alisma plantago aquatica | 79 | 98 | 90 | 90 | 95 | 100 | 100 | 100 | 100 | 100 | 100 |

| | II + | | | | XXV | | | | | | |
|---|---|---|---|---|---|---|---|---|---|---|---|
| kg/ha | 0.25 | 0.5 | 0.75 | 0.25 | 1 | 0.25 | 1 | 0.5 | 0.75 | 1 | |
| | 0.25 | 0.5 | 0.25 | 0.75 | 0.25 | 1 | 0.5 | 1 | 0.75 | 1 | |

| | | | | | | | | | | |
|---|---|---|---|---|---|---|---|---|---|---|
| Oryza sativa | 0 | 0 | 0 | 0 | 0 | 0 | 0 | 0 | 0 | 0 |
| Cyperus esculentus | 50 | 60 | 67 | 60 | 80 | 61 | 85 | 80 | 79 | 88 |
| Echinochloa crus-galli | 55 | 60 | 62 | 65 | 68 | 70 | 73 | 72 | 75 | 80 |
| Alisma plantago aquatica | 60 | 75 | 79 | 78 | 90 | 85 | 97 | 93 | 95 | 100 |

| | II + XXV | | | | | II + XXVI | | | | |
|---|---|---|---|---|---|---|---|---|---|---|
| kg/ha | 0.5 | 1.5 | 1.5 | 1 | 3 | 2 | 0.25 | 0.5 | 0.75 | 0.25 | 1 |
| | 1.5 | 0.5 | 1.5 | 3 | 1 | 2 | 0.25 | 0.5 | 0.25 | 0.75 | 0.25 |

| | | | | | | | | | | | |
|---|---|---|---|---|---|---|---|---|---|---|---|
| Crop plant: | | | | | | | | | | | |
| Oryza sativa | 0 | 0 | 0 | 5 | 0 | 0 | 0 | 0 | 0 | 0 | 0 |
| Unwanted plants: | | | | | | | | | | | |
| Cyperus esculentus | 83 | 100 | 100 | 100 | 100 | 100 | 49 | 57 | 69 | 53 | 80 |
| Echinochloa crus-galli | 80 | 82 | 98 | 100 | 100 | 100 | 50 | 55 | 58 | 57 | 60 |
| Alisma plantago aquatica | 100 | 100 | 100 | 100 | 100 | 100 | 62 | 71 | 75 | 70 | 90 |

| | | | | | II + XXVI | | | | | | |
|---|---|---|---|---|---|---|---|---|---|---|---|
| kg/ha | 0.25 | 1 | 0.5 | 0.75 | 1 | 0.5 | 1.5 | 1.5 | 1 | 3 | 2 |
| | 1 | 0.5 | 1 | 0.75 | 1 | 1.5 | 0.5 | 1.5 | 3 | 1 | 2 |

| | | | | | | | | | | | |
|---|---|---|---|---|---|---|---|---|---|---|---|
| Oryza sativa | 0 | 0 | 0 | 0 | 0 | 0 | 0 | 0 | 0 | 0 | 0 |
| Cyperus esculentus | 65 | 84 | 70 | 82 | 87 | 80 | 100 | 100 | 100 | 100 | 100 |
| Echinochloa crus-galli | 60 | 65 | 63 | 65 | 70 | 75 | 78 | 95 | 100 | 100 | 100 |
| Alisma plantago aquatica | 77 | 96 | 85 | 84 | 98 | 92 | 100 | 100 | 100 | 100 | 100 |

| | III + | | | | XXIV | | | | | | |
|---|---|---|---|---|---|---|---|---|---|---|---|
| kg/ha | 0.25 | 0.5 | 0.75 | 0.25 | 1 | 0.25 | 1 | 0.5 | 0.75 | 1 | 0.5 |
| | 0.25 | 0.5 | 0.25 | 0.75 | 0.25 | 1 | 0.5 | 1 | 0.75 | 1 | 1.5 |

| | | | | | | | | | | | |
|---|---|---|---|---|---|---|---|---|---|---|---|
| Crop plant: | | | | | | | | | | | |
| Oryza sativa | 0 | 0 | 0 | 0 | 0 | 0 | 0 | 0 | 0 | 0 | 0 |
| Unwanted plants: | | | | | | | | | | | |
| Cyperus esculentus | 53 | 60 | 73 | 55 | 80 | 60 | 85 | 70 | 80 | 88 | 75 |
| Echinochloa crus-galli | 50 | 62 | 59 | 60 | 63 | 65 | 67 | 70 | 69 | 75 | 83 |
| Alisma plantago aquatica | 65 | 80 | 80 | 75 | 94 | 83 | 98 | 95 | 100 | 98 | |

| | III 30 XXIV | | | | | | III + XXV | | | | |
|---|---|---|---|---|---|---|---|---|---|---|---|
| kg/ha | 1.5 | 1.5 | 1 | 3 | 2 | | 0.25 | 0.5 | 0.75 | 0.25 | 1 |
| | 0.5 | 1.5 | 3 | 1 | 2 | | 0.25 | 0.5 | 0.25 | 0.75 | 0.25 |

| | | | | | | | | | | | |
|---|---|---|---|---|---|---|---|---|---|---|---|
| Oryza sativa | 0 | 0 | 5 | 0 | 0 | | 0 | 0 | 0 | 0 | 0 |
| Cyperus esculentus | 100 | 100 | 100 | 100 | 100 | | 56 | 60 | 75 | 59 | 80 |
| Echinochloa crus-galli | 72 | 92 | 100 | 95 | 100 | | 57 | 62 | 64 | 65 | 68 |
| Alisma plantago aquatica | 100 | 100 | 100 | 100 | 100 | | 63 | 78 | 80 | 78 | 94 |

| | III + | | | | XXV | | | | | | |
|---|---|---|---|---|---|---|---|---|---|---|---|
| kg/ha | 0.25 | 1 | 0.5 | 0.75 | 1 | 0.5 | 1.5 | 1.5 | 1 | 3 | 2 |
| | 1 | 0.5 | 1 | 0.75 | 1 | 1.5 | 0.5 | 1.5 | 3 | 1 | 2 |

| | | | | | | | | | | | |
|---|---|---|---|---|---|---|---|---|---|---|---|
| Crop plant: | | | | | | | | | | | |
| Oryza sativa | 0 | 0 | 0 | 0 | 0 | 0 | 0 | 0 | 5 | 0 | 0 |
| Unwanted plants: | | | | | | | | | | | |
| Cyperus esculentus | 65 | 85 | 70 | 80 | 87 | 78 | 100 | 100 | 100 | 100 | 100 |
| Echinochloa crus-galli | 70 | 73 | 75 | 74 | 80 | 85 | 80 | 95 | 100 | 98 | 100 |
| Alisma plantago aquatica | 85 | 98 | 96 | 97 | 100 | 100 | 100 | 100 | 100 | 100 | 100 |

| | III + XXVI | | | | | | | | | |
|---|---|---|---|---|---|---|---|---|---|---|
| kg/ha | 0.25 | 0.5 | 0.75 | 0.25 | 1 | 0.25 | 1 | 0.5 | 0.75 | 1 |
| | 0.25 | 0.5 | 0.25 | 0.75 | 0.25 | 1 | 0.5 | 1 | 0.75 | 1 |

| | | | | | | | | | | |
|---|---|---|---|---|---|---|---|---|---|---|
| Oryza sativa | 0 | 0 | 0 | 0 | 0 | 0 | 0 | 0 | 0 | 0 |
| Cyperus esculentus | 55 | 60 | 70 | 58 | 85 | 60 | 89 | 72 | 85 | 90 |
| Echinochloa crus-galli | 50 | 60 | 60 | 60 | 64 | 63 | 67 | 65 | 70 | 72 |
| Alisma plantago aquatica | 60 | 76 | 80 | 71 | 98 | 78 | 100 | 90 | 90 | 100 |

| | III + XXVI | | | | | IV + XXIV | | | | |
|---|---|---|---|---|---|---|---|---|---|---|
| kg/ha | 0.5 | 1.5 | 1.5 | 1 | 3 | 2 | 0.25 | 0.5 | 0.75 | 0.25 | 1 |
| | 1.5 | 0.5 | 1.5 | 3 | 1 | 2 | 0.25 | 0.5 | 0.25 | 0.75 | 0.25 |

| | | | | | | | | | | | |
|---|---|---|---|---|---|---|---|---|---|---|---|
| Crop plant: | | | | | | | | | | | |
| Oryza sativa | 0 | 0 | 0 | 0 | 0 | 0 | 0 | 0 | 0 | 0 | 0 |
| Unwanted plants: | | | | | | | | | | | |
| Cyperus esculentus | 82 | 100 | 100 | 100 | 100 | 100 | 50 | 65 | 70 | 55 | 86 |
| Echinochloa crus-galli | 80 | 82 | 95 | 100 | 95 | 100 | 53 | 62 | 60 | 63 | 65 |
| Alisma plantago aquatica | 95 | 100 | 100 | 100 | 100 | 100 | 61 | 80 | 82 | 76 | 96 |

| | | | | IV + XXIV | | | | | | | |
|---|---|---|---|---|---|---|---|---|---|---|---|
| kg/ha | 0.25 | 1 | 0.5 | 0.75 | 1 | 0.5 | 1.5 | 1.5 | 1 | 3 | 2 |
| | 1 | 0.5 | 1 | 0.75 | 1 | 1.5 | 0.5 | 1.5 | 3 | 1 | 2 |

-continued

| | | | | | | | | | | | |
|---|---|---|---|---|---|---|---|---|---|---|---|
| Oryza sativa | 0 | 0 | 0 | 0 | 0 | 0 | 0 | 0 | 5 | 0 | 0 |
| Cyperus esculentus | 60 | 90 | 73 | 80 | 94 | 100 | 100 | 100 | 100 | 100 | 100 |
| Echinochloa crus-galli | 68 | 70 | 70 | 72 | 77 | 83 | 78 | 98 | 100 | 100 | 100 |
| Alisma plantago aquatica | 85 | 100 | 98 | 97 | 100 | 98 | 100 | 100 | 100 | 100 | 100 |
| | | | | | IV + XXV | | | | | | |
| | 0.25 | 0.5 | 0.75 | 0.25 | 1 | 0.25 | 1 | 0.5 | 0.75 | 1 | 0.5 |
| kg/ha | 0.25 | 0.5 | 0.25 | 0.75 | 0.25 | 1 | 0.5 | 1 | 0.25 | 1 | 1.5 |

| | | | | | | | | | | | |
|---|---|---|---|---|---|---|---|---|---|---|---|
| Crop plant: | | | | | | | | | | | |
| Oryza sativa | 0 | 0 | 0 | 0 | 0 | 0 | 0 | 0 | 0 | 0 | 0 |
| Unwanted plants: | | | | | | | | | | | |
| Cyperus esculentus | 50 | 65 | 70 | 57 | 86 | 60 | 90 | 75 | 88 | 93 | 90 |
| Echinochloa crus-galli | 58 | 65 | 65 | 68 | 70 | 73 | 74 | 75 | 75 | 82 | 85 |
| Alisma plantago aquatica | 65 | 75 | 80 | 79 | 96 | 86 | 100 | 95 | 98 | 100 | 100 |
| | | IV + XXV | | | | | | IV + XXVI | | | |
| | 1.5 | 1.5 | 1 | 3 | 2 | 0.25 | 0.5 | 0.75 | 0.25 | 1 | |
| kg/ha | 0.5 | 1.5 | 3 | 1 | 2 | 0.25 | 0.5 | 0.25 | 0.75 | 0.25 | |

| | | | | | | | | | | | |
|---|---|---|---|---|---|---|---|---|---|---|---|
| Oryza sativa | 0 | 0 | 5 | 0 | 0 | | 0 | 0 | 0 | 0 | 0 |
| Cyperus esculentus | 100 | 100 | 100 | 100 | 100 | | 52 | 65 | 70 | 55 | 87 |
| Echinochloa crus-galli | 80 | 95 | 100 | 100 | 100 | | 53 | 60 | 60 | 62 | 65 |
| Alisma plantago aquatica | 100 | 100 | 100 | 100 | 100 | | 64 | 78 | 83 | 70 | 95 |
| | | | | | IV + XXVI | | | | | | |
| | 0.25 | 1 | 0.5 | 0.75 | 1 | 0.5 | 1.5 | 1.5 | 1 | 3 | 2 |
| kg/ha | 1 | 0.5 | 1 | 0.75 | 1 | 1.5 | 0.5 | 1.5 | 3 | 1 | 2 |

| | | | | | | | | | | | |
|---|---|---|---|---|---|---|---|---|---|---|---|
| Crop plant: | | | | | | | | | | | |
| Oryza sativa | 0 | 0 | 0 | 0 | 0 | 0 | 0 | 0 | 0 | 0 | 0 |
| Unwanted plants: | | | | | | | | | | | |
| Cyperus esculentus | 65 | 90 | 74 | 75 | 94 | 90 | 100 | 100 | 100 | 100 | 100 |
| Echinochloa crus-galli | 65 | 67 | 70 | 70 | 73 | 80 | 75 | 95 | 100 | 97 | 100 |
| Alisma plantago aquatica | 83 | 98 | 85 | 96 | 100 | 98 | 100 | 100 | 100 | 100 | 100 |
| | I + IX | | II + V | | II + VI | | II + VII | | II + VIII | | II + IX |
| | 2 | 1 | 2 | 1 | 2 | 1 | 2 | 1 | 2 | 1 | 2 |
| kg/ha | 1 | 2 | 1 | 2 | 1 | 2 | 1 | 2 | 1 | 2 | 1 | 2 |

| | | | | | | | | | | |
|---|---|---|---|---|---|---|---|---|---|---|
| Crop plant: | | | | | | | | | | |
| Oryza sativa | 0 | 0 | 0 | 0 | 0 | 5 | 0 | 0 | 0 | 0 | 0 | 0 |
| Unwanted plants: | | | | | | | | | | |
| Cyperus esculentus | 100 | 100 | 100 | 100 | 100 | 100 | 100 | 100 | 100 | 100 | 100 | 100 |
| Echinochloa crus-galli | 100 | 100 | 100 | 100 | 100 | 100 | 100 | 100 | 100 | 100 | 100 | 100 |
| Alisma plantago aquatica | 100 | 100 | 100 | 100 | 100 | 100 | 100 | 100 | 100 | 100 | 100 | 100 |
| | III + V | | III + VI | | III + VII | | III + VIII | | III + IX | | |
| | 2 | 1 | 2 | 1 | 2 | 1 | 2 | 1 | 2 | 1 | |
| kg/ha | 1 | 2 | 1 | 2 | 1 | 2 | 1 | 2 | 1 | 2 | |

| | | | | | | | | | |
|---|---|---|---|---|---|---|---|---|---|---|
| Oryza sativa | 0 | 0 | 0 | 5 | 0 | 0 | 0 | 0 | 0 | 0 |
| Cyperus esculentus | 100 | 100 | 100 | 100 | 100 | 100 | 100 | 100 | 100 | 100 |
| Echinochloa crus-galli | 100 | 100 | 100 | 100 | 100 | 100 | 100 | 100 | 100 | 100 |
| Alisma plantago aquatica | 100 | 100 | 100 | 100 | 100 | 100 | 100 | 100 | 100 | 100 |
| | III + XXIV | | III + XXV | | III + XXVI | | IV + XXIV | | | |
| | 2 | 1 | 2 | 1 | 2 | 1 | 2 | 1 | | |
| kg/ha | 1 | 2 | 1 | 2 | 1 | 2 | 1 | 2 | | |

| | | | | | | | | |
|---|---|---|---|---|---|---|---|---|
| Crop plant: | | | | | | | | |
| Oryza sativa | 0 | 0 | 0 | 0 | 0 | 0 | 0 | 0 |
| Unwanted plants: | | | | | | | | |
| Cyperus esculentus | 100 | 100 | 100 | 100 | 100 | 100 | 100 | 100 |
| Echinochloa crus-galli | 80 | 100 | 90 | 98 | 75 | 100 | 87 | 100 |
| Alisma plantago aquatica | 100 | 100 | 100 | 100 | 100 | 100 | 100 | 100 |
| | IV + XXV | | IV + XXVI | XXXI | | I + XXXI | | |
| | 2 | 1 | 2 | 1 | 3 | 4 | 1 | |
| kg/ha | 1 | 2 | 1 | 2 | | 3 | | |

| | | | | | | | | | | |
|---|---|---|---|---|---|---|---|---|---|---|
| Oryza sativa | 0 | 0 | 0 | 0 | 95 | 100 | 100 | | | |
| Cyperus esculentus | 100 | 100 | 100 | 98 | 70 | 90 | 100 | | | |
| Echinochloa crus-galli | 95 | 100 | 80 | 100 | 100 | 100 | 100 | | | |
| Alisma plantago aquatica | 100 | 100 | 100 | 100 | 95 | 100 | 100 | | | |
| | IV + V | | IV + VI | | IV + VII | | IV + | VIII | IV + IX | | I + XXIV |
| | 2 | 1 | 2 | 1 | 2 | 1 | 2 | | 1 | 2 | 2 | 1 |
| kg/ha | 1 | 2 | 1 | 2 | 1 | 2 | 1 | | 2 | 1 | 1 | 1 |

| | | | | | | | | | | | |
|---|---|---|---|---|---|---|---|---|---|---|---|
| Crop plant: | | | | | | | | | | | |
| Oryza sativa | 0 | 0 | 0 | 5 | 0 | 0 | 0 | 0 | 0 | 0 | 0 |
| Unwanted plants: | | | | | | | | | | | |
| Cyperus esculentus | 100 | 100 | 100 | 100 | 100 | 100 | 100 | 100 | 100 | 100 | 100 |
| Echinochloa crus-galli | 100 | 100 | 100 | 100 | 100 | 100 | 100 | 100 | 100 | 90 | 97 |
| Alisma plantago aquatica | 100 | 100 | 100 | 100 | 100 | 100 | 100 | 100 | 100 | 100 | 100 |
| | I + XXV | | I + XXVI | II + | XXIV | II + | XXV | II + | XXVI | | |
| | 2 | 1 | 2 | 1 | 2 | 1 | 2 | 1 | 2 | 1 | |
| kg/ha | 1 | 2 | 1 | 2 | 1 | 2 | 1 | 2 | 1 | 2 | |

| | | | | | | | | | | |
|---|---|---|---|---|---|---|---|---|---|---|
| Oryza sativa | 0 | 0 | 0 | 0 | 0 | 0 | 0 | 0 | 0 | 0 |
| Cyperus esculentus | 100 | 100 | 100 | 100 | 98 | 96 | 100 | 100 | 100 | 100 |
| Echinochloa crus-galli | 95 | 100 | 83 | 100 | 90 | 98 | 95 | 100 | 85 | 100 |
| Alisma plantago aquatica | 100 | 100 | 100 | 100 | 100 | 100 | 100 | 100 | 100 | 100 |
| | XXXII | | | | | I + XXXII | | | | |
| | 0.5 | 0.75 | 1 | 1.5 | 2 | 1 | 0.5 | 0.75 | 1.5 | 0.5 |
| kg/ha | | | | | | 0.5 | 1 | 0.75 | 0.5 | 1.5 |

| | | | | | | | | | |
|---|---|---|---|---|---|---|---|---|---|
| Crop plant: | | | | | | | | | |
| Oryza sativa | 0 | 0 | 0 | 0 | 10 | 0 | 0 | 0 | 0 | 0 |
| Unwanted plants: | | | | | | | | | |
| Cyperus esculentus | 25 | 35 | 40 | 50 | 70 | 100 | 100 | 100 | 100 | 100 |
| Echinochloa crus-galli | 25 | 40 | 65 | 80 | 90 | 85 | 100 | 89 | 93 | 100 |

-continued

| | | | | | | | | | |
|---|---|---|---|---|---|---|---|---|---|
| Alisma plantago aquatica | 0 | 5 | 10 | 15 20 | 95 90 | | 95 100 | | 96 |
| | | | II + XXXII | | | | | | |
| | 1 | 0.5 | 0.75 | 1.5 0.5 | | | | | |
| kg/ha | 0.5 | 1 | 0.75 | 0.5 1.5 | | | | | |
| Oryza sativa | 0 | 0 | 0 | 0 0 | | | | | |
| Cyperus esculentus | 100 | 100 | 100 | 100 100 | | | | | |
| Echinochloa crus-galli | 85 | 100 | 90 | 95 100 | | | | | |
| Alisma plantago aquatica | 90 | 77 | 79 | 100 89 | | | | | |

0 = no damage
100 = complete destruction

EXAMPLE 5

In the greenhouse, various plants were treated at a growth height of from 2 to 18 cm with the following amounts of the following individual active ingredients and compositions thereof as emulsions, pastes, aqueous solutions or tankmixes:

I 3-isopropyl-2,1,3-benzothiadiazinone-(4)-2,2-dioxide,

II 3-isopropyl-2,1,3benzothiadiazinon-(4)-2,2-dioxide sodium salt,

III 3-isopropyl-2,1,3-benzothiadiazinone-(4)-2,2-dioxide dimethylammonium salt,

IV 3-isopropyl-2,1,3-benzothiadiazinone-(4)-2,2-dioxide diethanolammonium salt,

XIX 2-ethoxy-2,3-dihydro-3,3-dimethyl-5-benzofuranylmethane-sulfonate,

XX 2,3-dihydro-3,3-dimethyl-2-ethoxybenzofuran-5-yl-methylaminosulfonate,

XXI 2,3-dihydro-3,3-dimethyl-2-ethoxybenzofuran-5-yl-dimethylaminosulfonate,

XXII 2,3-dihydro-3,3-dimethyl-2-ethoxybenzofuran-5-yl-N-methyl-N-chloroacetylaminosulfonate, XXIII 2,3-dihydro-3,3-dimethyl-2-ethoxybenzofuran-5-yl-methyl-N-acetylaminosulfonate, each of these compounds at rates of 0.25, 0.5, 0.75, 1, 1.25, 1.5, 2, 3 and 4 kg/ha;

I+XIX, I+XX, I+XXI, I+XXII, I+XXIII, II+XIX, II+XX, II+XXI, II+XXII, II+XXIII, III+XIX, III+XX, III+XXI, III+XXII, III+XXIII, IV+XIX, IV+XX, IV+XXI, IV+XXII and IV+XXIII each of these compositions at rates of 1+0.25, 0.25+1, 0.75+0.75, 1.5+0.5, 0.5+1.5, 1+1, 2+1, 1+2, 1.5+1.5 and 2+2 kg/ha.

During the experiment the plants were kept fairly dry.

After 2 to 3 weeks it was ascertained that at the lower application rates the compositions had a better herbicidal action than their components, combined with the same crop plant compatibility. At the higher application rates the compatibility with the crop plant, Pisum sativum, was still good.

The results are given below:

| Active ingredient kg/ha | 0.25 | 0.5 | 0.75 | I 1 | 1.25 | 1.5 | 2 | 3 | 4 |
|---|---|---|---|---|---|---|---|---|---|
| Crop plant: | | | | | | | | | |
| Pisum sativum | 0 | 0 | 0 | 0 | 0 | 0 | 0 | 0 | 5 |
| Unwanted plants: | | | | | | | | | |
| Alopecurus myosuroides | 0 | 3 | 5 | 10 | 10 | 15 | 20 | 30 | 34 |
| Galium aparine | 15 | 30 | 45 | 60 | 65 | 75 | 80 | 95 | 100 |
| Stellaria media | 25 | 30 | 40 | 60 | 65 | 70 | 80 | 95 | 100 |
| | | | | II | | | | | |
| Pisum sativum | 0 | 0 | 0 | 0 | 0 | 0 | 0 | 0 | 5 |
| Alopecurus myosuroides | 0 | 5 | 10 | 12 | 15 | 15 | 18 | 25 | 30 |
| Galium aparine | 15 | 30 | 40 | 60 | 65 | 75 | 80 | 92 | 100 |
| Stellaria media | 10 | 20 | 30 | 55 | 60 | 70 | 80 | 94 | 100 |
| | | | | III | | | | | |
| Crop plant: | | | | | | | | | |
| Pisum sativum | 0 | 0 | 0 | 0 | 0 | 0 | 0 | 0 | 10 |
| Unwanted plants: | | | | | | | | | |
| Alopecurus myosuroides | 0 | 5 | 8 | 12 | 15 | 16 | 21 | 30 | 34 |
| Galium aparine | 20 | 30 | 40 | 50 | 55 | 60 | 75 | 95 | 100 |
| Stellaria media | 20 | 30 | 40 | 50 | 55 | 60 | 75 | 95 | 100 |
| | | | | IV | | | | | |
| Pisum sativum | 0 | 0 | 0 | 0 | 0 | 0 | 0 | 0 | 10 |
| Alopecurus myosuroides | 0 | 4 | 7 | 12 | 15 | 18 | 20 | 25 | 32 |
| Galium aparine | 25 | 35 | 45 | 65 | 70 | 75 | 80 | 95 | 100 |
| Stellaria media | 10 | 20 | 40 | 60 | 70 | 85 | 90 | 98 | 100 |
| | | | | XIX | | | | | |
| Crop plant: | | | | | | | | | |
| Pisum sativum | 0 | 0 | 0 | 0 | 0 | 0 | 0 | 20 | 30 |
| Unwanted plants: | | | | | | | | | |
| Alopecurus myosuroides | 15 | 30 | 45 | 50 | 55 | 60 | 90 | 100 | 100 |
| Galium aparine | 10 | 25 | 30 | 40 | 45 | 50 | 70 | 95 | 100 |
| Stellaria media | 15 | 20 | 30 | 40 | 60 | 70 | 85 | 100 | 100 |
| | | | | XX | | | | | |
| Pisum sativum | 0 | 0 | 0 | 0 | 0 | 0 | 0 | 0 | 10 |
| Alopecurus myosuroides | 10 | 30 | 40 | 45 | 48 | 50 | 60 | 90 | 100 |
| Galium aparine | 10 | 12 | 25 | 40 | 50 | 60 | 70 | 80 | 90 |

|  |  |  |  |  |  |  |  |  |  |
|---|---|---|---|---|---|---|---|---|---|
| Stellaria media | 15 | 20 | 30 | 45 | 55 | 70 | 80 | 95 | 100 |

XXI

|  |  |  |  |  |  |  |  |  |  |
|---|---|---|---|---|---|---|---|---|---|
| Crop plant: |  |  |  |  |  |  |  |  |  |
| Pisum sativum | 0 | 0 | 0 | 0 | 0 | 0 | 0 | 5 | 10 |
| Unwanted plants: |  |  |  |  |  |  |  |  |  |
| Alopecurus myosuroides | 30 | 45 | 70 | 80 | 85 | 90 | 95 | 98 | 100 |
| Galium aparine | 10 | 15 | 25 | 37 | 45 | 58 | 70 | 80 | 92 |
| Stellaria media | 15 | 25 | 40 | 55 | 65 | 75 | 80 | 95 | 100 |

XXII

|  |  |  |  |  |  |  |  |  |  |
|---|---|---|---|---|---|---|---|---|---|
| Pisum sativum | 0 | 0 | 0 | 0 | 0 | 0 | 0 | 0 | 5 |
| Alopecurus myosuroides | 25 | 35 | 50 | 60 | 70 | 80 | 90 | 96 | 100 |
| Galium aparine | 5 | 10 | 20 | 25 | 30 | 40 | 60 | 75 | 85 |
| Stellaria media | 10 | 20 | 30 | 45 | 53 | 60 | 70 | 85 | 95 |

XXIII

|  |  |  |  |  |  |  |  |  |  |
|---|---|---|---|---|---|---|---|---|---|
| Pisum sativum | 0 | 0 | 0 | 0 | 0 | 0 | 0 | 5 | 10 |
| Alopecurus myosuroides | 25 | 35 | 55 | 65 | 75 | 85 | 95 | 98 | 100 |
| Galium aparine | 10 | 20 | 30 | 45 | 55 | 65 | 80 | 90 | 98 |
| Stellaria media | 15 | 25 | 40 | 56 | 70 | 80 | 90 | 98 | 100 |

I + XIX

| kg/ha | 1 | 0.25 | 0.75 | 1.5 | 0.5 | 1 | 1 | 2 | 1.5 | 2 |
|---|---|---|---|---|---|---|---|---|---|---|
|  | 0.25 | 1 | 0.75 | 0.5 | 1.5 | 1 | 2 | 1 | 1.5 | 2 |
| Crop plant: |  |  |  |  |  |  |  |  |  |  |
| Pisum sativum | 0 | 0 | 0 | 0 | 0 | 0 | 0 | 0 | 0 | 0 |
| Unwanted plants: |  |  |  |  |  |  |  |  |  |  |
| Alopecurus myosuroides | 67 | 90 | 90 | 86 | 100 | 100 | 100 | 100 | 100 | 100 |
| Galium aparine | 100 | 95 | 100 | 100 | 100 | 100 | 100 | 100 | 100 | 100 |
| Stellaria media | 100 | 100 | 100 | 100 | 100 | 100 | 100 | 100 | 100 | 100 |

I + XX

|  |  |  |  |  |  |  |  |  |  |  |
|---|---|---|---|---|---|---|---|---|---|---|
| Pisum sativum | 0 | 0 | 0 | 0 | 0 | 0 | 0 | 0 | 0 | 0 |
| Alopecurus myosuroides | 63 | 82 | 84 | 86 | 93 | 95 | 100 | 100 | 100 | 100 |
| Galium aparine | 100 | 95 | 100 | 100 | 100 | 100 | 100 | 100 | 100 | 100 |
| Stellaria media | 100 | 100 | 100 | 100 | 100 | 100 | 100 | 100 | 100 | 100 |

I + XXI

|  |  |  |  |  |  |  |  |  |  |  |
|---|---|---|---|---|---|---|---|---|---|---|
| Crop plant: |  |  |  |  |  |  |  |  |  |  |
| Pisum sativum | 0 | 0 | 0 | 0 | 0 | 0 | 0 | 0 | 0 | 0 |
| Unwanted plants: |  |  |  |  |  |  |  |  |  |  |
| Alopecurus myosuroides | 80 | 100 | 100 | 100 | 100 | 100 | 100 | 100 | 100 | 100 |
| Calium aparine | 100 | 91 | 100 | 100 | 100 | 100 | 100 | 100 | 100 | 100 |
| Stellaria media | 100 | 100 | 100 | 100 | 100 | 100 | 100 | 100 | 100 | 100 |

I + XXII

|  |  |  |  |  |  |  |  |  |  |  |
|---|---|---|---|---|---|---|---|---|---|---|
| Pisum sativum | 0 | 0 | 0 | 0 | 0 | 0 | 0 | 0 | 0 | 0 |
| Alopecurus myosuroides | 75 | 94 | 95 | 98 | 100 | 100 | 100 | 100 | 100 | 100 |
| Galium aparine | 100 | 80 | 100 | 100 | 100 | 100 | 100 | 100 | 100 | 100 |
| Stellaria media | 100 | 100 | 100 | 100 | 100 | 100 | 100 | 100 | 100 | 100 |

I + XXIII

|  |  |  |  |  |  |  |  |  |  |  |
|---|---|---|---|---|---|---|---|---|---|---|
| Pisum sativum | 0 | 0 | 0 | 0 | 0 | 0 | 0 | 0 | 0 | 0 |
| Alopecurus myosuroides | 77 | 90 | 95 | 95 | 100 | 100 | 100 | 100 | 100 | 100 |
| Galium aparine | 100 | 98 | 100 | 100 | 100 | 100 | 100 | 100 | 100 | 100 |
| Stellaria media | 100 | 100 | 100 | 100 | 100 | 100 | 100 | 100 | 100 | 100 |

II + XIX

|  |  |  |  |  |  |  |  |  |  |  |
|---|---|---|---|---|---|---|---|---|---|---|
| Crop plant: |  |  |  |  |  |  |  |  |  |  |
| Pisum sativum | 0 | 0 | 0 | 0 | 0 | 0 | 0 | 0 | 0 | 0 |
| Unwanted plants: |  |  |  |  |  |  |  |  |  |  |
| Alopecurus myosuroides | 70 | 90 | 95 | 96 | 100 | 100 | 100 | 100 | 100 | 100 |
| Galium aparine | 100 | 94 | 100 | 100 | 100 | 100 | 100 | 100 | 100 | 100 |
| Stellaria media | 100 | 90 | 98 | 100 | 100 | 100 | 100 | 100 | 100 | 100 |

II + XX

|  |  |  |  |  |  |  |  |  |  |  |
|---|---|---|---|---|---|---|---|---|---|---|
| Pisum sativum | 0 | 0 | 0 | 0 | 0 | 0 | 0 | 0 | 0 | 0 |
| Alopecurus myosuroides | 65 | 85 | 90 | 92 | 95 | 96 | 100 | 100 | 100 | 100 |
| Galium aparine | 100 | 95 | 100 | 100 | 100 | 100 | 100 | 100 | 100 | 100 |
| Stellaria media | 100 | 95 | 100 | 100 | 100 | 100 | 100 | 100 | 100 | 100 |

II + XXI

|  |  |  |  |  |  |  |  |  |  |  |
|---|---|---|---|---|---|---|---|---|---|---|
| Pisum sativum | 0 | 0 | 0 | 0 | 0 | 0 | 0 | 0 | 0 | 0 |
| Alopecurus myosuroides | 83 | 100 | 100 | 100 | 100 | 100 | 100 | 100 | 100 | 100 |
| Galium aparine | 100 | 92 | 100 | 100 | 100 | 100 | 100 | 100 | 100 | 100 |
| Stellaria media | 100 | 100 | 100 | 100 | 100 | 100 | 100 | 100 | 100 | 100 |

II + XXII

|  |  |  |  |  |  |  |  |  |  |  |
|---|---|---|---|---|---|---|---|---|---|---|
| Crop plant: |  |  |  |  |  |  |  |  |  |  |
| Pisum sativum | 0 | 0 | 0 | 0 | 0 | 0 | 0 | 0 | 0 | 0 |
| Unwanted plants: |  |  |  |  |  |  |  |  |  |  |
| Alopecurus myosuroides | 100 | 78 | 95 | 96 | 98 | 100 | 100 | 100 | 100 | 100 |

-continued

| | | | | | | | | | | |
|---|---|---|---|---|---|---|---|---|---|---|
| Galium aparine | 100 | 100 | 80 | 97 | 100 | 100 | 100 | 100 | 100 | 100 |
| Stellaria media | 100 | 100 | 98 | 100 | 100 | 100 | 100 | 100 | 100 | 100 |

II + XXIII

| | | | | | | | | | | |
|---|---|---|---|---|---|---|---|---|---|---|
| Pisum sativum | 0 | 0 | 0 | 0 | 0 | 0 | 0 | 0 | 0 | 0 |
| Alopecurus myosuroides | 79 | 90 | 90 | 92 | 100 | 100 | 100 | 100 | 100 | 100 |
| Galium aparine | 100 | 98 | 100 | 100 | 100 | 100 | 100 | 100 | 100 | 100 |
| Stellaria media | 100 | 100 | 100 | 100 | 100 | 100 | 100 | 100 | 100 | 100 |

III + XIX

| | | | | | | | | | | |
|---|---|---|---|---|---|---|---|---|---|---|
| Pisum sativum | 0 | 0 | 0 | 0 | 0 | 0 | 0 | 0 | 0 | 0 |
| Alopecurus myosuroides | 69 | 89 | 92 | 95 | 100 | 100 | 100 | 100 | 100 | 100 |
| Galium aparine | 98 | 100 | 100 | 100 | 100 | 100 | 100 | 100 | 100 | 100 |
| Stellaria media | 100 | 100 | 100 | 100 | 100 | 100 | 100 | 100 | 100 | 100 |

III + XX

| | | | | | | | | | | |
|---|---|---|---|---|---|---|---|---|---|---|
| Crop plant: | | | | | | | | | | |
| Pisum sativum | 0 | 0 | 0 | 0 | 0 | 0 | 0 | 0 | 0 | 0 |
| Unwanted plants: | | | | | | | | | | |
| Alopecurus myosuroides | 65 | 83 | 90 | 90 | 95 | 97 | 100 | 100 | 100 | 100 |
| Galium aparine | 98 | 98 | 100 | 100 | 100 | 100 | 100 | 100 | 100 | 100 |
| Stellaria media | 100 | 100 | 100 | 100 | 100 | 100 | 100 | 100 | 100 | 100 |

III + XXI

| | | | | | | | | | | |
|---|---|---|---|---|---|---|---|---|---|---|
| Pisum sativum | 0 | 0 | 0 | 0 | 0 | 0 | 0 | 0 | 0 | 0 |
| Alopecurus myosuroides | 85 | 100 | 100 | 100 | 100 | 100 | 100 | 100 | 100 | 100 |
| Galium aparine | 98 | 95 | 100 | 100 | 100 | 100 | 100 | 100 | 100 | 100 |
| Stellaria media | 100 | 100 | 100 | 100 | 100 | 100 | 100 | 100 | 100 | 100 |

III+ XXI

| | | | | | | | | | | |
|---|---|---|---|---|---|---|---|---|---|---|
| Pisum sativum | 0 | 0 | 0 | 0 | 0 | 0 | 0 | 0 | 0 | 0 |
| Alopecurus myosuroides | 78 | 95 | 95 | 96 | 100 | 100 | 100 | 100 | 100 | 100 |
| Galium aparine | 95 | 88 | 98 | 100 | 100 | 100 | 100 | 100 | 100 | 100 |
| Stellaria media | 100 | 100 | 100 | 100 | 100 | 100 | 100 | 100 | 100 | 100 |

III + XXIII

| | | | | | | | | | | |
|---|---|---|---|---|---|---|---|---|---|---|
| kg/ha | 1 / 0.25 | 0.25 / 1 | 0.75 / 0.75 | 1.5 / 0.5 | 0.5 / 1.5 | 1 / 1 | 2 / 1 | 1 / 2 | 1.5 / 1.5 | 2 / 2 |
| Crop plant: | | | | | | | | | | |
| Pisum sativum | 0 | 0 | 0 | 0 | 0 | 0 | 0 | 0 | 0 | 0 |
| Unwanted plants: | | | | | | | | | | |
| Alopecurus myosuroides | 78 | 90 | 92 | 94 | 100 | 100 | 100 | 100 | 100 | 100 |
| Galium aparine | 100 | 100 | 100 | 100 | 100 | 100 | 100 | 100 | 100 | 100 |
| Stellaria media | 100 | 100 | 100 | 100 | 100 | 100 | 100 | 100 | 100 | 100 |

IV + XIX

| | | | | | | | | | | |
|---|---|---|---|---|---|---|---|---|---|---|
| Pisum sativum | 0 | 0 | 0 | 0 | 0 | 0 | 0 | 0 | 0 | 0 |
| Alopercurus myosuroides | 68 | 87 | 93 | 94 | 100 | 100 | 100 | 100 | 100 | 100 |
| Galium aparine | 100 | 100 | 100 | 100 | 100 | 100 | 100 | 100 | 100 | 100 |
| Stellaria media | 100 | 90 | 100 | 100 | 100 | 100 | 100 | 100 | 100 | 100 |

IV + XX

| | | | | | | | | | | |
|---|---|---|---|---|---|---|---|---|---|---|
| Pisum sativum | 0 | 0 | 0 | 0 | 0 | 0 | 0 | 0 | 0 | 0 |
| Alopecurus myosuroides | 65 | 82 | 86 | 89 | 94 | 97 | 100 | 100 | 100 | 100 |
| Galium aparine | 100 | 100 | 100 | 100 | 100 | 100 | 100 | 100 | 100 | 100 |
| Stellaria media | 100 | 95 | 100 | 100 | 100 | 100 | 100 | 100 | 100 | 100 |

IV + XXI

| | | | | | | | | | | |
|---|---|---|---|---|---|---|---|---|---|---|
| Crop plant: | | | | | | | | | | |
| Pisum sativum | 0 | 0 | 0 | 0 | 0 | 0 | 0 | 0 | 0 | 0 |
| Unwanted plants: | | | | | | | | | | |
| Alopercurus myosuroides | 86 | 100 | 100 | 100 | 100 | 100 | 100 | 100 | 100 | 100 |
| Galium aparine | 100 | 100 | 100 | 100 | 100 | 100 | 100 | 100 | 100 | 100 |
| Stellaria media | 100 | 100 | 100 | 100 | 100 | 100 | 100 | 100 | 100 | 100 |

IV + XXII

| | | | | | | | | | | |
|---|---|---|---|---|---|---|---|---|---|---|
| Pisum sativum | 0 | 0 | 0 | 0 | 0 | 0 | 0 | 0 | 0 | 0 |
| Alopecurus myosuroides | 77 | 96 | 97 | 98 | 100 | 100 | 100 | 100 | 100 | 100 |
| Galium aparine | 100 | 90 | 100 | 100 | 100 | 100 | 100 | 100 | 100 | 100 |
| Stellaria media | 100 | 97 | 100 | 100 | 100 | 100 | 100 | 100 | 100 | 100 |

IV + XXIII

| | | | | | | | | | | |
|---|---|---|---|---|---|---|---|---|---|---|
| Pisum sativum | 0 | 0 | 0 | 0 | 0 | 0 | 0 | 0 | 0 | 0 |
| Alopecurus myosuroides | 78 | 90 | 90 | 94 | 100 | 100 | 100 | 100 | 100 | 100 |
| Galium aparine | 100 | 100 | 100 | 100 | 100 | 100 | 100 | 100 | 100 | 100 |
| Stellaria media | 100 | 100 | 100 | 100 | 100 | 100 | 100 | 100 | 100 | 100 |

0 = no damage
100 = complete destruction

EXAMPLE 6

In the greenhouse, various plants were treated at a growth height of from 3 to 20 cm with the following amounts of the following individual active ingredients and compositions thereof as emulsions, dispersions or aqueous solutions:

Each of these compositions at rates of 0.5+2.5, 1+2, 1+3 and 2+2 kg/ha.

After 2 to 3 weeks it was ascertained that the compositions had a better herbicidal action than their components, combined with the same crop plant compatibility.

The results are given below:

| Active ingredient kg/ha | I 0.5 | 1 | 2 | 3 | 4 | II 0.5 | 1 | 2 | 3 | 4 |
|---|---|---|---|---|---|---|---|---|---|---|
| Crop plant: | | | | | | | | | | |
| Triticum aestivum | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 |
| Secale cereale | 0 | 0 | 0 | 0 | 0 | 0 | 0 | 0 | 0 | 0 |
| Unwanted plants: | | | | | | | | | | |
| Galium aparine | 30 | 60 | 80 | 95 | 100 | 30 | 60 | 80 | 95 | 100 |
| Avena fatua | 0 | 0 | 4 | 5 | 10 | 0 | 0 | 0 | 4 | 10 |

| | III | | | | | IV | | | | |
|---|---|---|---|---|---|---|---|---|---|---|
| Triticum aestivum | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 |
| Secale cereale | 0 | 0 | 0 | 0 | 0 | 0 | 0 | 0 | 0 | 0 |
| Galium aparine | 30 | 50 | 75 | 95 | 100 | 35 | 65 | 80 | 95 | 100 |
| Avena fatua | 0 | 0 | 0 | 2 | 5 | 0 | 0 | 0 | 3 | 5 |

| | XXXV | | | | I + XXXV | | | | II + XXXV | | | |
|---|---|---|---|---|---|---|---|---|---|---|---|---|
| kg/ha | 2 | 2.5 | 3 | 4 | 0.5 2.5 | 1 2 | 1 3 | 2 2 | 0.5 2.5 | 1 2 | 1 3 | 2 2 |
| Crop plant: | | | | | | | | | | | | |
| Triticum aestivum | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 |
| Unwanted plants: | | | | | | | | | | | | |
| Galium aparine | 6 | 10 | 15 | 25 | 90 | 100 | 100 | 100 | 90 | 100 | 100 | 100 |
| Avena fatua | 40 | 50 | 60 | 80 | 95 | 86 | 100 | 90 | 95 | 90 | 100 | 90 |

| | III + XXXV | | | | IV + XXXV | | | |
|---|---|---|---|---|---|---|---|---|
| Triticum aestivum | 0 | 0 | 0 | 0 | 0 | 0 | 0 | 0 |
| Hordeum vulgare | 0 | 0 | 0 | 0 | 0 | 0 | 0 | 0 |
| Secale cereale | 0 | 0 | 0 | 0 | 0 | 0 | 0 | 0 |
| Galium aparine | 92 | 100 | 100 | 100 | 95 | 100 | 100 | 100 |
| Avena fatua | 94 | 92 | 100 | 90 | 95 | 87 | 100 | 90 |

| | XLII | | | | I + XLII | | | | II + XLII | | | |
|---|---|---|---|---|---|---|---|---|---|---|---|---|
| Crop plant: | | | | | | | | | | | | |
| Triticum aestivum | 0 | 0 | 10 | 30 | 0 | 0 | 10 | 0 | 0 | 0 | 10 | 0 |
| Hordeum vulgare | 0 | 5 | 10 | 20 | 5 | 0 | 10 | 0 | 5 | 0 | 10 | 0 |
| Secale cereale | 5 | 10 | 15 | 25 | 10 | 5 | 15 | 5 | 10 | 5 | 15 | 5 |
| Unwanted plants: | | | | | | | | | | | | |
| Galium aparine | 5 | 10 | 15 | 20 | 96 | 100 | 100 | 100 | 95 | 100 | 100 | 100 |
| Avena fatua | 70 | 100 | 100 | 100 | 100 | 100 | 100 | 100 | 100 | 100 | 100 | 100 |

| | III + XLII | | | | IV + XLII | | | |
|---|---|---|---|---|---|---|---|---|
| Triticum aestivum | 0 | 0 | 10 | 0 | 0 | 0 | 10 | 0 |
| Hordeum vulgare | 5 | 0 | 10 | 0 | 5 | 0 | 10 | 0 |
| Secale cereale | 10 | 5 | 15 | 10 | 10 | 5 | 15 | 5 |
| Galium aparine | 92 | 95 | 100 | 100 | 95 | 100 | 100 | 100 |
| Avena fatua | 100 | 100 | 100 | 100 | 100 | 100 | 100 | 100 |

0 = no damage
100 = complete destruction

I 3-isopropyl-2,1,3-benzothiadiazinone-(4)-2,2-dioxide,

II 3-isopropyl-2,1,3-benzothiadiazinone-(4-2,2-dioxide, sodium salt,

III 3-isopropyl-2,1,3-benzothiadiazinone-(4)-2,2-dioxide, dimethylammonium salt, IV 3-isopropyl-2,1,3-benzothiadiazinone-(4)-2,2-dioxide, diethanolammonium salt, each of these compounds at rates of 0.5, 1, 2, 3 and 4 kg/ha;

XXXV amminium-$\alpha,\beta$-dichloro-$\beta$-phenylpropionate

XLII 4-0-(methylaminosulfonyl)-butyn-2-yl-1N-m-chlorophenylcarbamate each of these compounds at rates of 2, 2.5, 3 and 4 kg/ha;

I+XXXV, II+XXXV, III+XXXV, IV+XXXV, I+XLII, II+XLII, III+XLII and IV+XLII

EXAMPLE 7

In the greenhouse, various plants were treated at a growth height of from 2 to 18 cm with the following amounts of the following individual active ingredients and compositions thereof as dispersions, oil dispersions or aqueous solutions:

I 3-isopropyl-2,1,3-benzothiadiazinone-(4)-2,2-dioxide,

II 3-isopropyl-2,1,3-benzothiadiazinone-(4)-2,2-dioxide, sodium salt

III 3-isopropyl-2,1,3-benzothiadiazinone-(4)-2,2-dioxide, dimethylammonium salt, IV 3-isopropyl-2,1,3-benzothiadiazinone-(4)-2,2dioxide, diethanolammonium salt, XXVII trichloroacetic acid, sodium salt XXVIII 2,2-dichloropropionic acid, sodium salt, each of these compounds at rates of 0.25, 0.5, 0.75, 1, 1.5, 2, 3 and 4 kg/ha;

I+XXVII, II+XXVII, III+XXVII, IV+XXVII, II+XXVIII, III+XXVIII and IV+XXVIII

Each composition at rates of 0.25+0.25, 0.5+0.5, 0.75+0.25, 0.25+0.75, 1+0.5, 0.5+1, 0.75+0.75, 1+1, 0.5+1.5, 1.5+0.5, 1.5+1.5, 2+1, 1+2, 3+1, 1+3 and 2+2 kg/ha.

During the experiment the plants were kept fairly dry.

After 2 to 3 weeks it was ascertained that at the lower application rates the compositions had a better herbicidal action than their components, combined with the same crop plant compatibiltiy. Even at the higher rates the compatibility with Linum usitatissimum is still good.

The results are given below:

| Active ingredient kg/ha | 0.25 | 0.5 | 0.75 | I 1 | 1.5 | 2 | 3 | 4 | | | |
|---|---|---|---|---|---|---|---|---|---|---|---|
| Crop plant: | | | | | | | | | | | |
| Linum usitatissimum | 0 | 0 | 0 | 0 | 0 | 0 | 0 | 10 | | | |
| Unwanted plants: | | | | | | | | | | | |
| Alopecurus myosuroides | 0 | 3 | 5 | 10 | 15 | 20 | 30 | 34 | | | |
| Matricaria chamomilla | 10 | 20 | 40 | 60 | 85 | 90 | 95 | 100 | | | |
| | | | | II | | | | | | | |
| Linum usitatissimum | 0 | 0 | 0 | 0 | 0 | 0 | 3 | 10 | | | |
| Alopecurus myosuroides | 0 | 5 | 10 | 12 | 15 | 18 | 25 | 30 | | | |
| Matricaria chamomilla | 10 | 25 | 35 | 60 | 70 | 85 | 95 | 100 | | | |
| | | | | III | | | | | | | |
| Linum usitatissimum | 0 | 0 | 0 | 0 | 0 | 0 | 0 | 10 | | | |
| Alopecurus myosuroides | 0 | 5 | 8 | 12 | 16 | 20 | 30 | 34 | | | |
| Matricaria chamomilla | 15 | 30 | 45 | 65 | 75 | 85 | 96 | 100 | | | |
| | | | | IV | | | | | | | |
| Crop plant: | | | | | | | | | | | |
| Linum usitatissimum | 0 | 0 | 0 | 0 | 0 | 0 | 6 | 14 | | | |
| Unwanted plants: | | | | | | | | | | | |
| Alopecurus myosuroides | 0 | 4 | 7 | 12 | 17 | 20 | 25 | 35 | | | |
| Matricaria chamomilla | 15 | 35 | 50 | 70 | 92 | 98 | 100 | 100 | | | |
| | | | | XXVII | | | | | | | |
| kg/ha | 0.25 | 0.5 | 0.75 | 1 | 1.25 | 1.5 | 2 | 3 | 4 | | |
| Linum usitatissimum | 0 | 0 | 0 | 0 | 0 | 0 | 0 | 5 | 15 | | |
| Alopecurus myosuroides | 10 | 20 | 25 | 30 | 35 | 40 | 50 | 65 | 75 | | |
| Matricaria chamomilla | 0 | 0 | 5 | 7 | 9 | 10 | 14 | 18 | 24 | | |
| | | | | XXVIII | | | | | | | |
| Linum usitatissimum | 0 | 0 | 0 | 0 | 0 | 0 | 0 | 7 | 18 | | |
| Alopecurus myosuroides | 15 | 25 | 30 | 35 | 45 | 50 | 60 | 75 | 90 | | |
| Matricaria chamomilla | 0 | 5 | 5 | 8 | 10 | 10 | 12 | 16 | 20 | | |
| | | | | I+ XXVII | | | | | | | |
| kg/ha | 0.25 0.25 | 0.5 0.5 | 0.75 0.25 | 0.25 0.75 | 1 0.5 | 0.5 1 | 0.75 0.75 | 1 1 | 0.5 1.5 | 1.5 0.5 | 1.5 1.5 |
| Crop plant: | | | | | | | | | | | |
| Linum usitatissimum | 0 | 0 | 0 | 0 | 0 | 0 | 0 | 0 | 0 | 0 | 0 |
| Unwanted plants: | | | | | | | | | | | |
| Alopecurus myosuroides | 40 | 66 | 57 | 70 | 70 | 70 | 69 | 80 | 80 | 73 | 95 |
| Matricaria chamomilla | 55 | 69 | 85 | 63 | 100 | 86 | 94 | 100 | 85 | 100 | 100 |
| | | I +XXVII | | | | II + | XXVII | | | | |
| kg/ha | 2 1 | 1 2 | 3 1 | 1 3 | 2 2 | 0.25 0.75 | 0.5 0.5 | 0.75 0.25 | 0.25 0.75 | 1 0.5 | |
| Linum usitatissimum | 0 | 0 | 0 | 5 | 0 | 0 | 0 | 0 | 0 | 0 | |
| Alopecurus myosuroides | 90 | 95 | 100 | 100 | 100 | 40 | 60 | 60 | 60 | 70 | |
| Matricaria chamomilla | 100 | 100 | 100 | 100 | 100 | 50 | 64 | 80 | 63 | 95 | |
| | | | | II + XXVII | | | | | | | |
| kg/ha | 0.5 1 | 0.75 0.75 | 1 1 | 0.5 1.5 | 1.5 0.5 | 1.5 1.5 | 2 1 | 1 2 | 3 1 | 1 3 | 2 2 |
| Linum usitatissimum | 0 | 0 | 0 | 0 | 0 | 0 | 0 | 0 | 3 | 5 | 0 |
| Alopecurus myosuroides | 75 | 70 | 85 | 82 | 75 | 92 | 94 | 98 | 90 | 100 | 100 |
| Matricaria chamomilla | 80 | 88 | 100 | 90 | 100 | 100 | 100 | 100 | 100 | 100 | 100 |
| | | | | III + XXVII | | | | | | | |
| kg/ha | 0.25 0.25 | 0.5 0.5 | 0.75 0.25 | 0.25 0.75 | 1 0.5 | 0.5 1 | 0.75 0.75 | 1 1 | 0.5 1.5 | 1.5 0.5 | |
| Crop plant: | | | | | | | | | | | |
| Linum usitatissimum | 0 | 0 | 0 | 0 | 0 | 0 | 0 | 0 | 0 | 0 | |
| Unwanted plants: | | | | | | | | | | | |
| Alopecurus myosuroides | 42 | 60 | 55 | 60 | 75 | 75 | 70 | 80 | 85 | 70 | |
| Matricaria chamomilla | 60 | 70 | 90 | 68 | 100 | 80 | 90 | 100 | 90 | 100 | |
| | | III + XXVII | | | | IV + | XXVII | | | | |
| kg/ha | 1.5 1.5 | 2 1 | 1 2 | 3 1 | 1 3 | 2 2 | 0.25 0.25 | 0.5 0.5 | 0.75 0.25 | 0.25 0.75 | 1 0.5 |

-continued

| | | | | | | | | | | | |
|---|---|---|---|---|---|---|---|---|---|---|---|
| Linum usitatissimum | 0 | 0 | 0 | 0 | 5 | 0 | 0 | 0 | 0 | 0 | 0 |
| Alopecurus myosuroides | 98 | 85 | 100 | 98 | 100 | 100 | 46 | 60 | 55 | 64 | 70 |
| Matricaria chamomilla | 100 | 100 | 100 | 100 | 100 | 100 | 60 | 80 | 90 | 78 | 100 |

| | | | | | IV + | XXVII | | | | | |
|---|---|---|---|---|---|---|---|---|---|---|---|
| kg/ha | 0.5 | 0.75 | 1 | 0.5 | 1.5 | 1.5 | 2 | 1 | 3 | 1 | 2 |
| | 1 | 0.75 | 1 | 1.5 | 0.5 | 1.5 | 1 | 2 | 1 | 3 | 2 |

| | | | | | | | | | | | |
|---|---|---|---|---|---|---|---|---|---|---|---|
| Linum usitatissimum | 0 | 0 | 0 | 0 | 0 | 0 | 0 | 0 | 6 | 6 | 0 |
| Alopecurus myosuroides | 70 | 70 | 84 | 82 | 75 | 98 | 90 | 100 | 100 | 100 | 100 |
| Matricaria chamomilla | 95 | 96 | 100 | 100 | 100 | 100 | 100 | 100 | 100 | 100 | 100 |

| | | | | I + | XXVIII | | | | | |
|---|---|---|---|---|---|---|---|---|---|---|
| kg/ha | 0.25 | 0.5 | 0.75 | 0.25 | 1 | 0.5 | 0.75 | 1 | 0.5 | 1.5 | 1.5 |
| | 0.25 | 0.5 | 0.25 | 0.75 | 0.5 | 1 | 0.75 | 1 | 1.5 | 0.5 | 1.5 |

| | | | | | | | | | | | |
|---|---|---|---|---|---|---|---|---|---|---|---|
| Crop plant: | | | | | | | | | | | |
| Linum usitatissimum | 0 | 0 | 0 | 0 | 0 | 0 | 0 | 0 | 0 | 0 | 0 |
| Unwanted plants: | | | | | | | | | | | |
| Alopecurus myosuroides | 55 | 67 | 63 | 70 | 72 | 80 | 78 | 85 | 93 | 84 | 100 |
| Matricaria chamomilla | 57 | 70 | 85 | 64 | 100 | 85 | 90 | 100 | 94 | 100 | 100 |

| | | I + | XXVIII | | | | II | + | XXVIII | | |
|---|---|---|---|---|---|---|---|---|---|---|---|
| kg/ha | 2 | 1 | 3 | 1 | 2 | | 0.25 | 0.5 | 0.75 | 0.25 | 1 |
| | 1 | 2 | 1 | 3 | 2 | | 0.25 | 0.5 | 0.25 | 0.75 | 0.5 |

| | | | | | | | | | | | |
|---|---|---|---|---|---|---|---|---|---|---|---|
| Linum usitatissimum | 0 | 0 | 0 | 7 | 0 | | 0 | 0 | 0 | 0 | 0 |
| Alopecurus myosuroides | 100 | 100 | 100 | 100 | 100 | | 55 | 67 | 65 | 70 | 77 |
| Matricaria chamomilla | 100 | 100 | 100 | 100 | 100 | | 50 | 75 | 80 | 64 | 100 |

| | | | | | II + | XXVIII | | | | | |
|---|---|---|---|---|---|---|---|---|---|---|---|
| kg/ha | 0.5 | 0.75 | 1 | 0.5 | 1.5 | 1.5 | 2 | 1 | 3 | 1 | 2 |
| | 1 | 0.75 | 1 | 1.5 | 0.5 | 1.5 | 1 | 2 | 1 | 3 | 2 |

| | | | | | | | | | | | |
|---|---|---|---|---|---|---|---|---|---|---|---|
| Crop plant: | | | | | | | | | | | |
| Linum usitatissimum | 0 | 0 | 0 | 0 | 0 | 0 | 0 | 0 | 3 | 7 | 0 |
| Unwanted plants: | | | | | | | | | | | |
| Alopecurus myosuroides | 80 | 80 | 90 | 95 | 82 | 100 | 100 | 100 | 100 | 100 | 100 |
| Matricaria chamomilla | 80 | 80 | 100 | 90 | 100 | 100 | 100 | 100 | 100 | 100 | 100 |

| | | | | III | + | XXVIII | | | | |
|---|---|---|---|---|---|---|---|---|---|---|
| kg/ha | 0.25 | 0.5 | 0.75 | 0.25 | 1 | 0.5 | 0.75 | 1 | 0.5 | 1.5 | |
| | 0.25 | 0.5 | 0.25 | 0.75 | 0.5 | 1 | 0.75 | 1 | 1.5 | 0.5 | |

| | | | | | | | | | | |
|---|---|---|---|---|---|---|---|---|---|---|
| Linum usitatissimum | 0 | 0 | 0 | 0 | 0 | 0 | 0 | 0 | 0 | 0 | |
| Alopecurus myosuroides | 60 | 68 | 65 | 75 | 78 | 82 | 80 | 88 | 95 | 80 | |
| Matricaria chamomilla | 55 | 80 | 90 | 69 | 100 | 80 | 90 | 100 | 90 | 100 | |

| | | III + | XXVIII | | | | | IV | + | XXVIII | |
|---|---|---|---|---|---|---|---|---|---|---|---|
| kg/ha | 1.5 | 2 | 1 | 3 | 1 | 2 | | 0.25 | 0.5 | 0.75 | 0.25 |
| | 1.5 | 1 | 2 | 1 | 3 | 2 | | 0.25 | 0.5 | 0.25 | 0.75 |

| | | | | | | | | | | | |
|---|---|---|---|---|---|---|---|---|---|---|---|
| Crop plant: | | | | | | | | | | | |
| Linum usitatissimum | 0 | 0 | 0 | 0 | 7 | 0 | | 0 | 0 | 0 | 0 |
| Unwanted plants: | | | | | | | | | | | |
| Alopecurus myosuroides | 100 | 93 | 100 | 100 | 100 | 100 | | 60 | 69 | 65 | 75 |
| Matricaria chamomilla | 100 | 100 | 100 | 100 | 100 | 100 | | 60 | 85 | 94 | 75 |

| | | | | | IV + | XXVIII | | | | | |
|---|---|---|---|---|---|---|---|---|---|---|---|
| kg/ha | 1 | 0.5 | 0.75 | 1 | 0.5 | 1.5 | 1.5 | 2 | 1 | 3 | 1 | 2 |
| | 0.5 | 1 | 0.75 | 1 | 1.5 | 0.5 | 1.5 | 1 | 2 | 1 | 3 | 2 |

| | | | | | | | | | | | | |
|---|---|---|---|---|---|---|---|---|---|---|---|---|
| Linum usitatissimum | 0 | 0 | 0 | 0 | 0 | 0 | 0 | 0 | 0 | 6 | 7 | 0 |
| Alopecurus myosuroides | 78 | 82 | 80 | 89 | 95 | 85 | 100 | 98 | 100 | 100 | 100 | 100 |
| Matricaria chamomilla | 100 | 95 | 100 | 100 | 100 | 100 | 100 | 100 | 100 | 100 | 100 | 100 |

0 = no damage
100 = complete destruction

EXAMPLE 8

In the open, various plants were treated at a growth height of from 2 to 20 cm with the following amounts of the following individual active ingredients and compositions thereof as dispersions, emulsions or aqueous solutions:

I 3-isopropyl-2,1,3-benzothiadiazinone-(4)-2,2-dioxide

II 3-isopropyl-2,1,3-benzothiadiazinone-(4)-2,2-dioxide sodium salt

III 3-isopropyl-2,1,3-benzothiadiazinone-(4)-2,2-dioxide, dimethylammonium salt

IV 3-isopropyl-2,1,3-benzothiadiazinone-(4)-2,2-dioxide, diethanolammonium salt

XXIX N-(phosphonomethyl)-glycine each of these compounds at rates of 1,2,3 and 4 kg/ha; I+XXIX, II+XXIX, III+XXIX and IV + XXIX each of these compositions at rates of 3+1 and 2+2 kg/ha.

After 3 to 4 weeks it was ascertained that the compositions had a better herbicidal action than their components.

The results are given below:

| Active ingredient | I | | | | II | | | | III | | | |
|---|---|---|---|---|---|---|---|---|---|---|---|---|
| kg/ha | 1 | 2 | 3 | 4 | 1 | 2 | 3 | 4 | 1 | 2 | 3 | 4 |

Unwanted plants:

-continued

| | | | | | | | | | | | | |
|---|---|---|---|---|---|---|---|---|---|---|---|---|
| Galium aparine | 60 | 80 | 95 | 100 | 60 | 80 | 95 | 100 | 50 | 75 | 95 | 100 |
| Lamium amplexicaule | 30 | 60 | 70 | 95 | 25 | 54 | 70 | 86 | 40 | 50 | 60 | 80 |
| Agropyron repens | 0 | 5 | 10 | 15 | 0 | 5 | 10 | 14 | 0 | 2 | 8 | 10 |

| | | IV | | | | XXIX | | |
|---|---|---|---|---|---|---|---|---|
| kg/ha | 1 | 2 | 3 | 4 | 1 | 2 | 3 | 4 |
| Galium aparine | | 65 | 80 | 95 | 100 | 0 | 5 | 10 | 20 |
| Lamium amplexicaule | | 35 | 60 | 75 | 90 | 10 | 25 | 40 | 50 |
| Agropyron repens | | 0 | 0 | 7 | 12 | 20 | 50 | 70 | 100 |

| | XXIX | +I | XXIX | +II | XXIX | +III | XXIX | +IV |
|---|---|---|---|---|---|---|---|---|
| | 3 | 2 | 3 | 2 | 3 | 2 | 3 | 2 |
| kg/ha | 1 | 2 | 1 | 2 | 1 | 2 | 1 | 2 |
| Galium aparine | 100 | 100 | 100 | 100 | 100 | 100 | 100 | 100 |
| Lamium amplexicaule | 100 | 100 | 100 | 100 | 100 | 100 | 100 | 100 |
| Agroypron repens | 100 | 100 | 100 | 100 | 100 | 100 | 100 | 100 |

0 = no damage
100 = complete destruction

EXAMPLE 9

In the greenhouse, various plants were treated at a growth height of from 2 to 20 cm with the following amounts of the following individual active ingredients and compositions thereof as dispersions, emulsions or aqueous solutions:

I 3-isopropyl-2,1,3-benzothiadiazinone-(4)-2,2-dioxide

II 3-isopropyl-2,1,3-benzothiadiazinone-(4)-2,2-dioxide, sodium salt

III 3-isopropyl-2,1,3-benzothiadiazinone-(4)-2,2-dioxide, dimethylammonium salt

IV 3-isopropyl-2,1,3-benzothiadiazinone-(4)-2,2-dioxide, diethanolammonium salt each of these compounds at rates of 0.5, 0.75, 1, 1.5, 2, 2.75, 3, 3.5, 3.75, 4, 4.5 and 5 kg/ha;

XXXVI N-1-naphthylphthalamic acid at rates of 0.5, 1, 1.5, 2, 2.75, 3, 3.5, 3.75, 4 and 4.5 kg/ha;

XXXVII 2-sec-butyl-4,6-dinitrophenol at rates of 0.5, 1, 2, 3, 3.5, 4, 4.5 and 5 kg/ha;

I+XXXVI, II+XXXVI, III+XXXVI and IV+XXVI each at rates of 1+1, 0.5+1.5, 1.5+0.5, 0.75+2, 1.5+1.5, 1+2, 2+1, 0.75+3, 3+1, 1+3 and 2+2 kg/ha;

I+XXXVI+XXXVII, II+XXXVI+XXXVII, III+XXXVI+XXXVII and IV+XXXVI+XXXVII each at rates of 1+0.5+0.5, 0.5+1+0.5, 0.5+0.5+1, 1+2+0.5, 1+3+0.5, 1+2+1 and 1+3+1 kg/ha.

After 2 to 3 weeks it was ascertained that at the lower application rates the compositions had a better herbicidal action than their components, combined with the same crop plant compatibility. Even at the higher application rates the damage caused to the crop plant is low and the herbicidal action strong.

The results are given below:

| Active ingredient | | | | | | I | | | | | |
|---|---|---|---|---|---|---|---|---|---|---|---|
| kg/ha | 0.5 | 0.75 | 1 | 1.5 | 2 | 2.75 | 3 | 3.5 | 3.75 | 4 | 4.5 |
| Crop plant: | | | | | | | | | | | |
| Glycine max | 0 | 0 | 0 | 0 | 0 | 7 | 10 | 15 | 17 | 20 | 25 |
| Unwanted plants: | | | | | | | | | | | |
| Bidens pilosa | 30 | 42 | 50 | 75 | 90 | 100 | 100 | 100 | 100 | 100 | 100 |
| Euphorbia spp. | 20 | 30 | 35 | 60 | 80 | 90 | 95 | 100 | 100 | 100 | 100 |
| | | | | | | II | | | | | |
| Glycine max | 0 | 0 | 0 | 0 | 0 | 10 | 12 | 18 | 20 | 25 | 30 |
| Bidens pilosa | 25 | 35 | 45 | 75 | 90 | 96 | 100 | 100 | 100 | 100 | 100 |
| Euphorbia spp. | 25 | 33 | 40 | 60 | 85 | 90 | 95 | 100 | 100 | 100 | 100 |
| | | | | | | III | | | | | |
| Glycine max | 0 | 0 | 0 | 0 | 0 | 10 | 12 | 15 | 15 | 20 | 25 |
| Bidens pilosa | 25 | 32 | 40 | 70 | 90 | 98 | 100 | 100 | 100 | 100 | 100 |
| Euphorbia spp. | 30 | 37 | 40 | 70 | 85 | 92 | 95 | 100 | 100 | 100 | 100 |
| | | | | | | IV | | | | | |
| Crop plant: | | | | | | | | | | | |
| Glycine max | 0 | 0 | 0 | 0 | 0 | 8 | 10 | 15 | 18 | 20 | 25 |
| Unwanted plants: | | | | | | | | | | | |
| Bidens pilosa | 30 | 40 | 50 | 80 | 90 | 95 | 100 | 100 | 100 | 100 | 100 |
| Euphorbia spp. | 25 | 35 | 40 | 75 | 90 | 96 | 100 | 100 | 100 | 100 | 100 |

| | | | | | XXXVI | | | | | |
|---|---|---|---|---|---|---|---|---|---|---|
| kg/ha | 0.5 | 1 | 1.5 | 2 | 2.75 | 3 | 3.5 | 3.75 | 4 | 4.5 |
| Glycine max | 0 | 0 | 0 | 0 | 0 | 0 | 0 | 0 | 10 | 20 |
| Bidens pilosa | 10 | 15 | 25 | 40 | 50 | 55 | 60 | 65 | 70 | 80 |
| Euphorbia spp. | 7 | 15 | 20 | 35 | 45 | 50 | 65 | 67 | 70 | 77 |

| | | | XXXVII | | | | I | II | III | IV |
|---|---|---|---|---|---|---|---|---|---|---|
| kg/ha | 0.5 | 2 | 3 | 3.5 | 4 | 4.5 | 1 | 5 | 5 | 5 | 5 |
| Glycine max | 0 | 10 | 15 | 20 | 30 | 40 | 5 | 30 | 35 | 28 | 30 |
| Bidens pilosa | 35 | 80 | 90 | 100 | 100 | 100 | 55 | 100 | 100 | 100 | 100 |
| Euphorbia spp. | 30 | 90 | 95 | 100 | 100 | 100 | 65 | 100 | 100 | 100 | 100 |

| | | | | | I+ | XXXVI | | | | |
|---|---|---|---|---|---|---|---|---|---|---|
| | 1 | 0.5 | 1.5 | 0.75 | 1.5 | 1 | 2 | 0.75 | 3 | 1 | 2 |

-continued

| kg/ha | 1 | 1.5 | 0.5 | 2 | 1.5 | 2 | 1 | 3 | 1 | 3 | 2 |
|---|---|---|---|---|---|---|---|---|---|---|---|
| Crop plant: | | | | | | | | | | | |
| Glycine max | 0 | 0 | 0 | 0 | 0 | 0 | 0 | 0 | 10 | 0 | 0 |
| Unwanted plants: | | | | | | | | | | | |
| Bidens pilosa | 100 | 95 | 100 | 100 | 100 | 100 | 100 | 100 | 100 | 100 | 100 |
| Euphorbia spp. | 95 | 85 | 100 | 100 | 100 | 100 | 100 | 100 | 100 | 100 | 100 |

II + XXXVI

| Glycine max | 0 | 0 | 0 | 0 | 0 | 0 | 0 | 0 | 12 | 0 | 0 |
|---|---|---|---|---|---|---|---|---|---|---|---|
| Bidens pilosa | 100 | 95 | 100 | 100 | 100 | 100 | 100 | 100 | 100 | 100 | 100 |
| Euphorbia spp. | 95 | 90 | 100 | 100 | 100 | 100 | 100 | 100 | 100 | 100 | 100 |

III + XXXVI

| Glycine max | 0 | 0 | 0 | 0 | 0 | 0 | 0 | 0 | 12 | 0 | 0 |
|---|---|---|---|---|---|---|---|---|---|---|---|
| Bidens pilosa | 97 | 95 | 100 | 100 | 100 | 100 | 100 | 100 | 100 | 100 | 100 |
| Euphorbia spp. | 95 | 90 | 100 | 100 | 100 | 100 | 100 | 100 | 100 | 100 | 100 |

IV + XXXVI

| | 1 | 1.5 | 0.5 | 2 | 1.5 | 2 | 1 | 3 | 1 | 3 | 2 |
|---|---|---|---|---|---|---|---|---|---|---|---|
| Crop plant: | | | | | | | | | | | |
| Glycine max | 0 | 0 | 0 | 0 | 0 | 0 | 0 | 0 | 10 | 0 | 0 |
| Unwanted plants: | | | | | | | | | | | |
| Bidens pilosa | 100 | 95 | 100 | 100 | 100 | 100 | 100 | 100 | 100 | 100 | 100 |
| Euphorbia spp. | 98 | 92 | 100 | 100 | 100 | 100 | 100 | 100 | 100 | 100 | 100 |

I + XXXVI + XXXVII

| kg/ha | 1 / 0.5 / 0.5 | 0.5 / 1 / 0.5 | 0.5 / 0.5 / 1 | 1 / 2 / 0.5 | 1 / 3 / 0.5 | 1 / 2 / 1 | 1 / 3 / 1 |
|---|---|---|---|---|---|---|---|
| Glycine max | 0 | 0 | 0 | 0 | 0 | 0 | 0 |
| Bidens pilosa | 100 | 100 | 100 | 100 | 100 | 100 | 100 |
| Euphorbia spp. | 100 | 100 | 100 | 100 | 100 | 100 | 100 |

II + XXXVI + XXXVII

| Glycine max | 0 | 0 | 0 | 0 | 0 | 0 | 0 |
|---|---|---|---|---|---|---|---|
| Bidens pilosa | 100 | 100 | 100 | 100 | 100 | 100 | 100 |
| Euphorbia spp. | 100 | 100 | 100 | 100 | 100 | 100 | 100 |

III + XXXVI + XXXVII

| Crop plant: | | | | | | | |
|---|---|---|---|---|---|---|---|
| Glycine max | 0 | 0 | 0 | 0 | 0 | 0 | 0 |
| Unwanted plants: | | | | | | | |
| Bidens pilosa | 100 | 100 | 100 | 100 | 100 | 100 | 100 |
| Euphorbia spp. | 100 | 100 | 100 | 100 | 100 | 100 | 100 |

IV + XXXVI + XXXVII

| Glycine max | 0 | 0 | 0 | 0 | 0 | 0 | 0 |
|---|---|---|---|---|---|---|---|
| Bidens pilosa | 100 | 100 | 100 | 100 | 100 | 100 | 100 |
| Euphorbia spp. | 100 | 100 | 100 | 100 | 100 | 100 | 100 |

| kg/ha | XXXVI 0.75 | 5 | XXXVII 5 |
|---|---|---|---|
| Glycine max | 0 | 30 | 50 |
| Bidens pilosa | 12 | 95 | 100 |
| Euphorbia spp. | 10 | 90 | 100 |

0 = no damage
100 = complete destruction

EXAMPLE 10

In the greenhouse, various plants were treated at a growth height of from 5 to 27 cm with the following amounts of the following individual active ingredients and compositions thereof as dispersions, emulsions or aqueous solutions:

I 3-isopropyl-2,1,3-benzothiadiazinone-(4)-2,2-dioxide

II 3-isopropyl-2,1,3-benzothiadiazinone-(4)-2,2-dioxide, sodium salt

III 3-isopropyl-2,1,3-benzothiadiazinone-(4)-2,2-dioxide, dimethylammonium salt

IV 3-isopropyl-2,1,3-benzothiadiazinone-(4)-2,2-dioxide, diethanolammonium salt

V O-(methylaminosulfonyl)-glycolic acid hexamethylene amide

VIII O-(methylaminosulfonyl)-glycolic acid heptamethylene amide

XXXVIII propionic acid-3,4-dichloroanilide each of these compounds at rates of 0.5, 1, 1.5, 2, 3, 3.5, 4, 4.5, 5 and 5.5 kg/ha, and each of the foregoing amounts being used together with 2 l/ha of a spreader-sticker[+].

I+V+XXXVIII, II+V+XXXVIII, III+V+XXXVIII, IV+V+XXXVIII, I+VIII+XXXVIII and II+VIII+XXXVIII each of these compositions at rates of 1+1+1, 0.5+1.5+1.5, 0.5+2+1, 0.5+1+2, 2+1+1, 1+1.5+1.5, 1+1+2, 1+2+1, 0.5+2+2, 0.5+3+1, 1+3+1, 0.5+2+3, 0.5+0.5+0.5, 0.5+0.5+1, 0.5+1+0.5 and 1+0.5+0.5 kg/ha, each of the foregoing compositions being used together with 2 l/ha of a spreader-sticker[+].

[+] adduct of 6 to 7 moles of ethylene oxide to 1 mole isooctylphenol

After 2 to 3 weeks it was ascertained that the compositions had a better herbicidal action than their components, combined with the same crop plant compatibility.

The results are given below:

| Active ingredient kg/ha | I + 2 l/ha spreader-sticker | | | | | | | | | |
|---|---|---|---|---|---|---|---|---|---|---|
| | 0.5 | 1 | 1.5 | 2 | 3 | 3.5 | 4 | 4.5 | 5 | 5.5 |
| Crop plant: | | | | | | | | | | |
| Oryza sativa | 0 | 0 | 0 | 0 | 0 | 0 | 5 | 5 | 8 | 10 |
| Unwanted plants: | | | | | | | | | | |
| Cyperus esculentus | 35 | 65 | 80 | 90 | 95 | 100 | 100 | 100 | 100 | 100 |
| Echinochloa crus-galli | 5 | 10 | 15 | 20 | 25 | 27 | 30 | 35 | 40 | 47 |
| Alisma plantago aquatica | 40 | 55 | 70 | 80 | 95 | 100 | 100 | 100 | 100 | 100 |
| II + 2 l/ha spreader-sticker | | | | | | | | | | |
| Oryza sativa | 0 | 0 | 0 | 0 | 0 | 0 | 5 | 8 | 10 | 15 |
| Cyperus esculentus | 20 | 50 | 70 | 80 | 95 | 100 | 100 | 100 | 100 | 100 |
| Echinochloa crus-galli | 5 | 15 | 20 | 24 | 30 | 35 | 40 | 44 | 50 | 55 |
| Alisma plantago aquatica | 26 | 50 | 72 | 85 | 95 | 100 | 100 | 100 | 100 | 100 |
| III + 2 l/ha spreader-sticker | | | | | | | | | | |
| Crop plant: | | | | | | | | | | |
| Oryza sativa | 0 | 0 | 0 | 0 | 0 | 0 | 4 | 5 | 10 | 12 |
| Unwanted plants: | | | | | | | | | | |
| Cyperus esculentus | 20 | 50 | 70 | 80 | 90 | 95 | 98 | 100 | 100 | 100 |
| Echinochloa crus-galli | 5 | 10 | 13 | 15 | 25 | 32 | 40 | 45 | 48 | 53 |
| Alisma plantago aquatica | 30 | 52 | 80 | 90 | 98 | 100 | 100 | 100 | 100 | 100 |
| IV + 2 l/ha spreader-sticker | | | | | | | | | | |
| Oryza sativa | 0 | 0 | 0 | 0 | 0 | 0 | 6 | 10 | 15 | 18 |
| Cyperus esculentus | 25 | 50 | 75 | 90 | 95 | 100 | 100 | 100 | 100 | 100 |
| Echinochloa crus-galli | 7 | 14 | 20 | 24 | 30 | 35 | 40 | 40 | 45 | 50 |
| Alisma plantago aquatica | 30 | 58 | 80 | 90 | 96 | 100 | 100 | 100 | 100 | 100 |
| V + 2 l/ha spreader-sticker | | | | | | | | | | |
| Crop plant: | | | | | | | | | | |
| Oryza sativa | 0 | 0 | 0 | 0 | 5 | 7 | 10 | 15 | 20 | 25 |
| Unwanted plants: | | | | | | | | | | |
| Cyperus esculentus | 20 | 40 | 50 | 65 | 80 | 90 | 95 | 100 | 100 | 100 |
| Echinochloa crus-galli | 40 | 70 | 80 | 90 | 98 | 100 | 100 | 100 | 100 | 100 |
| Alisma plantago aquatica | 5 | 15 | 25 | 30 | 35 | 38 | 40 | 50 | 55 | 60 |
| VIII + 2 l/ha spreader-sticker | | | | | | | | | | |
| Oryza sativa | 0 | 0 | 0 | 0 | 5 | 10 | 10 | 14 | 20 | 27 |
| Cyperus esculentus | 6 | 15 | 30 | 40 | 50 | 57 | 60 | 70 | 80 | 95 |
| Echinochloa crus-galli | 35 | 73 | 87 | 94 | 100 | 100 | 100 | 100 | 100 | 100 |
| Alisma plantago aquatica | 0 | 7 | 15 | 20 | 25 | 32 | 35 | 45 | 53 | 60 |
| XXXVIII + 2 l/ha | | | | | | | | | | |
| Oryza sativa | 0 | 0 | 0 | 0 | 10 | 15 | 30 | 35 | 40 | 50 |
| Cyperus esculentus | 0 | 0 | 5 | 10 | 20 | 30 | 35 | 40 | 45 | 50 |
| Echinochloa crus-galli | 18 | 30 | 45 | 60 | 90 | 95 | 100 | 100 | 100 | 100 |
| Alisma plantago aquatica | 5 | 10 | 25 | 35 | 55 | 60 | 70 | 76 | 80 | 86 |

| | I + V + XXXVIII + 2 l/ha spreader-sticker | | | | | | | | | | | |
|---|---|---|---|---|---|---|---|---|---|---|---|---|
| | 1 | 0.5 | 0.5 | 0.5 | 2 | 1 | 1 | 1 | 0.5 | 0.5 | 1 | 0.5 |
| | 1 | 1.5 | 2 | 1 | 1 | 1.5 | 1 | 2 | 2 | 3 | 3 | 2 |
| kg/ha | 1 | 1.5 | 1 | 2 | 1 | 1.5 | 2 | 1 | 2 | 1 | 1 | 3 |
| Crop plant: | | | | | | | | | | | | |
| Oryza sativa | 0 | 0 | 0 | 0 | 0 | 0 | 0 | 0 | 0 | 5 | 5 | 10 |
| Unwanted plants: | | | | | | | | | | | | |
| Cyperus esculentus | 100 | 100 | 100 | 100 | 100 | 100 | 100 | 100 | 100 | 100 | 100 | 100 |
| Echinochloa crus-galli | 100 | 100 | 100 | 100 | 100 | 100 | 100 | 100 | 100 | 100 | 100 | 100 |
| Alisma plantage aquatica | 100 | 100 | 100 | 100 | 100 | 100 | 100 | 100 | 100 | 100 | 100 | 100 |
| II + V + XXXVIII + 2 l/ha spreader-sticker | | | | | | | | | | | | |
| Oryza sativa | 0 | 0 | 0 | 0 | 0 | 0 | 0 | 0 | 0 | 5 | 5 | 10 |
| Cyperus esculentus | 100 | 100 | 100 | 100 | 100 | 100 | 100 | 100 | 100 | 100 | 100 | 100 |
| Echinochloa crus-galli | 100 | 100 | 100 | 100 | 100 | 100 | 100 | 100 | 100 | 100 | 100 | 100 |
| Alisma plantago aquatica | 100 | 100 | 100 | 100 | 100 | 100 | 100 | 100 | 100 | 100 | 100 | 100 |

| | III + V + XXXVIII + 2 l/ha spreader-sticker | | | | | | | | | | | |
|---|---|---|---|---|---|---|---|---|---|---|---|---|
| | 1 | 0.5 | 0.5 | 0.5 | 2 | 1 | 1 | 1 | 0.5 | 0.5 | 1 | 0.5 |
| | 1 | 1.5 | 2 | 1 | 1 | 1.5 | 1 | 2 | 2 | 3 | 3 | 2 |
| kg/ha | 1 | 1.5 | 1 | 2 | 1 | 1.5 | 2 | 1 | 2 | 1 | 1 | 2 |
| Crop plant: | | | | | | | | | | | | |
| Oryza sativa | 0 | 0 | 0 | 0 | 0 | 0 | 0 | 0 | 0 | 5 | 5 | 10 |
| Unwanted plants: | | | | | | | | | | | | |
| Cyperus esculentus | 100 | 100 | 100 | 100 | 100 | 100 | 100 | 100 | 100 | 100 | 100 | 100 |
| Echinochloa crus-galli | 100 | 100 | 100 | 100 | 100 | 100 | 100 | 100 | 100 | 100 | 100 | 100 |
| Alisma plantago aquatica | 100 | 100 | 100 | 100 | 100 | 100 | 100 | 100 | 100 | 100 | 100 | 100 |
| IV + V + XXXVIII + 2 l/ha spreader-sticker | | | | | | | | | | | | |
| Oryza sativa | 0 | 0 | 0 | 0 | 0 | 0 | 0 | 0 | 0 | 5 | 5 | 10 |

-continued

| | | | | | | | | | | | | |
|---|---|---|---|---|---|---|---|---|---|---|---|---|
| Cyperus esculentus | 100 | 100 | 100 | 100 | 100 | 100 | 100 | 100 | 100 | 100 | 100 | 100 |
| Echinochloa crus-galli | 100 | 100 | 100 | 100 | 100 | 100 | 100 | 100 | 100 | 100 | 100 | 100 |
| Alisma plantago aquatica | 100 | 100 | 100 | 100 | 100 | 100 | 100 | 100 | 100 | 100 | 100 | 100 |

| | I + V + XXXVIII + 2 l/ha spreader-sticker | | | | II + V + XXXVIII + 2 l/ha spreader-sticker | | | |
|---|---|---|---|---|---|---|---|---|
| kg/ha | 0.5<br>0.5<br>0.5 | 0.5<br>0.5<br>1 | 0.5<br>1<br>0.5 | 1<br>0.5<br>0.5 | 0.5<br>0.5<br>0.5 | 0.5<br>0.5<br>1 | 0.5<br>1<br>0.5 | 0.5<br>0.5<br>0.5 |
| Crop plant: | | | | | | | | |
| Oryza sativa | 0 | 0 | 0 | 0 | 0 | 0 | 0 | 0 |
| Unwanted plants: | | | | | | | | |
| Cyperus esculentus | 95 | 96 | 100 | 100 | 80 | 85 | 100 | 100 |
| Echinochloa crus-galli | 100 | 100 | 100 | 100 | 100 | 100 | 100 | 100 |
| Alisma plantago aquatica | 90 | 95 | 100 | 100 | 79 | 89 | 90 | 100 |

| | III + V + XXXVIII + 2 l/ha spreader-sticker | | | | IV + V + XXXVII + 2 l/ha spreader-sticker | | | |
|---|---|---|---|---|---|---|---|---|
| Oryza sativa | 0 | 0 | 0 | 0 | 0 | 0 | 0 | 0 |
| Cyperus esculentus | 80 | 86 | 100 | 100 | 85 | 93 | 100 | 100 |
| Echinochloa crus-galli | 100 | 100 | 100 | 100 | 100 | 100 | 100 | 100 |
| Alisma plantago aquatica | 85 | 94 | 95 | 100 | 85 | 94 | 96 | 100 |

| | I + VIII + XXXVIII + 2 l/ha spreader-sticker | | | | | | | | | | | | | | |
|---|---|---|---|---|---|---|---|---|---|---|---|---|---|---|---|---|
| kg/ha | 1<br>1<br>1 | 0.5<br>1.5<br>1.5 | 0.5<br>2<br>1 | 0.5<br>1<br>2 | 2<br>1<br>1 | 1<br>1.5<br>1.5 | 1<br>1<br>2 | 1<br>2<br>1 | 0.5<br>2<br>2 | 0.5<br>3<br>1 | 1<br>3<br>1 | 0.5<br>2<br>3 | 0.5<br>0.5<br>0.5 | 0.5<br>0.5<br>1 | 0.5<br>1<br>0.5 | 1<br>0.5<br>0.5 |
| Crop plant: | | | | | | | | | | | | | | | | |
| Oryza sativa | 0 | 0 | 0 | 0 | 0 | 0 | 0 | 0 | 0 | 5 | 5 | 10 | 0 | 0 | 0 | 0 |
| Unwanted plants: | | | | | | | | | | | | | | | | |
| Cyperus esculentus | 100 | 100 | 100 | 100 | 100 | 100 | 100 | 100 | 100 | 100 | 100 | 100 | 87 | 97 | 97 | 100 |
| Echinochloa crus-galli | 100 | 100 | 100 | 100 | 100 | 100 | 100 | 100 | 100 | 100 | 100 | 100 | 100 | 100 | 100 | 98 |
| Alisma plantago aquatica | 100 | 100 | 100 | 100 | 100 | 100 | 100 | 100 | 100 | 100 | 100 | 100 | 90 | 95 | 98 | 100 |

| | II + VIII + XXXVIII + 2 l/ha spreader-sticker | | | | | | | | | | | | | | |
|---|---|---|---|---|---|---|---|---|---|---|---|---|---|---|---|---|
| kg/ha | 1<br>1<br>1 | 0.5<br>1.5<br>1.5 | 0.5<br>2<br>1 | 0.5<br>1<br>2 | 2<br>1<br>1 | 1<br>1.5<br>1.5 | 1<br>1<br>2 | 1<br>2<br>1 | 0.5<br>2<br>2 | 0.5<br>3<br>1 | 0.5<br>2<br>3 | 0.5<br>0.5<br>0.5 | 0.5<br>0.5<br>1 | 0.5<br>1<br>0.5 | 1<br>0.5<br>0.5 | 1<br>3<br>1 |
| Oryza sativa | 0 | 0 | 0 | 0 | 0 | 0 | 0 | 0 | 0 | 5 | 10 | 0 | 0 | 0 | 0 | 5 |
| Cyperus esculentus | 100 | 100 | 100 | 100 | 100 | 100 | 100 | 100 | 100 | 100 | 100 | 72 | 76 | 80 | 100 | 100 |
| Echinochloa crus-galli | 100 | 100 | 100 | 100 | 100 | 100 | 100 | 100 | 100 | 100 | 100 | 97 | 100 | 100 | 100 | 100 |
| Alisma plantago aquatica | 100 | 100 | 100 | 100 | 100 | 100 | 100 | 100 | 100 | 100 | 100 | 77 | 82 | 85 | 98 | 100 |

0 = no damage
100 = complete destruction

EXAMPLE 11

In the greenhouse, various plants were treated at a growth height of from 5 to 25 cm with the following amounts of the following individual active ingredients and compositions thereof as dispersions or emulsions:

I 3-isopropyl-2,1,3-benzothiadiazinone-(4)-2,2-dioxide

II 3-isopropyl-2,1,3-benzothiadiazinone-(4)-2,2-dioxide, sodium salt

III 3-isopropyl-2,1,3-benzothiadiazinone-(4)-2,2-dioxide, dimethylammonium salt

IV 3-isopropyl-2,1,3-benzothiadiazinone-(4)-2,2-dioxide, diethylammonium salt

IX 3-(isopropylaminosulfonyloxyacetyl)-3-azabicyclo-[3,2,2]-nonane

XXXVIII propionic acid-3,4-dichloroanilide each of these compounds at rates of 0.5, 1, 1.5, 2, 3, 3.5, 4, 4.5, 5 and 5.5 kg/ha, and each of the foegoing amounts being used together with 2 l/ha of a spreader-sticker[+)];

adduct of 6 to 7 moles of ethylene oxide to 1 mole of isooctylphenol I+IX+XXXVIII, II+IX+XXXVIII, III+IX+XXXVIII and IV+IX+XXXVIII each at rates of 1+1+1, 0.5+1.5+1.5, 0.5+2+1, 0.5+1+2, 2+1+1, 1+1+1.5, 1+1+2, 1+2+1, 0.5+2+2, 0.5+3+1, 1+3+1, 0.5+2+3, 0.5+0.5+0.5, 0.5+0.5+1, 0.5+1+0.5, and 1+0.5+0.5 kg/ha, each of these compositions being used together with 2 l/ha of a spreader-sticker[+)].

adduct of 6 to 7 moles of ethylene oxide to 1 mole of isooctylphenol

After 2 to 3 weeks it was ascertained that at the lower application rates the compositions had a better herbicidal action than their components, combined with the same crop plant compatibility. Even at the higher application rates the compatibility with the crop plant is still good.

The results are given below:

| Active ingredient kg/ha | I +2 l/ha spreader-sticker | | | | | | | | | |
|---|---|---|---|---|---|---|---|---|---|---|
| | 0.5 | 1 | 1.5 | 2 | 3 | 3.5 | 4 | 4.5 | 5 | 5.5 |
| Crop plant: | | | | | | | | | | |
| Oryza sativa | 0 | 0 | 0 | 0 | 0 | 0 | 5 | 5 | 8 | 10 |
| Unwanted plants: | | | | | | | | | | |
| Cyperus esculentus | 35 | 65 | 80 | 90 | 95 | 100 | 100 | 100 | 100 | 100 |
| Echinochloa crus-galli | 5 | 10 | 15 | 20 | 25 | 27 | 30 | 35 | 40 | 47 |
| Alisma plantago aquatica | 40 | 55 | 70 | 80 | 95 | 100 | 100 | 100 | 100 | 100 |

II + 2 l/ha spreader-sticker

-continued

| | | | | | | | | | | |
|---|---|---|---|---|---|---|---|---|---|---|
| Oryza sativa | 0 | 0 | 0 | 0 | 0 | 0 | 5 | 8 | 10 | 15 |
| Cyperus esculentus | 20 | 50 | 70 | 80 | 95 | 100 | 100 | 100 | 100 | 100 |
| Echinochloa crus-galli | 5 | 15 | 20 | 24 | 30 | 35 | 40 | 44 | 50 | 55 |
| Alisma plantago aquatica | 26 | 50 | 72 | 85 | 95 | 100 | 100 | 100 | 100 | 100 |

III + 2 l/ha spreader-sticker

| | | | | | | | | | | |
|---|---|---|---|---|---|---|---|---|---|---|
| Oryza sativa | 0 | 0 | 0 | 0 | 0 | 0 | 4 | 5 | 10 | 12 |
| Cyperus esculentus | 20 | 50 | 70 | 80 | 90 | 95 | 98 | 100 | 100 | 100 |
| Echinochloa crus-galli | 5 | 10 | 13 | 15 | 25 | 32 | 40 | 45 | 48 | 53 |
| Alisma plantago aquatica | 30 | 52 | 80 | 90 | 98 | 100 | 100 | 100 | 100 | 100 |

IV + 2 l/ha spreader-sticker

| | | | | | | | | | | |
|---|---|---|---|---|---|---|---|---|---|---|
| Crop plant: | | | | | | | | | | |
| Oryza sativa | 0 | 0 | 0 | 0 | 0 | 0 | 6 | 10 | 15 | 18 |
| Unwanted plants: | | | | | | | | | | |
| Cyperus esculentus | 25 | 50 | 75 | 90 | 95 | 100 | 100 | 100 | 100 | 100 |
| Echinochloa crus-galli | 7 | 14 | 20 | 24 | 30 | 35 | 40 | 40 | 45 | 50 |
| Alisma plantago aquatica | 30 | 58 | 80 | 90 | 96 | 100 | 100 | 100 | 100 | 100 |

IX + 2 l/ha spreader-sticker

| | | | | | | | | | | |
|---|---|---|---|---|---|---|---|---|---|---|
| Oryza sativa | 0 | 0 | 0 | 5 | 10 | 15 | 18 | 20 | 20 | 25 |
| Cyperus esculentus | 6 | 17 | 30 | 35 | 45 | 50 | 60 | 70 | 80 | 90 |
| Echinochloa crus-galli | 28 | 65 | 80 | 90 | 100 | 100 | 100 | 100 | 100 | 100 |
| Alisma plantago aquatica | 2 | 7 | 14 | 17 | 28 | 30 | 32 | 35 | 40 | 45 |

XXXVIII + 2 l/ha spreader-sticker

| | | | | | | | | | | |
|---|---|---|---|---|---|---|---|---|---|---|
| Oryza sativa | 0 | 0 | 0 | 0 | 10 | 15 | 30 | 35 | 40 | 50 |
| Cyperus esculentus | 0 | 0 | 5 | 10 | 20 | 30 | 35 | 40 | 45 | 50 |
| Echinochloa crus-galli | 18 | 30 | 45 | 60 | 90 | 95 | 100 | 100 | 100 | 100 |
| Alisma plantago aquatica | 5 | 10 | 25 | 35 | 55 | 60 | 70 | 76 | 80 | 86 |

I + IX + XXXVIII + 2 l/ha spreader-sticker

| kg/ha | 1 | 0.5 | 0.5 | 0.5 | 2 | 1 | 1 | 0.5 | 0.5 | 0.5 | 0.5 | 0.5 | 0.5 | 1 |
|---|---|---|---|---|---|---|---|---|---|---|---|---|---|---|
| | 1 | 1.5 | 2 | 1 | 1 | 1.5 | 1 | 2 | 2 | 3 | 3 | 2 | 0.5 | 0.5 | 1 | 0.5 |
| | 1 | 1.5 | 1 | 2 | 1 | 1.5 | 2 | 1 | 2 | 1 | 1 | 3 | 0.5 | 1 | 0.5 | 0.5 |

| Crop plant: | | | | | | | | | | | | | | | | |
|---|---|---|---|---|---|---|---|---|---|---|---|---|---|---|---|---|
| Oryza sativa | 0 | 0 | 5 | 0 | 0 | 0 | 0 | 5 | 5 | 10 | 10 | 10 | 0 | 0 | 0 | 0 |
| Unwanted plants: | | | | | | | | | | | | | | | | |
| Cyperus esculentus | 100 | 100 | 100 | 100 | 100 | 100 | 100 | 100 | 100 | 100 | 100 | 100 | 87 | 86 | 98 | 100 |
| Echinochloa crus-galli | 100 | 100 | 100 | 100 | 100 | 100 | 100 | 100 | 100 | 100 | 100 | 100 | 95 | 100 | 100 | 100 |
| Alisma plantago aquatica | 100 | 100 | 100 | 100 | 100 | 100 | 100 | 100 | 100 | 100 | 100 | 100 | 85 | 90 | 90 | 100 |

II + IX + XXXVIII + 2 l/ha spreader-sticker

| | | | | | | | | | | | | | | | | |
|---|---|---|---|---|---|---|---|---|---|---|---|---|---|---|---|---|
| Oryza sativa | 0 | 0 | 5 | 0 | 0 | 0 | 0 | 5 | 5 | 10 | 10 | 10 | 0 | 0 | 0 | 0 |
| Cyperus esculentus | 100 | 100 | 100 | 96 | 100 | 100 | 100 | 100 | 100 | 100 | 100 | 100 | 70 | 75 | 80 | 95 |
| Echinochloa crus-galli | 100 | 100 | 100 | 100 | 100 | 100 | 100 | 100 | 100 | 100 | 100 | 100 | 96 | 100 | 100 | 98 |
| Alisma plantago aquatica | 100 | 100 | 100 | 100 | 100 | 100 | 100 | 100 | 100 | 100 | 100 | 100 | 77 | 82 | 85 | 95 |

III + IX + XXXVIII + 2 l/ha spreader-sticker

| Crop plant: | | | | | | | | | | | | | | | | |
|---|---|---|---|---|---|---|---|---|---|---|---|---|---|---|---|---|
| Oryza sativa | 0 | 0 | 5 | 0 | 0 | 0 | 0 | 5 | 5 | 10 | 10 | 10 | 0 | 0 | 0 | 0 |
| Unwanted plants: | | | | | | | | | | | | | | | | |
| Cyperus esculentus | 100 | 100 | 100 | 95 | 100 | 100 | 100 | 100 | 100 | 100 | 100 | 100 | 72 | 77 | 85 | 94 |
| Echinochloa crus-galli | 100 | 100 | 100 | 100 | 100 | 100 | 100 | 100 | 100 | 100 | 100 | 100 | 94 | 100 | 100 | 98 |
| Alisma plantago aquatica | 100 | 100 | 100 | 100 | 100 | 100 | 100 | 100 | 100 | 100 | 100 | 100 | 85 | 90 | 90 | 95 |

IV + IX + XXXVIII + 2 l/ha spreader-sticker

| | | | | | | | | | | | | | | | | |
|---|---|---|---|---|---|---|---|---|---|---|---|---|---|---|---|---|
| Oryza sativa | 0 | 0 | 5 | 0 | 0 | 0 | 0 | 5 | 5 | 10 | 10 | 10 | 0 | 0 | 0 | 0 |
| Cyperus esculentus | 100 | 98 | 100 | 95 | 100 | 100 | 100 | 100 | 100 | 100 | 100 | 100 | 78 | 85 | 96 | 95 |
| Echinochloa crus-galli | 100 | 100 | 100 | 100 | 100 | 100 | 100 | 100 | 100 | 100 | 100 | 100 | 95 | 100 | 100 | 98 |
| Alisma plantago aquatica | 100 | 100 | 100 | 100 | 100 | 100 | 100 | 100 | 100 | 100 | 100 | 100 | 100 | 92 | 98 | 100 |

0 = no damage
100 = complete destruction

EXAMPLE 12

In the greenhouse, various plants were treated at a growth height of from 3 to 20 cm with the following amounts of the following individual active ingredients and compositions thereof as dispersions or emulsions:

I  3-isopropyl-2,1,3-benzothiadiazinone-(4  )-2,2-dioxide

II  3-isopropyl-2,1,3-benzothiadiazonone-(4)-2,2-dioxide, sodium salt

III  3-isopropyl-2,1,3-benzothiadiazinone-(4)-2,2-dioxide, dimethylammonium salt IV  3-isopropyl-2,1,3-benzothiadiazinone-(4)-2,2-dioxide, diethylammonium salt XLIII propionic acid-3,5-dichloro-4methoxyanilide each of these compounds at rates of 0.5, 1, 1.5, 2, 3, 3.5, 4, 4.5, 5 and 5.5 kg/ha, and each of the foregoing amounts being used together with 2 l/ha of a spreader-sticker adduct of 6 to 7 moles of ethylene oxide to 1 mole of isooctylphenol);
I+XLIII II+XLIII, III+XLIII and IV+XLIII each of these compositions at rates of 0.5+1.5, 1+1, 1.5+0.5, 1+2, 2+1, 1.5+1.5, 3+1, 1+3 and 2+2 kg/ha, each composition being used together with 2 l/ha of a spreader-sticker adduct of 6 to 7 moles of ethylene oxide to 1 mole of isooctylphenol);

After 2 to 3 weeks it was ascertained that at the lower application rates the compositions had a better herbicidal action than their components, combined with the same crop plant compatibility.

Even at the higher application rates the crop plant compatibility was still good. The results are given below:

| Active ingredient kg/ha | 0.5 | 1 | 1.5 | 2 | 3 | 3.5 | 4 | 4.5 | 5 | 5.5 |
|---|---|---|---|---|---|---|---|---|---|---|
| I + 2 l/ha spreader-sticker | | | | | | | | | | |
| Crop plant: | | | | | | | | | | |
| Oryza sativa | 0 | 0 | 0 | 0 | 0 | 0 | 5 | 5 | 8 | 10 |
| Unwanted plants: | | | | | | | | | | |
| Cyperus esculentus | 35 | 65 | 80 | 90 | 95 | 100 | 100 | 100 | 100 | 100 |
| Echinochloa crus-galli | 5 | 10 | 15 | 20 | 27 | 27 | 30 | 35 | 40 | 47 |
| Alisma plantago aquatica | 40 | 55 | 70 | 80 | 95 | 100 | 100 | 100 | 100 | 100 |
| II + 2 l/ha spreader-sticker | | | | | | | | | | |
| Oryza sativa | 0 | 0 | 0 | 0 | 0 | 0 | 5 | 8 | 10 | 15 |
| Cyperus esculentus | 20 | 50 | 70 | 80 | 95 | 100 | 100 | 100 | 100 | 100 |
| Echinochloa crus-galli | 5 | 15 | 20 | 24 | 30 | 35 | 40 | 44 | 50 | 55 |
| Alisma plantago aquatica | 26 | 50 | 72 | 85 | 95 | 100 | 100 | 100 | 100 | 100 |
| III + 2 l/ha spreader-sticker | | | | | | | | | | |
| Oryza sativa | 0 | 0 | 0 | 0 | 0 | 0 | 4 | 5 | 10 | 12 |
| Cyperus esculentus | 20 | 50 | 70 | 80 | 90 | 95 | 98 | 100 | 100 | 100 |
| Echinochloa crus-galli | 5 | 10 | 13 | 15 | 25 | 32 | 40 | 45 | 48 | 53 |
| Alisma plantago aquatica | 30 | 52 | 80 | 90 | 98 | 100 | 100 | 100 | 100 | 100 |
| IV + 2 l/ha spreader-sticker | | | | | | | | | | |
| Crop plant: | | | | | | | | | | |
| Oryza sativa | 0 | 0 | 0 | 0 | 0 | 0 | 6 | 10 | 15 | 18 |
| Unwanted plants: | | | | | | | | | | |
| Cyperus esculentus | 25 | 50 | 75 | 90 | 95 | 100 | 100 | 100 | 100 | 100 |
| Echinochloa crus-galli | 7 | 14 | 20 | 24 | 30 | 35 | 40 | 40 | 45 | 50 |
| Alisma plantago aquatica | 30 | 58 | 80 | 90 | 96 | 100 | 100 | 100 | 100 | 100 |
| XLIII + 2 l/ha spreader-sticker | | | | | | | | | | |
| Oryza sativa | 0 | 0 | 0 | 0 | 0 | 5 | 10 | 15 | 25 | 30 |
| Cyperus esculentus | 0 | 3 | 8 | 15 | 25 | 30 | 35 | 40 | 45 | 50 |
| Echinochloa crus-galli | 15 | 25 | 40 | 60 | 90 | 95 | 100 | 100 | 100 | 100 |
| Alisma plantago aquatica | 10 | 15 | 30 | 40 | 55 | 70 | 80 | 85 | 90 | 95 |

| | | | I + XLIII + 2 l/ha spreader-sticker | | | | | | |
|---|---|---|---|---|---|---|---|---|---|
| kg/ha | 0.5 / 1.5 | 1 / 1 | 1.5 / 0.5 | 1 / 2 | 2 / 1 | 1.5 / 1.5 | 3 / 1 | 1 / 3 | 2 / 2 |
| Crop plant: | | | | | | | | | |
| Oryza sativa | 0 | 0 | 0 | 0 | 0 | 0 | 0 | 0 | 0 |
| Unwanted plants: | | | | | | | | | |
| Cyperus esculentus | 95 | 100 | 100 | 100 | 100 | 100 | 100 | 100 | 100 |
| Echinochloa crus-galli | 90 | 80 | 75 | 100 | 95 | 100 | 100 | 100 | 100 |
| Alisma plantago aquatica | 100 | 100 | 100 | 100 | 100 | 100 | 100 | 100 | 100 |
| II + XLIII + 2 l/ha spreader-sticker | | | | | | | | | |
| Oryza sativa | 0 | 0 | 0 | 0 | 0 | 0 | 0 | 0 | 0 |
| Cyperus esculentus | 80 | 95 | 100 | 100 | 100 | 100 | 100 | 100 | 100 |
| Echinochloa crus-galli | 90 | 80 | 100 | 100 | 96 | 100 | 100 | 100 | 100 |
| Alisma plantago aquatica | 100 | 100 | 100 | 100 | 100 | 100 | 100 | 100 | 100 |
| III + XLIII + 2 l/ha spreader-sticker | | | | | | | | | |
| Crop plant: | | | | | | | | | |
| Oryza sativa | 0 | 0 | 0 | 0 | 0 | 0 | 0 | 0 | 0 |
| Unwanted plants: | | | | | | | | | |
| Cyperus esculentus | 78 | 95 | 100 | 100 | 100 | 100 | 100 | 100 | 100 |
| Echinochloa crus-galli | 85 | 80 | 75 | 100 | 90 | 100 | 100 | 100 | 100 |
| Alisma plantago aquatica | 96 | 100 | 100 | 100 | 100 | 100 | 100 | 100 | 100 |
| IV + XLIII + 2 l/ha spreader-sticker | | | | | | | | | |
| Oryza sativa | 0 | 0 | 0 | 0 | 0 | 0 | 0 | 0 | 0 |
| Cyperus esculentus | 80 | 97 | 100 | 100 | 100 | 100 | 100 | 100 | 100 |
| Echinochloa crus-galli | 90 | 80 | 80 | 100 | 92 | 100 | 100 | 100 | 100 |
| Alisma plantago aquatica | 98 | 100 | 100 | 100 | 100 | 100 | 100 | 100 | 100 |

0 = no damage
100 = complete destruction

EXAMPLE 13

In the greenhouse, various plants were treated at a growth height of from 2 to 18 cm with the following amounts of the following individual active ingredients and compositions thereof as dispersions, emulsions or aqueous solutions: I 3-isopropyl-2,1,3-benzothiadiazinone-(4)-2,2-dioxide II 3-isopropyl-2,1,3-benzothiadiazinone-(4)-2,2-dioxide, sodium salt III 3-isopropyl-2,1,3-benzothiadiazinone-(4)-2,2-dioxide, dimethylammonium salt IV 3-isopropyl-2,1,3-benzothiadiazinone-(4)-2,2-dioxide, diethanolammonium salt XLV 1,2-dimethyl-3,5-diphenyl-4-methylpyrazolium methyl sulfate XLVI 1,2-dimethyl-3,5-diphenyl-4-bromopyrazolium methyl sulfate each of these compounds at rates of 0.5, 0.75, 1 and 1.5 kg/ha; I+XLV, II+XLV, III+XLV, IV+XLV, I+XLVI, II+XLVI, III+XLVI and IV+XLVI, each of these compositions at rates of 0.5+1, 1+0.5 and 0.75+0.75 kg/ha.

After 2 to 3 weeks it was ascertained that the compositions had a better herbicidal action than their components, combined with the same crop plant compatibility. The results are given below:

| Active ingredient kg/ha | I | | | | II | | | | III | | | |
|---|---|---|---|---|---|---|---|---|---|---|---|---|
| | 0.5 | 0.75 | 1 | 1.5 | 0.5 | 0.75 | 1 | 1.5 | 0.5 | 0.75 | 1 | 1.5 |
| Crop plant: | | | | | | | | | | | | |
| Triticum aestivum | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 |
| Unwanted plants: | | | | | | | | | | | | |
| Galium aparine | 30 | 45 | 60 | 75 | 30 | 40 | 60 | 75 | 30 | 40 | 50 | 60 |
| Avena fatua | 0 | 0 | 0 | 0 | 0 | 0 | 0 | 0 | 0 | 0 | 0 | 0 |
| | IV | | | | XXXXV | | | | XXXXVI | | | |
| Triticum aestivum | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 |
| Galium aparine 35 | 45 | 65 | 75 | 0 | 2 | 5 | 7 | 5 | 7 | 10 | 10 | |
| Avena fatua | 0 | 0 | 0 | 0 | 50 | 60 | 70 | 80 | 50 | 55 | 60 | 70 |

| | I+XXXXV | | | II+XXXXV | | | III+XXXXV | | | IV+XXXXV | | |
|---|---|---|---|---|---|---|---|---|---|---|---|---|
| kg/ha | 0.5 / 1 | 1 / 0.5 | 0.75 / 0.75 | 0.5 / 1 | 1 / 0.5 | 0.75 / 0.75 | 0.5 / 1 | 1 / 0.5 | 0.75 / 0.75 | 0.5 / 1 | 1 / 0.5 | 0.75 / 0.75 |
| Crop plant: | | | | | | | | | | | | |
| Triticum aestivum | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 |
| Unwanted plants: | | | | | | | | | | | | |
| Calium aparine | 80 | 95 | 85 | 80 | 95 | 80 | 72 | 87 | 80 | 82 | 100 | 85 |
| Avena fatua | 100 | 98 | 97 | 100 | 90 | 96 | 100 | 85 | 97 | 100 | 87 | 98 |
| | I+XXXXVI | | | II+XXXXVI | | | III+XXXXVI | | | IV+XXXXVI | | |
| Triticum aestivum | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 |
| Galium aparine | 80 | 100 | 90 | 80 | 100 | 85 | 75 | 93 | 84 | 82 | 100 | 90 |
| Avena fatua | 97 | 95 | 92 | 95 | 97 | 92 | 94 | 87 | 95 | 92 | 87 | 93 |

0 = no damage
100 = complete destruction

I claim:

1. A herbicidal composition consisting essentially of an inert carrier having dispersed therein a herbicidally effective amount of a mixture of a. a benzothiadiazinone dioxide of the formula

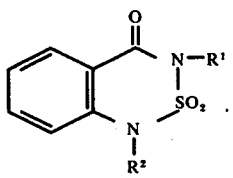

where $R^1$ denotes alkyl of a maximum of 4 carbon atoms and $R^2$ denotes hydrogen, an alkali metal ion, a diloweralkylammonium ion or a dilowerhydroxyalkylammonium ion, and b. a glycolic acid amide of the formula

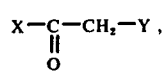

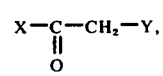

where X denotes

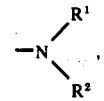

$R^1$ denoting alkyl, alkenyl, alkynyl or alkoxyalkyl of a maximum of 4 carbon atoms and $R^2$ denoting unsubstituted phenyl, phenyl monosubstituted or disubstituted by methyl or ethyl, or X denotes a mono- or bicyclic radical of the formula

n denoting one of the integers 4, 5, 6, 7 and 8, and Y denotes

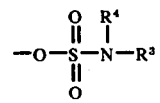

$R^3$ denoting hydrogen or alkyl of a maximum of 4 carbon atoms and $R^4$ denoting alkyl of a maximum of 4 carbon atoms or

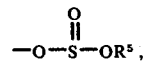

$R^5$ denoting alkyl of a maximum of 4 carbon atoms or methylsulfonyl, and compound a and compound b are in a weight ratio of 1:4 to 4:1.

2. A herbicide composition as claimed in claim 1 wherein compound b has the formula

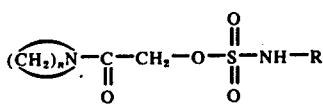

in which

denotes either a monocyclic radical and n denotes 4, 5, 6 or 7 or a bicyclo radical and an denotes 8, and R denotes alkyl having 1 to 8 carbon atoms 3. A herbicide composition as claimed in claim 1 wherein compound a is 3-isopropyl-2,1,3-benzothiadiazinone-(4)-2,2-dioxide or the sodium, dimethylammonium or diethanolammonium salt thereof.

4. A herbicide composition as claimed in claim 1 wherein compound a is 3-isopropyl-2,1,3-benzothiadiazinone-(4)-2,2-dioxide or the sodium, dimethylammonium or diethanolammonium salt thereof, and compound b is a member selected from the group consisting of O-(methylaminosulfonyl)-glycolic acid hexamethylene amide,
O-(ethylaminosulfonyl)-glycolic acid hexamethylene amide,
3-(methylaminosulfonyloxyacetyl)-3-azabicyclo-[3,2,2]-nonane,
O-(methylaminosulfonyl)-glycolic acid heptamethylene amide,
3-(isopropylaminosulfonyloxyacetyl)-3-azabicyclo-[3,2,2]-nonane,
O-(n-propylaminosulfonyl)-glycolic acid hexamethylene amide,
O-(isopropylaminosulfonyl)-glycolic acid hexamethylene amide, and
3-(ethylaminosulfonyloxyacetyl)-3-azabicyclo-[3,2,2]-nonane 5. A herbicide composition as claimed in claim 1 wherein compound a is 3-isopropyl-2,1,3-benzothiadiazinone-(4)-2,2-dioxide and compound b is O-(methylaminosulfonyl)-glycolic acid hexamethylene amide.

6. A herbicide composition as claimed in claim 1 wherein compound a is 3-isopropyl-2,1,3-benzothiadiazinone-(4)-2,2-dioxide and compound b is O-(ethylaminosulfonyl)-glycolic acid hexamethylene amide.

7. A herbicide composition as claimed in claim 1 wherein compound a is 3-isopropyl-2,1,3-benzothiadiazinone-(4)-2,2-dioxide and compound b is 3-(methylaminosulfonyloxyacetyl)-3-azabicyclo-[3,2,2]-nonane.

8. A herbicide composition as claimed in claim 1 wherein compound a is 3-isopropyl-2,1,3-benzothiadiazinone-(4)-2,2-dioxide and compound b is O-(methylaminosulfonyl)-glycolic acid heptamethylene amide.

9. A herbicide composition as claimed in claim 1 wherein compound a is 3-isopropyl-2,1,3-benzothiadiazinone-(4)-2,2-dioxide and compound b is O-(isopropylaminosulfonyl)-glycolic acid hexamethylene amide.

* * * * *